US011851688B2

(12) United States Patent
Tsuji et al.

(10) Patent No.: US 11,851,688 B2
(45) Date of Patent: Dec. 26, 2023

(54) 2-O-SULFATION ENZYME MUTANT AND 3-O-SULFATION ENZYME MUTANT, AND METHOD FOR USING SAME

(71) Applicant: AJINOMOTO CO., INC., Tokyo (JP)

(72) Inventors: Chihiro Tsuji, Kanagawa (JP); Tomoko Shimizu, Kanagawa (JP); Uno Tagami, Kanagawa (JP); Yasuhiro Mihara, Kanagawa (JP); Masayuki Sugiki, Kanagawa (JP); Shogo Nakano, Shizuoka (JP); Tomoharu Motoyama, Shizuoka (JP); Sohei Ito, Shizuoka (JP)

(73) Assignee: AJINOMOTO CO., INC., Tokyo (JP)

( * ) Notice: Subject to any disclaimer, the term of this patent is extended or adjusted under 35 U.S.C. 154(b) by 729 days.

(21) Appl. No.: 16/795,991

(22) Filed: Feb. 20, 2020

(65) Prior Publication Data

US 2020/0181588 A1    Jun. 11, 2020

Related U.S. Application Data

(63) Continuation of application No. PCT/JP2018/033897, filed on Sep. 5, 2018.

(30) Foreign Application Priority Data

Sep. 5, 2017    (JP) ................. 2017-170637

(51) Int. Cl.
*C12N 9/10*    (2006.01)
*C08B 37/00*    (2006.01)
*C12P 19/26*    (2006.01)

(52) U.S. Cl.
CPC ............ *C12N 9/13* (2013.01); *C08B 37/0075* (2013.01); *C12P 19/26* (2013.01); *C12Y 208/02* (2013.01)

(58) Field of Classification Search
CPC ....... C12N 9/13; C08B 37/0075; C12P 19/26; C12Y 208/02
See application file for complete search history.

(56) References Cited

U.S. PATENT DOCUMENTS

| 8,227,449 | B2 | 7/2012 | Oreste et al. |
| 2012/0322114 | A1 | 12/2012 | Liu et al. |
| 2016/0201103 | A1 | 7/2016 | Yamazaki et al. |
| 2018/0237479 | A1 | 8/2018 | Yamazaki et al. |
| 2018/0298117 | A1 | 10/2018 | Mori et al. |
| 2018/0298411 | A1 | 10/2018 | Tokura |

FOREIGN PATENT DOCUMENTS

| EP | 3054005 A1 | 8/2016 |
| WO | WO2017/115674 A1 | 7/2017 |
| WO | WO2017/115675 A1 | 7/2017 |

OTHER PUBLICATIONS

Singh RK et al. Protein Engineering Approaches in the Post-Genomic Era. 2017. Current Protein and Peptide Science. 18. 1-11. (Year: 2017).*
Zhang M et al. Propagated Perturbations from a Peripheral Mutation Show Interactions Supporting WW Domain Thermostability. 2018. Structure. 26. 1474-1485. (Year: 2018).*
Bethea, H. N., et al., "Redirecting the substrate specificity of heparan sulfate 2-O-sulfotransferase by structurally guided mutagenesis," PNAS 2008;105(48):18724-18729.
Chen, J., et al., "Enzymatic Redesigning of Biologically Active Heparan Sulfate," J. Biol. Chem. 2005;280 (52):42817-42825.
Edavettal, S. C., et al., "Crystal Structure and Mutational Analysis of Heparan Sulfate 3-O-Sulfotransferase Isoform 1," J. Biol. Chem. 2004;279(24):25789-25797.
Lindahl, U., et al., "Generation of "Neoheparin" from *E. coli* K5 Capsular Polysaccharide," J. Med. Chem. 2005;48:349-352.
Moon, A. F., et al., "Dissecting the substrate recognition of 3-O-sulfotransferase for the biosynthesis of anticoagulant heparin," PNAS 2012;109(14):5265-5270.
Munoz, E., et al., "Affinity, Kinetic, and Structural Study of the Interaction of 3-O-Sulfotransferase Isoform 1 with Heparan Sulfate," Biochem. 2006;45:5122-5128.
Zhang, Z., et al., "Solution Structures of Chemoenzymatically Synthesized Heparin and Its Precursors," J. Am. Chem. Soc. 2008;130(39):12998-13007.
International Search Report and Written Opinion for PCT Patent App. No. PCT/JP2018/033897 (dated Nov. 28, 2018).
Office Action for U.S. Appl. No. 18/056,853 issued from the United States Patent and Trademark Office dated Oct. 20, 2023.
Sequence Listing; NCBI Reference Sequence XP_021019571.1, "heparan sulfate glucosamine 3-O-sulfotransferase 1 [Mus caroli]"; https://www.ncbi.nlm.nih.gov/protein/1195722382; retrieved on Oct. 17, 2023; pp. 1.

* cited by examiner

*Primary Examiner* — Paul J Holland
(74) *Attorney, Agent, or Firm* — Cermak Nakajima & McGowan LLP; Shelly Guest Cermak

(57) ABSTRACT

The present invention provides a 2-OST mutant exhibiting a high activity. Specifically, the present invention provides a 2-O-sulfation enzyme mutant, having a substitution of a leucine residue at position 321 with a basic amino acid residue in any one amino acid sequence of: (a) the amino acid sequence of SEQ ID NO: 2; (b) an amino acid sequence comprising one or several amino acid substitutions, deletions, insertions, or additions in the amino acid sequence of SEQ ID NO: 2; (c) an amino acid sequence having 90% or more identity to the amino acid sequence of SEQ ID NO: 2; (d) the amino acid sequence consisting of amino acid residues at positions 69 to 356 in the amino acid sequence of SEQ ID NO: 2; (e) an amino acid sequence comprising one or several amino acid substitutions, deletions, insertions, or additions in the amino acid sequence consisting of amino acid residues at positions 69 to 356 in the amino acid sequence of SEQ ID NO: 2; (f) an amino acid sequence having 90% or more identity to the amino acid sequence consisting of amino acid residues at positions 69 to 356 in the amino acid sequence of SEQ ID NO: 2; and having a 2-O-sulfate transfer activity.

10 Claims, 1 Drawing Sheet

Specification includes a Sequence Listing.

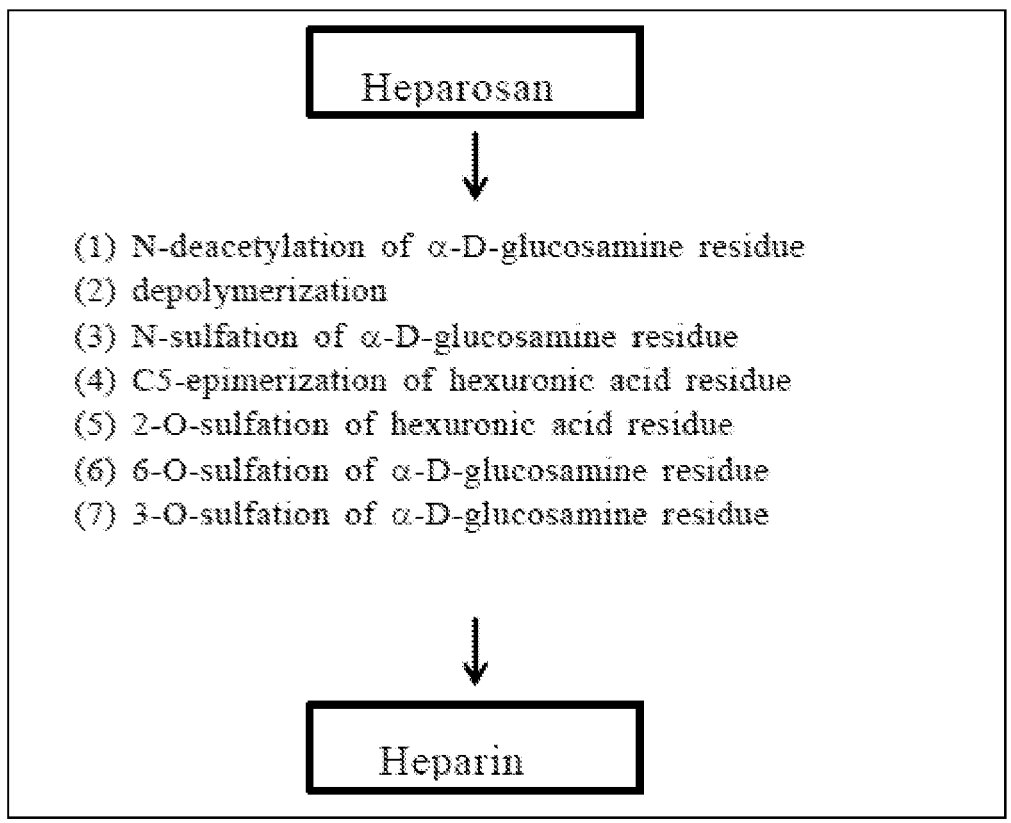

SEQUENCE LISTING

```
<160> NUMBER OF SEQ ID NOS: 138

<210> SEQ ID NO 1
<211> LENGTH: 1068
<212> TYPE: DNA
<213> ORGANISM: Cricetulus barabensis

<400> SEQUENCE: 1
atggggctcc tcaggatcat gatgccgccc aagttgcagc tgctggcggt ggtggccttc      60
gccgtggcga tgctcttctt ggagaaccag atccagaagc tggaggagtc ccgggcgaag     120
ctagaaaggg caatcgcaag acatgaagtc cgggaaattg aacagcggca tacaatggat     180
ggccctcggc aagatgcggc tgtagatgaa gaagaagata tagtcatcat ttataacaga     240
gttcccaaaa ctgcaagcac ctcgtttacc aatatcgcct atgacttgtg tgcgaagaat     300
agataccatg ttcttcacat caacactacc aaaaacaacc cagtgatgtc attgcaagat     360
caggtacgct ttgtaaagaa tataaccact tggaacgaga tgaaaccagg gttttatcat     420
ggacacattt cttatctgga ttttgcaaaa ttcggtgtga agaagaagcc catttacatt     480
aatgtcatca gggaccctat cgagaggctt gtttcctact attactttct gaggtttggg     540
gatgattaca gaccaggatt aaggagacgg aaacaaggag acaaaaagac ctttgatgaa     600
tgtgtggctg agggcggctc agactgtgct ccggagaagc tctggctcca gatcccattt     660
ttctgtggcc acagctcaga atgctggaat gtgggaagca gatgggctat ggatcaagct     720
aagtataacc tcattaacga gtactttctg gtgggagtta ctgaggagct ggaagacttc     780
```

```
atcatgctac tcgaggcagc tttgccccgg ttttttccggg gtgctacaga cctctatcgt    840
acaggaaaga atcccacct gaggaaaacc acagagaaga aacttcccac caagcaaacc      900
atcgcgaagc tgcagcagtc tgacatttgg aaaatggaaa atgagttcta cgagtttgca    960
ctagagcagt tccagttcat cagagcccac gctgtccgtg agaaagatgg agacctctac   1020
atcctggccc agaactttt ctatgaaaag atttacccga agtcgaac                 1068
```

<210> SEQ ID NO 2
<211> LENGTH: 356
<212> TYPE: PRT
<213> ORGANISM: Cricetulus barabensis

<400> SEQUENCE: 2

```
Met Gly Leu Leu Arg Ile Met Pro Pro Lys Leu Gln Leu Leu Ala
1               5                   10                  15

Val Val Ala Phe Ala Val Ala Met Leu Phe Leu Asx Asn Gln Ile Gln
            20                  25                  30

Lys Leu Glu Glu Ser Arg Ala Lys Leu Glu Arg Ala Ile Ala Arg His
        35                  40                  45

Glu Val Arg Glu Ile Glu Gln Arg His Thr Met Asp Gly Pro Arg Gln
50                  55                  60

Asp Ala Ala Val Asp Glu Glu Asp Ile Val Ile Tyr Asn Arg
65                  70                  75                  80

Val Pro Lys Thr Ala Ser Thr Ser Phe Thr Asn Ile Ala Tyr Asp Leu
                85                  90                  95

Cys Ala Lys Asn Arg Tyr His Val Leu His Ile Asn Thr Thr Lys Asn
            100                 105                 110

Asn Pro Val Met Ser Leu Gln Asp Gln Val Arg Phe Val Lys Asn Ile
        115                 120                 125

Thr Thr Trp Asn Glu Met Lys Pro Gly Phe Tyr His Gly His Ile Ser
130                 135                 140

Tyr Leu Asp Phe Ala Lys Phe Gly Val Lys Lys Pro Ile Tyr Ile
145                 150                 155                 160

Asn Val Ile Arg Asp Pro Ile Glu Arg Leu Val Ser Tyr Tyr Tyr Phe
                165                 170                 175

Leu Arg Phe Gly Asp Asp Tyr Arg Pro Gly Leu Arg Arg Lys Gln
            180                 185                 190

Gly Asp Lys Lys Thr Phe Asp Glu Cys Val Ala Glu Gly Gly Ser Asp
        195                 200                 205

Cys Ala Pro Glu Lys Leu Trp Leu Gln Ile Pro Phe Phe Cys Gly His
210                 215                 220

Ser Ser Glu Cys Trp Asn Val Gly Ser Arg Trp Ala Met Asp Gln Ala
225                 230                 235                 240

Lys Tyr Asn Leu Ile Asn Glu Tyr Phe Leu Val Gly Val Thr Glu Glu
                245                 250                 255

Leu Glu Asp Phe Ile Met Leu Glu Ala Ala Leu Pro Arg Phe Phe
            260                 265                 270

Arg Gly Ala Thr Asp Leu Tyr Arg Thr Gly Lys Lys Ser His Leu Arg
        275                 280                 285

Lys Thr Thr Glu Lys Lys Leu Pro Thr Lys Gln Thr Ile Ala Lys Leu
290                 295                 300

Gln Gln Ser Asp Ile Trp Lys Met Glu Asn Glu Phe Tyr Glu Phe Ala
305                 310                 315                 320

Leu Glu Gln Phe Gln Phe Ile Arg Ala His Ala Val Arg Glu Lys Asp
```

```
                      325                 330                 335
Gly Asp Leu Tyr Ile Leu Ala Gln Asn Phe Phe Tyr Glu Lys Ile Tyr
                340                 345                 350

Pro Lys Ser Asn
        355

<210> SEQ ID NO 3
<211> LENGTH: 288
<212> TYPE: PRT
<213> ORGANISM: Artificial Sequence
<220> FEATURE:
<223> OTHER INFORMATION: Amino acid sequence of catalytic site (Asp69-
      Asn356) of Chinese hamster-derived 2-O sulfotransferase (2-OST)

<400> SEQUENCE: 3

Asp Glu Glu Asp Ile Val Ile Ile Tyr Asn Arg Val Pro Lys Thr
1               5                   10                  15

Ala Ser Thr Ser Phe Thr Asn Ile Ala Tyr Asp Leu Cys Ala Lys Asn
                20                  25                  30

Arg Tyr His Val Leu His Ile Asn Thr Thr Lys Asn Asn Pro Val Met
                35                  40                  45

Ser Leu Gln Asp Gln Val Arg Phe Val Lys Asn Ile Thr Thr Trp Asn
        50                  55                  60

Glu Met Lys Pro Gly Phe Tyr His Gly His Ile Ser Tyr Leu Asp Phe
65                  70                  75                  80

Ala Lys Phe Gly Val Lys Lys Pro Ile Tyr Ile Asn Val Ile Arg
            85                  90                  95

Asp Pro Ile Glu Arg Leu Val Ser Tyr Tyr Tyr Phe Leu Arg Phe Gly
                100                 105                 110

Asp Asp Tyr Arg Pro Gly Leu Arg Arg Arg Lys Gln Gly Asp Lys Lys
            115                 120                 125

Thr Phe Asp Glu Cys Val Ala Glu Gly Gly Ser Asp Cys Ala Pro Glu
        130                 135                 140

Lys Leu Trp Leu Gln Ile Pro Phe Phe Cys Gly His Ser Ser Glu Cys
145                 150                 155                 160

Trp Asn Val Gly Ser Arg Trp Ala Met Asp Gln Ala Lys Tyr Asn Leu
                165                 170                 175

Ile Asn Glu Tyr Phe Leu Val Gly Val Thr Glu Glu Leu Glu Asp Phe
                180                 185                 190

Ile Met Leu Leu Glu Ala Ala Leu Pro Arg Phe Phe Arg Gly Ala Thr
        195                 200                 205

Asp Leu Tyr Arg Thr Gly Lys Lys Ser His Leu Arg Lys Thr Thr Glu
        210                 215                 220

Lys Lys Leu Pro Thr Lys Gln Thr Ile Ala Lys Leu Gln Gln Ser Asp
225                 230                 235                 240

Ile Trp Lys Met Glu Asn Glu Phe Tyr Glu Phe Ala Leu Glu Gln Phe
                245                 250                 255

Gln Phe Ile Arg Ala His Ala Val Arg Glu Lys Asp Gly Asp Leu Tyr
                260                 265                 270

Ile Leu Ala Gln Asn Phe Phe Tyr Glu Lys Ile Tyr Pro Lys Ser Asn
        275                 280                 285

<210> SEQ ID NO 4
<211> LENGTH: 356
<212> TYPE: PRT
<213> ORGANISM: Artificial Sequence
<220> FEATURE:
```

<223> OTHER INFORMATION: Amino acid sequence of Chinese hamster-derived
2-O sulfotransferase (2-OST) having Y94A mutation

<400> SEQUENCE: 4

| | | | | | | | | | | | | | | | |
|---|---|---|---|---|---|---|---|---|---|---|---|---|---|---|---|
| Met | Gly | Leu | Leu | Arg | Ile | Met | Met | Pro | Pro | Lys | Leu | Gln | Leu | Leu | Ala |
| 1 | | | | 5 | | | | | 10 | | | | | 15 | |
| Val | Val | Ala | Phe | Ala | Val | Ala | Met | Leu | Phe | Leu | Asx | Asn | Gln | Ile | Gln |
| | | | 20 | | | | | 25 | | | | | 30 | | |
| Lys | Leu | Glu | Glu | Ser | Arg | Ala | Lys | Leu | Glu | Arg | Ala | Ile | Ala | Arg | His |
| | | | | 35 | | | | 40 | | | | | 45 | | |
| Glu | Val | Arg | Glu | Ile | Glu | Gln | Arg | His | Thr | Met | Asp | Gly | Pro | Arg | Gln |
| | 50 | | | | | 55 | | | | | 60 | | | | |
| Asp | Ala | Ala | Val | Asp | Glu | Glu | Asp | Ile | Val | Ile | Ile | Tyr | Asn | Arg | |
| 65 | | | | | 70 | | | | | 75 | | | | | 80 |
| Val | Pro | Lys | Thr | Ala | Ser | Thr | Ser | Phe | Thr | Asn | Ile | Ala | Ala | Asp | Leu |
| | | | | 85 | | | | | 90 | | | | | 95 | |
| Cys | Ala | Lys | Asn | Arg | Tyr | His | Val | Leu | His | Ile | Asn | Thr | Thr | Lys | Asn |
| | | | | 100 | | | | | 105 | | | | | 110 | |
| Asn | Pro | Val | Met | Ser | Leu | Gln | Asp | Gln | Val | Arg | Phe | Val | Lys | Asn | Ile |
| | | | | 115 | | | | | 120 | | | | | 125 | |
| Thr | Thr | Trp | Asn | Glu | Met | Lys | Pro | Gly | Phe | Tyr | His | Gly | His | Ile | Ser |
| | 130 | | | | | 135 | | | | | 140 | | | | |
| Tyr | Leu | Asp | Phe | Ala | Lys | Phe | Gly | Val | Lys | Lys | Pro | Ile | Tyr | Ile | |
| 145 | | | | | 150 | | | | | 155 | | | | | 160 |
| Asn | Val | Ile | Arg | Asp | Pro | Ile | Glu | Arg | Leu | Val | Ser | Tyr | Tyr | Tyr | Phe |
| | | | | 165 | | | | | 170 | | | | | 175 | |
| Leu | Arg | Phe | Gly | Asp | Asp | Tyr | Arg | Pro | Gly | Leu | Arg | Arg | Lys | Gln | |
| | | | 180 | | | | | 185 | | | | | 190 | | |
| Gly | Asp | Lys | Lys | Thr | Phe | Asp | Glu | Cys | Val | Ala | Glu | Gly | Gly | Ser | Asp |
| | | | | 195 | | | | | 200 | | | | | 205 | |
| Cys | Ala | Pro | Glu | Lys | Leu | Trp | Leu | Gln | Ile | Pro | Phe | Phe | Cys | Gly | His |
| | 210 | | | | | 215 | | | | | 220 | | | | |
| Ser | Ser | Glu | Cys | Trp | Asn | Val | Gly | Ser | Arg | Trp | Ala | Met | Asp | Gln | Ala |
| 225 | | | | | 230 | | | | | 235 | | | | | 240 |
| Lys | Tyr | Asn | Leu | Ile | Asn | Glu | Tyr | Phe | Leu | Val | Gly | Val | Thr | Glu | Glu |
| | | | | 245 | | | | | 250 | | | | | 255 | |
| Leu | Glu | Asp | Phe | Ile | Met | Leu | Leu | Glu | Ala | Ala | Leu | Pro | Arg | Phe | Phe |
| | | | 260 | | | | | 265 | | | | | 270 | | |
| Arg | Gly | Ala | Thr | Asp | Leu | Tyr | Arg | Thr | Gly | Lys | Lys | Ser | His | Leu | Arg |
| | | 275 | | | | | 280 | | | | | 285 | | | |
| Lys | Thr | Thr | Glu | Lys | Lys | Leu | Pro | Thr | Lys | Gln | Thr | Ile | Ala | Lys | Leu |
| | 290 | | | | | 295 | | | | | 300 | | | | |
| Gln | Gln | Ser | Asp | Ile | Trp | Lys | Met | Glu | Asn | Glu | Phe | Tyr | Glu | Phe | Ala |
| 305 | | | | | 310 | | | | | 315 | | | | | 320 |
| Leu | Glu | Gln | Phe | Gln | Phe | Ile | Arg | Ala | His | Ala | Val | Arg | Glu | Lys | Asp |
| | | | | 325 | | | | | 330 | | | | | 335 | |
| Gly | Asp | Leu | Tyr | Ile | Leu | Ala | Gln | Asn | Phe | Phe | Tyr | Glu | Lys | Ile | Tyr |
| | | | 340 | | | | | 345 | | | | | 350 | | |
| Pro | Lys | Ser | Asn | | | | | | | | | | | | |
| | | | 355 | | | | | | | | | | | | |

<210> SEQ ID NO 5
<211> LENGTH: 864
<212> TYPE: DNA
<213> ORGANISM: Artificial Sequence
<220> FEATURE:
<223> OTHER INFORMATION: Nucleotide sequence encoding catalytic site (Asp69-Asn356) of Chinese hamster-derived 2-O sulfotransferase (2-OST) having Y94A mutation, which are optimized for codon usage in Escherichia coli

<400> SEQUENCE: 5

```
gatgaagaag aagatatcgt cattatctat aaccgtgttc cgaaaccgc aagcaccagc    60
tttaccaata ttgcagcaga tctgtgcgcc aaaaatcgct atcatgtgct gcatattaac   120
accaccaaaa ataacccggt tatgagcctg caggatcagg ttcgttttgt taaaaacatt   180
accacctgga acgaaatgaa accgggtttt tatcatggcc atatcagcta tctggatttt   240
gcgaaatttg gcgtgaaaaa aaaaccgatc tacatcaacg ttattcgcga tccgattgaa   300
cgtctggtta gctattatta ctttctgcgc ttcggtgatg attatcgtcc gggtctgcgt   360
cgtcgtaaac agggcgacaa aaaaaccttt gatgaatgtg ttgccgaagg tggtagcgat   420
tgtgcaccgg aaaaactgtg gctgcagatt ccgttttttt gcggtcatag cagcgaatgt   480
tggaatgttg gtagccgttg gcaatggat caggccaaat ataacctgat caacgaatat   540
tttctggtgg gtgtgaccga gaactggaa gatttcatta tgctgctgga agcagcactg   600
cctcgttttt ttcgtggtgc aaccgatctg tatcgtaccg gtaaaaaag ccatctgcgt   660
aaaacgacgg aaaaaaaact gccgaccaaa cagaccattg caaaactgca gcagagcgat   720
atttggaaaa tggaaaacga gttttatgaa tttgccctgg aacagtttca gtttattcgt   780
gcacatgcag ttcgtgaaaa agatggtgat ctgtatattc tggcccagaa cttcttctac   840
gaaaaaatct atccgaaaag caat                                          864
```

<210> SEQ ID NO 6
<211> LENGTH: 288
<212> TYPE: PRT
<213> ORGANISM: Artificial Sequence
<220> FEATURE:
<223> OTHER INFORMATION: Amino acid sequence of catalytic site (Asp69-Asn356) of Chinese hamster-derived 2-O sulfotransferase (2-OST) having Y94A mutation

<400> SEQUENCE: 6

```
Asp Glu Glu Glu Asp Ile Val Ile Ile Tyr Asn Arg Val Pro Lys Thr
1               5                   10                  15

Ala Ser Thr Ser Phe Thr Asn Ile Ala Ala Asp Leu Cys Ala Lys Asn
            20                  25                  30

Arg Tyr His Val Leu His Ile Asn Thr Thr Lys Asn Asn Pro Val Met
        35                  40                  45

Ser Leu Gln Asp Gln Val Arg Phe Val Lys Asn Ile Thr Thr Trp Asn
    50                  55                  60

Glu Met Lys Pro Gly Phe Tyr His Gly His Ile Ser Tyr Leu Asp Phe
65                  70                  75                  80

Ala Lys Phe Gly Val Lys Lys Pro Ile Tyr Ile Asn Val Ile Arg
            85                  90                  95

Asp Pro Ile Glu Arg Leu Val Ser Tyr Tyr Tyr Phe Leu Arg Phe Gly
        100                 105                 110

Asp Asp Tyr Arg Pro Gly Leu Arg Arg Arg Lys Gln Gly Asp Lys Lys
    115                 120                 125

Thr Phe Asp Glu Cys Val Ala Glu Gly Gly Ser Asp Cys Ala Pro Glu
    130                 135                 140

Lys Leu Trp Leu Gln Ile Pro Phe Phe Cys Gly His Ser Ser Glu Cys
145                 150                 155                 160
```

```
Trp Asn Val Gly Ser Arg Trp Ala Met Asp Gln Ala Lys Tyr Asn Leu
                165                 170                 175
Ile Asn Glu Tyr Phe Leu Val Gly Val Thr Glu Leu Glu Asp Phe
            180                 185                 190
Ile Met Leu Leu Glu Ala Ala Leu Pro Arg Phe Phe Arg Gly Ala Thr
        195                 200                 205
Asp Leu Tyr Arg Thr Gly Lys Lys Ser His Leu Arg Lys Thr Thr Glu
    210                 215                 220
Lys Lys Leu Pro Thr Lys Gln Thr Ile Ala Lys Leu Gln Gln Ser Asp
225                 230                 235                 240
Ile Trp Lys Met Glu Asn Glu Phe Tyr Glu Phe Ala Leu Glu Gln Phe
                245                 250                 255
Gln Phe Ile Arg Ala His Ala Val Arg Glu Lys Asp Gly Asp Leu Tyr
            260                 265                 270
Ile Leu Ala Gln Asn Phe Phe Tyr Glu Lys Ile Tyr Pro Lys Ser Asn
        275                 280                 285
```

<210> SEQ ID NO 7
<211> LENGTH: 936
<212> TYPE: DNA
<213> ORGANISM: Mus musculus

<400> SEQUENCE: 7

```
atgaccttgc tgctcctggg tgcggtgctg ctggtggccc agccccagct tgtgcattcc      60
cacccggctg ctcctggccc ggggctcaaa cagcaggagc ttctgaggaa ggtgattatt     120
ctcccagagg acaccggaga aggcacagca tccaatggtt ccacacagca gctgccacag     180
accatcatca ttggggtgcg caagggtggt acccgagccc tgctagagat gctcagcctg     240
catcctgatg ttgctgcagc tgaaaacgag gtccatttct ttgactggga ggagcattac     300
agccaaggcc tgggctggta cctcacccag atgcccttct cctcccctca ccagctcacc     360
gtggagaaga caccgcccta tttcacttcg cccaaagtgc tgagagaatt ccacagcatg     420
aaccccacca tccgcctgct gcttatcctg agggacccat cagagcgcgt gctgtccgac     480
tacacccagg tgttgtacaa ccaccttcag aagcacaagc cctatccacc cattgaggac     540
ctcctaatgc gggacggtcg gctgaacctg gactacaagg ctctcaaccg cagcctgtac     600
catgcacaca tgctgaactg gctgcgtttt tcccgttgg ccacatcca cattgtggat       660
ggcgaccgcc tcatcagaga ccctttccct gagatccaga aggtcgaaag attcctgaag     720
cttttctcca cagatcaacgc ctcgaacttc tactttaaca aaaccaaggg cttctactgc     780
ctgcgggaca gtggcaagga ccgctgctta cacgagtcca aggccgggc gcacccccag      840
gtggatccca aactacttga taaactgcac gaatactttc atgagccaaa taagaaattt     900
ttcaagctcg tgggcagaac attcgactgg cactga                              936
```

<210> SEQ ID NO 8
<211> LENGTH: 311
<212> TYPE: PRT
<213> ORGANISM: Mus musculus

<400> SEQUENCE: 8

```
Met Thr Leu Leu Leu Leu Gly Ala Val Leu Leu Val Ala Gln Pro Gln
1               5                   10                  15
Leu Val His Ser His Pro Ala Ala Pro Gly Pro Gly Leu Lys Gln Gln
            20                  25                  30
```

```
Glu Leu Leu Arg Lys Val Ile Ile Leu Pro Glu Asp Thr Gly Glu Gly
             35                  40                  45
Thr Ala Ser Asn Gly Ser Thr Gln Gln Leu Pro Gln Thr Ile Ile Ile
 50                  55                  60
Gly Val Arg Lys Gly Gly Thr Arg Ala Leu Leu Glu Met Leu Ser Leu
 65                  70                  75                  80
His Pro Asp Val Ala Ala Glu Asn Glu Val His Phe Phe Asp Trp
                 85                  90                  95
Glu Glu His Tyr Ser Gln Gly Leu Gly Trp Tyr Leu Thr Gln Met Pro
                100                 105                 110
Phe Ser Ser Pro His Gln Leu Thr Val Glu Lys Thr Pro Ala Tyr Phe
            115                 120                 125
Thr Ser Pro Lys Val Pro Glu Arg Ile His Ser Met Asn Pro Thr Ile
130                 135                 140
Arg Leu Leu Leu Ile Leu Arg Asp Pro Ser Glu Arg Val Leu Ser Asp
145                 150                 155                 160
Tyr Thr Gln Val Leu Tyr Asn His Leu Gln Lys His Lys Pro Tyr Pro
                165                 170                 175
Pro Ile Glu Asp Leu Leu Met Arg Asp Gly Arg Leu Asn Leu Asp Tyr
            180                 185                 190
Lys Ala Leu Asn Arg Ser Leu Tyr His Ala His Met Leu Asn Trp Leu
        195                 200                 205
Arg Phe Phe Pro Leu Gly His Ile His Ile Val Asp Gly Asp Arg Leu
210                 215                 220
Ile Arg Asp Pro Phe Pro Glu Ile Gln Lys Val Glu Arg Phe Leu Lys
225                 230                 235                 240
Leu Ser Pro Gln Ile Asn Ala Ser Asn Phe Tyr Phe Asn Lys Thr Lys
                245                 250                 255
Gly Phe Tyr Cys Leu Arg Asp Ser Gly Lys Asp Arg Cys Leu His Glu
            260                 265                 270
Ser Lys Gly Arg Ala His Pro Gln Val Asp Pro Lys Leu Leu Asp Lys
        275                 280                 285
Leu His Glu Tyr Phe His Glu Pro Asn Lys Lys Phe Phe Lys Leu Val
290                 295                 300
Gly Arg Thr Phe Asp Trp His
305                 310

<210> SEQ ID NO 9
<211> LENGTH: 792
<212> TYPE: DNA
<213> ORGANISM: Artificial Sequence
<220> FEATURE:
<223> OTHER INFORMATION: Nucleotide sequence encoding catalytic site
      (Gly48-His311) of mouse-derived 3-O sulfotransferase (3-OST) which
      are optimized for codon usage in Escherichia coli

<400> SEQUENCE: 9
ggcaccgcaa gcaatggtag cacccagcag ctgccgcaga ccattattat cggtgttcgt      60
aaaggtggca cccgtgcact gctggaaatg ctgagcctgc atcctgatgt tgcagcagca     120
gaaaatgaag tgcatttttt tgattgggag gaacattata gccagggtct gggttggtat     180
ctgacccaga tgccgtttag cagtccgcat cagctgaccg ttgaaaaaac accggcatat     240
ttcaccagcc cgaaagtgcc ggaacgtatt catagcatga atccgaccat tcgcctgctg     300
ctgattctgc gtgatccgag cgaacgtgtt ctgagcgatt ataccaaggt tctgtataat     360
catctgcaga acataaaacc gtatccgcct attgaagatc tgctgatgcg tgatggtcgt     420
```

```
ctgaatctgg attataaagc actgaatcgt agcctgtatc atgcccatat gctgaattgg    480
ctgcgttttt ttccgctggg tcatattcat attgttgatg gtgatcgtct gattcgtgat    540
ccgtttcctg aaattcagaa agtggaacgt tttctgaaac tgagtccgca gattaatgcc    600
agcaacttct attttaacaa aaccaaaggc ttctattgcc tgcgtgatag cggtaaagat    660
cgttgtctgc atgaaagcaa aggtcgtgca catccgcagg ttgatccgaa actgctggat    720
aaactgcatg aatattttca tgaaccgaac aaaaaattct taaaactggt gggtcgtacc    780
ttcgattggc at                                                        792
```

<210> SEQ ID NO 10
<211> LENGTH: 264
<212> TYPE: PRT
<213> ORGANISM: Artificial Sequence
<220> FEATURE:
<223> OTHER INFORMATION: Amino acid sequence of catalytic site (Gly48-His311) of mouse-derived 3-O sulfotransferase (3-OST)

<400> SEQUENCE: 10

```
Gly Thr Ala Ser Asn Gly Ser Thr Gln Gln Leu Pro Gln Thr Ile Ile
1               5                   10                  15

Ile Gly Val Arg Lys Gly Gly Thr Arg Ala Leu Leu Glu Met Leu Ser
            20                  25                  30

Leu His Pro Asp Val Ala Ala Ala Glu Asn Glu Val His Phe Phe Asp
        35                  40                  45

Trp Glu Glu His Tyr Ser Gln Gly Leu Gly Trp Tyr Leu Thr Gln Met
    50                  55                  60

Pro Phe Ser Ser Pro His Gln Leu Thr Val Glu Lys Thr Pro Ala Tyr
65                  70                  75                  80

Phe Thr Ser Pro Lys Val Pro Glu Arg Ile His Ser Met Asn Pro Thr
                85                  90                  95

Ile Arg Leu Leu Leu Ile Leu Arg Asp Pro Ser Glu Arg Val Leu Ser
            100                 105                 110

Asp Tyr Thr Gln Val Leu Tyr Asn His Leu Gln Lys His Lys Pro Tyr
        115                 120                 125

Pro Pro Ile Glu Asp Leu Leu Met Arg Asp Gly Arg Leu Asn Leu Asp
    130                 135                 140

Tyr Lys Ala Leu Asn Arg Ser Leu Tyr His Ala His Met Leu Asn Trp
145                 150                 155                 160

Leu Arg Phe Phe Pro Leu Gly His Ile His Ile Val Asp Gly Asp Arg
                165                 170                 175

Leu Ile Arg Asp Pro Phe Pro Glu Ile Gln Lys Val Glu Arg Phe Leu
            180                 185                 190

Lys Leu Ser Pro Gln Ile Asn Ala Ser Asn Phe Tyr Phe Asn Lys Thr
        195                 200                 205

Lys Gly Phe Tyr Cys Leu Arg Asp Ser Gly Lys Asp Arg Cys Leu His
    210                 215                 220

Glu Ser Lys Gly Arg Ala His Pro Gln Val Asp Pro Lys Leu Leu Asp
225                 230                 235                 240

Lys Leu His Glu Tyr Phe His Glu Pro Asn Lys Lys Phe Phe Lys Leu
                245                 250                 255

Val Gly Arg Thr Phe Asp Trp His
            260
```

<210> SEQ ID NO 11

```
<211> LENGTH: 36
<212> TYPE: DNA
<213> ORGANISM: Artificial Sequence
<220> FEATURE:
<223> OTHER INFORMATION: primer

<400> SEQUENCE: 11
agctgagtcg accccagga aaaattggtt aataac                                36

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agctgagcat gcttccaact gcgctaatga cgc                                  33

<210> SEQ ID NO 13
<211> LENGTH: 313
<212> TYPE: DNA
<213> ORGANISM: Artificial Sequence
<220> FEATURE:
<223> OTHER INFORMATION: fragment

<400> SEQUENCE: 13
gcatgcttcc aactgcgcta atgacgcagc tggacgaagg cgggattctc gtcttacccg      60
taggggagga gcaccagtat ttgaaacggg tgcgtcgtcg gggaggcgaa tttattatcg     120
ataccgtgga ggccgtgcgc tttgtccctt tagtgaaggg tgagctggct taaaacgtga     180
ggaaatacct ggatttttcc tggttatttt gccgcaggtc agcgtatcgt gaacatcttt     240
tccagtgttc agtagggtgc cttgcacggt aattatgtca ctggttatta accaattttt     300 cctggggtc gac                                                        313

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
agctgatcta gaaaacagaa tttgcctggc ggc                                  33

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
agctgaggat ccaggaagag tttgtagaaa cgc                                  33

<210> SEQ ID NO 16
<211> LENGTH: 369
<212> TYPE: DNA
<213> ORGANISM: Artificial Sequence
<220> FEATURE:
<223> OTHER INFORMATION: fragment

<400> SEQUENCE: 16
tctagaaaca gaatttgcct ggcggcagta gcgcggtggt cccacctgac cccatgccga      60
```

```
actcagaagt gaaacgccgt agcgccgatg gtagtgtggg gtctccccat gcgagagtag    120
ggaactgcca ggcatcaaat aaaacgaaag gctcagtcga aagactgggc ctttcgtttt    180
atctgttgtt tgtcggtgaa cgctctcctg agtaggacaa atccgccggg agcggatttg    240
aacgttgcga agcaacggcc cggagggtgg cgggcaggac gcccgccata aactgccagg    300
catcaaatta agcagaaggc catcctgacg gatggccttt ttgcgtttct acaaactctt    360
cctggatcc                                                            369
```

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17

```
ttcctggggg tcgacatgac tacgaaaatt tttaa                                35
```

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18

```
attctgtttt ctagactaag gaaccaacac aagct                                35
```

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19

```
gtcgaccccc aggaaaaatt ggttaataac                                      30
```

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20

```
tctagaaaac agaatttgcc tggcggcagt                                      30
```

<210> SEQ ID NO 21
<211> LENGTH: 1980
<212> TYPE: DNA
<213> ORGANISM: Flavobacterium heparinum

<400> SEQUENCE: 21

```
atgactacga aaatttttaa aaggatcatt gtatttgctg taattgccct atcgtcggga     60
aatatacttg cacaaagctc ttccattacc aggaaagatt ttgaccacat caaccttgag    120
tattccggac tggaaaaggt taataaagca gttgctgccg gcaactatga cgatgcggcc    180
aaagcattac tggcatacta cagggaaaaa agtaaggcca gggaacctga tttcagtaat    240
gcagaaaagc ctgccgatat acgccagccc atagataagg ttacgcgtga atggccgac    300
```

```
aaggctttgg tccaccagtt tcaaccgcac aaaggctacg gctattttga ttatggtaaa    360
gacatcaact ggcagatgtg gccggtaaaa gacaatgaag tacgctggca gttgcaccgt    420
gtaaaatggt ggcaggctat ggccctggtt tatcacgcta cgggcgatga aaaatatgca    480
agagaatggg tatatcagta cagcgattgg gccagaaaaa acccattggg cctgtcgcag    540
gataatgata aatttgtgtg gcggccccctt gaagtgtcgg acagggtaca aagtcttccc    600
ccaaccttca gcttatttgt aaactcgcca gcctttaccc cagccttttt aatggaattt    660
ttaaacagtt accaccaaca ggccgattat ttatctacgc attatgccga acagggaaac    720
caccgtttat ttgaagccca acgcaacttg tttgcagggg tatctttccc tgaatttaaa    780
gattcaccaa gatggaggca aaccggcata tcggtgctga caccgagat caaaaaacag    840
gtttatgccg atgggatgca gtttgaactt tcaccaattt accatgtagc tgccatcgat    900
atcttcttaa aggcctatgg ttctgcaaaa cgagttaacc ttgaaaaaga atttccgcaa    960
tcttatgtac aaactgtaga aaatatgatt atggcgctga tcagtatttc actgccagat    1020
tataacaccc ctatgtttgg agattcatgg attacagata aaaatttcag gatggcacag    1080
tttgccagct gggcccgggt ttccccggca aaccaggcca taaatatttt tgctacagat    1140
ggcaaacaag gtaaggcgcc taactttttta tccaaagcat tgagcaatgc aggcttttat    1200
acgtttagaa gcggatggga taaaaatgca accgttatgg tattaaaagc cagtcctccc    1260
ggagaatttc atgcccagcc ggataacggg acttttgaac ttttttataaa gggcagaaac    1320
tttaccccag acgccggggt atttgtgtat agcggcgacg aagccatcat gaaactgcgg    1380
aactggtacc gtcaaacccg catacacagc acgcttacac tcgacaatca aaatatggtc    1440
attaccaaag cccggcaaaa caatgggaa acaggaaata accttgatgt gcttacctat    1500
accaacccaa gctatccgaa tctggaccat cagcgcagtg tactttttcat caacaaaaaa    1560
tactttctgg tcatcgatag ggcaataggc gaagctaccg gaaacctggg cgtacactgg    1620
cagcttaaag aagacagcaa ccctgttttc gataagacaa agaaccgggt ttacaccact    1680
tacagagatg gtaacaacct gatgatccaa tcgttgaatg cggacaggac cagcctcaat    1740
gaagaagaag gaaaggtatc ttatgtttac aataaggagc tgaaaagacc tgctttcgta    1800
tttgaaaagc ctaaaaagaa tgccggcaca caaaattttg tcagtatagt ttatccatac    1860
gacggccaga aggctccaga gatcagcata cgggaaaaca agggcaatga ttttgagaaa    1920
ggcaagctta atctaaccct taccattaac ggaaaaacaac agcttgtgtt ggttccttag    1980
```

<210> SEQ ID NO 22
<211> LENGTH: 659
<212> TYPE: PRT
<213> ORGANISM: Flavobacterium heparinum

<400> SEQUENCE: 22

Met Thr Thr Lys Ile Phe Lys Arg Ile Ile Val Phe Ala Val Ile Ala
1               5                   10                  15

Leu Ser Ser Gly Asn Ile Leu Ala Gln Ser Ser Ile Thr Arg Lys
            20                  25                  30

Asp Phe Asp His Ile Asn Leu Glu Tyr Ser Gly Leu Glu Lys Val Asn
        35                  40                  45

Lys Ala Val Ala Ala Gly Asn Tyr Asp Asp Ala Lys Ala Leu Leu
    50                  55                  60

Ala Tyr Tyr Arg Glu Lys Ser Lys Ala Arg Glu Pro Asp Phe Ser Asn
65                  70                  75                  80

```
Ala Glu Lys Pro Ala Asp Ile Arg Gln Pro Ile Asp Lys Val Thr Arg
                85                  90                  95
Glu Met Ala Asp Lys Ala Leu Val His Gln Phe Gln Pro His Lys Gly
            100                 105                 110
Tyr Gly Tyr Phe Asp Tyr Gly Lys Asp Ile Asn Trp Gln Met Trp Pro
        115                 120                 125
Val Lys Asp Asn Glu Val Arg Trp Gln Leu His Arg Val Lys Trp Trp
    130                 135                 140
Gln Ala Met Ala Leu Val Tyr His Ala Thr Gly Asp Glu Lys Tyr Ala
145                 150                 155                 160
Arg Glu Trp Val Tyr Gln Tyr Ser Asp Trp Ala Arg Lys Asn Pro Leu
                165                 170                 175
Gly Leu Ser Gln Asp Asn Asp Lys Phe Val Trp Arg Pro Leu Glu Val
            180                 185                 190
Ser Asp Arg Val Gln Ser Leu Pro Pro Thr Phe Ser Leu Phe Val Asn
        195                 200                 205
Ser Pro Ala Phe Thr Pro Ala Phe Leu Met Glu Phe Leu Asn Ser Tyr
    210                 215                 220
His Gln Gln Ala Asp Tyr Leu Ser Thr His Tyr Ala Glu Gln Gly Asn
225                 230                 235                 240
His Arg Leu Phe Glu Ala Gln Arg Asn Leu Phe Ala Gly Val Ser Phe
                245                 250                 255
Pro Glu Phe Lys Asp Ser Pro Arg Trp Arg Gln Thr Gly Ile Ser Val
            260                 265                 270
Leu Asn Thr Glu Ile Lys Lys Gln Val Tyr Ala Asp Gly Met Gln Phe
        275                 280                 285
Glu Leu Ser Pro Ile Tyr His Val Ala Ala Ile Asp Ile Phe Leu Lys
    290                 295                 300
Ala Tyr Gly Ser Ala Lys Arg Val Asn Leu Glu Lys Glu Phe Pro Gln
305                 310                 315                 320
Ser Tyr Val Gln Thr Val Glu Asn Met Ile Met Ala Leu Ile Ser Ile
                325                 330                 335
Ser Leu Pro Asp Tyr Asn Thr Pro Met Phe Gly Asp Ser Trp Ile Thr
            340                 345                 350
Asp Lys Asn Phe Arg Met Ala Gln Phe Ala Ser Trp Ala Arg Val Phe
        355                 360                 365
Pro Ala Asn Gln Ala Ile Lys Tyr Phe Ala Thr Asp Gly Lys Gln Gly
    370                 375                 380
Lys Ala Pro Asn Phe Leu Ser Lys Ala Leu Ser Asn Ala Gly Phe Tyr
385                 390                 395                 400
Thr Phe Arg Ser Gly Trp Asp Lys Asn Ala Thr Val Met Val Leu Lys
                405                 410                 415
Ala Ser Pro Pro Gly Glu Phe His Ala Gln Pro Asp Asn Gly Thr Phe
            420                 425                 430
Glu Leu Phe Ile Lys Gly Arg Asn Phe Thr Pro Asp Ala Gly Val Phe
        435                 440                 445
Val Tyr Ser Gly Asp Glu Ala Ile Met Lys Leu Arg Asn Trp Tyr Arg
    450                 455                 460
Gln Thr Arg Ile His Ser Thr Leu Thr Leu Asp Asn Gln Asn Met Val
465                 470                 475                 480
Ile Thr Lys Ala Arg Gln Asn Lys Trp Glu Thr Gly Asn Asn Leu Asp
                485                 490                 495
Val Leu Thr Tyr Thr Asn Pro Ser Tyr Pro Asn Leu Asp His Gln Arg
```

```
                  500             505             510
Ser Val Leu Phe Ile Asn Lys Lys Tyr Phe Leu Val Ile Asp Arg Ala
            515             520             525

Ile Gly Glu Ala Thr Gly Asn Leu Gly Val His Trp Gln Leu Lys Glu
        530             535             540

Asp Ser Asn Pro Val Phe Asp Lys Thr Lys Asn Arg Val Tyr Thr Thr
545             550             555             560

Tyr Arg Asp Gly Asn Asn Leu Met Ile Gln Ser Leu Asn Ala Asp Arg
                565             570             575

Thr Ser Leu Asn Glu Glu Gly Lys Val Ser Tyr Val Tyr Asn Lys
            580             585             590

Glu Leu Lys Arg Pro Ala Phe Val Phe Glu Lys Pro Lys Lys Asn Ala
        595             600             605

Gly Thr Gln Asn Phe Val Ser Ile Val Tyr Pro Tyr Asp Gly Gln Lys
    610             615             620

Ala Pro Glu Ile Ser Ile Arg Glu Asn Lys Gly Asn Asp Phe Glu Lys
625             630             635             640

Gly Lys Leu Asn Leu Thr Leu Thr Ile Asn Gly Lys Gln Gln Leu Val
                645             650             655

Leu Val Pro

<210> SEQ ID NO 23
<211> LENGTH: 6646
<212> TYPE: DNA
<213> ORGANISM: Artificial Sequence
<220> FEATURE:
<223> OTHER INFORMATION: plasmid

<400> SEQUENCE: 23
ccgacaccat cgaatggtgc aaaacctttc gcggtatggc atgatagcgc ccggaagaga      60
gtcaattcag gtggtgaat gtgaaaccag taacgttata cgatgtcgca gagtatgccg     120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc gccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa accaccctg gcgcccaata   1080 cgcaaaccgc ctctccccgc gcgttggccg attcattaat gcagctggca cgacaggttt   1140
```

-continued

```
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga   1440
attgtgagcg gataacaatt tcacacagga acagccagt ccgtttaggt gttttcacga    1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt ggtggctac    1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta aacaaagat ctgctgccga cccgccaaa aacctgggaa     1920
gagatcccgg cgctggataa agaactgaaa gcgaaggta gagcgcgct gatgttcaac     1980
ctgcaagaac cgtacttcac ctggccgctg attgctgctg acggggtta tgcgttcaag    2040
tatgaaaacg gcaagtacga cattaaagac gtgggcgtgg ataacgctgg cgcgaaagcg   2100
ggtctgacct tcctggttga cctgattaaa acaaacaca tgaatgcaga caccgattac    2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
ggatcctcta gagtcgacct gcaggcaagc ttggcactgg ccgtcgtttt acaacgtcgt   2760
gactgggaaa accctggcgt tacccaactt aatcgccttg cagcacatcc ccctttcgcc   2820
agctggcgta atagcgaaga ggcccgcacc gatcgccctt cccaacagtt gcgcagcctg   2880
aatggcgaat ggcagcttgg ctgttttggc ggatgagata agattttcag cctgatacag   2940
attaaatcag aacgcagaag cggtctgata aaacagaatt tgcctggcgg cagtagcgcg   3000
gtggtcccac ctgaccccat gccgaactca gaagtgaaac gccgtagcgc cgatggtagt   3060
gtggggtctc cccatgcgag agtagggaac tgccaggcat caaataaaac gaaaggctca   3120
gtcgaaagac tgggcctttc gttttatctg ttgtttgtcg gtgaacgctc tcctgagtag   3180
gacaaatccg ccgggagcgg atttgaacgt tgcgaagcaa cggcccggag ggtggcgggc   3240
aggacgcccg ccataaactg ccaggcatca aattaagcag aaggccatcc tgacggatgg   3300
ccttttttgcg tttctacaaa ctcttttttgt ttattttct aaatacattc aaatatgtat   3360
ccgctcatga caataaacc ctgataaatg cttcaataat attgaaaaag gaagagtatg    3420
agtattcaac atttccgtgt cgcccttatt cccttttttg cggcattttg ccttcctgtt   3480
tttgctcacc cagaaacgct ggtgaaagta aaagatgctg aagatcagtt gggtgcacga   3540
```

```
gtgggttaca tcgaactgga tctcaacagc ggtaagatcc ttgagagttt tcgccccgaa    3600
gaacgttctc caatgatgag cacttttaaa gttctgctat gtggcgcggt attatcccgt    3660
gttgacgccg ggcaagagca actcggtcgc cgcatacact attctcagaa tgacttggtt    3720
gagtactcac cagtcacaga aaagcatctt acgcatggca tgacagtaag agaattatgc    3780
agtgctgcca taaccatgag tgataacact gcggccaact tacttctgac aacgatcgga    3840
ggaccgaagg agctaaccgc ttttttgcac aacatggggg atcatgtaac tcgccttgat    3900
cgttgggaac cggagctgaa tgaagccata ccaaacgacg agcgtgacac cacgatgcct    3960
gtagcaatgg caacaacgtt gcgcaaacta ttaactggcg aactacttac tctagcttcc    4020
cggcaacaat taatagactg gatggaggcg gataaagttg caggaccact tctgcgctcg    4080
gcccttccgg ctggctggtt tattgctgat aaatctggag ccggtgagcg tgggtctcgc    4140
ggtatcattg cagcactggg gccagatggt aagccctccc gtatcgtagt tatctacacg    4200
acggggagtc aggcaactat ggatgaacga atagacaga tcgctgagat aggtgcctca    4260
ctgattaagc attggtaact gtcagaccaa gtttactcat atatacttta gattgattta    4320
ccccggttga taatcagaaa agccccaaaa acaggaagat tgtataagca aatatttaaa    4380
ttgtaaacgt taatattttg ttaaaattcg cgttaaattt ttgttaaatc agctcatttt    4440
ttaaccaata ggccgaaatc ggcaaaatcc cttataaatc aaaagaatag accgagatag    4500
ggttgagtgt tgttccagtt tggaacaaga gtccactatt aaagaacgtg gactccaacg    4560
tcaaagggcg aaaaaccgtc tatcagggcg atggcccact acgtgaacca tcacccaaat    4620 caagttttt ggggtcgagg tgccgtaaag cactaaatcg gaaccctaaa gggagccccc    4680
gatttagagc ttgacgggga agccggcga acgtggcgag aaaggaaggg aagaaagcga    4740
aaggagcggg cgctagggcg ctggcaagtg tagcggtcac gctgcgcgta accaccacac    4800
ccgccgcgct taatgcgccg ctacaggcg cgtaaaagga tctaggtgaa gatcctttt    4860 gataatctca tgaccaaaat cccttaacgt gagttttcgt tccactgagc gtcagacccc    4920
gtagaaaaga tcaaaggatc ttcttgagat ccttttttc tgcgcgtaat ctgctgcttg    4980
caaacaaaaa aaccaccgct accagcggtg gtttgtttgc cggatcaaga gctaccaact    5040
ctttttccga aggtaactgg cttcagcaga gcgcagatac caaatactgt ccttctagtg    5100
tagccgtagt taggccacca cttcaagaac tctgtagcac cgcctacata cctcgctctg    5160
ctaatcctgt taccagtggc tgctgccagt ggcgataagt cgtgtcttac cgggttggac    5220
tcaagacgat agttaccgga taaggcgcag cggtcgggct gaacggggg ttcgtgcaca    5280 cagcccagct tggagcgaac gacctacacc gaactgagat acctacagcg tgagctatga    5340
gaaagcgcca cgcttcccga agggagaaag gcggacaggt atccggtaag gcgcagggtc    5400
ggaacaggag agcgcacgag ggagcttcca ggggggaaacg cctggtatct ttatagtcct    5460
gtcgggtttc gccacctctg acttgagcgt cgatttttgt gatgctcgtc aggggggcgg    5520
agcctatgga aaaacgccag caacgcggcc ttttttacggt tcctggcctt tgctggcct    5580 tttgctcaca tgttctttcc tgcgttatcc cctgattctg tggataaccg tattaccgcc    5640
tttgagtgag ctgataccgc tcgccgcagc cgaacgaccg agcgcagcga gtcagtgagc    5700
gaggaagcgg aagagcgcct gatgcggtat tttctcctta cgcatctgtg cggtatttca    5760
caccgcatat atggtgcact ctcagtacaa tctgctctga tgccgcatag ttaagccagt    5820
atacactccg ctatcgctac gtgactgggt catggctgcg ccccgacacc cgccaacacc    5880
```

```
cgctgacgcg ccctgacggg cttgtctgct cccggcatcc gcttacagac aagctgtgac    5940
cgtctccggg agctgcatgt gtcagaggtt ttcaccgtca tcaccgaaac gcgcgaggca    6000
gctgcggtaa agctcatcag cgtggtcgtg cagcgattca cagatgtctg cctgttcatc    6060
cgcgtccagc tcgttgagtt tctccagaag cgttaatgtc tggcttctga taaagcgggc    6120
catgttaagg gcggttttt cctgtttggt cactgatgcc tccgtgtaag ggggatttct      6180
gttcatgggg gtaatgatac cgatgaaacg agagaggatg ctcacgatac gggttactga    6240
tgatgaacat gcccggttac tggaacgttg tgagggtaaa caactggcgg tatggatgcg    6300
gcgggaccag agaaaaatca ctcagggtca atgccagcgc ttcgttaata cagatgtagg    6360
tgttccacag ggtagccagc agcatcctgc gatgcagatc cggaacataa tggtgcaggg    6420
cgctgacttc cgcgttccca gactttacga aacacgaaaa ccgaagacca ttcatgttgt    6480
tgctcaggtc gcagacgttt tgcagcagca gtcgcttcac gttcgctcgc gtatcggtga    6540
ttcattctgc taaccagtaa ggcaaccccg ccagcctagc cgggtcctca acgacaggag    6600
cacgatcatg cgcacccgtg gccaggaccc aacgctgccc gaaatt                   6646

<210> SEQ ID NO 24
<211> LENGTH: 35
<212> TYPE: DNA
<213> ORGANISM: Artificial Sequence
<220> FEATURE:
<223> OTHER INFORMATION: primer

<400> SEQUENCE: 24
aagcttggca ctggccgtcg ttttacaacg tcgtg                               35

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
ggatccgaat tctgaaatcc ttccctcgat cccga                               35

<210> SEQ ID NO 26
<211> LENGTH: 6556
<212> TYPE: DNA
<213> ORGANISM: Artificial Sequence
<220> FEATURE:
<223> OTHER INFORMATION: plasmid

<400> SEQUENCE: 26
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
```

```
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg cgcccaata    1080 cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt ccgtttaggt gttttcacga    1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga cccgccaaa acctgggaa    1920 gagatcccgg cgctggataa agaactgaaa gcgaaaggta agagcgcgct gatgttcaac   1980
ctgcaagaac cgtacttcac ctggccgctg attgctgctg acgggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgccct taataaaggc gaaacagcg tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gcctagcgc tgaagtctta cgaggaagag    2460
ttggcgaaag atccacgtat tgccgccact atggaaaacg cccagaaagg tgaaatcatg   2520
ccgaacatcc gcagatgtc cgcttctgg tatgccgtgc gtactgcggt gatcaacgcc     2580
gccagcggtc gtcagactgt cgatgcagcc ctggcggccg cctcgagctc ggatccaagc   2640
ttggcactgg ccgtcgtttt acaacgtcgt gactgggaaa accctggcgt tacccaactt   2700
aatcgccttg cagcacatcc ccctttcgcc agctggcgta atagcgaaga ggcccgcacc   2760
gatcgccctt cccaacagtt gcgcagcctg aatggcgaat ggcagcttgg ctgttttggc   2820
ggatgagata gattttcag cctgatacag attaaatcag aacgcagaag cggtctgata    2880
aaacagaatt tgcctggcgg cagtagcgcg gtggtcccac ctgaccccat gccgaactca   2940
```

```
gaagtgaaac gccgtagcgc cgatggtagt gtggggtctc cccatgcgag agtagggaac    3000
tgccaggcat caaataaaac gaaaggctca gtcgaaagac tgggcctttc gttttatctg    3060
ttgtttgtcg gtgaacgctc tcctgagtag gacaaatccg ccgggagcgg atttgaacgt    3120
tgcgaagcaa cggcccggag ggtggcgggc aggacgcccg ccataaactg ccaggcatca    3180
aattaagcag aaggccatcc tgacggatgg ccttttttgcg tttctacaaa ctctttttgt    3240
ttatttttct aaatacattc aaatatgtat ccgctcatga gacaataacc ctgataaatg    3300
cttcaataat attgaaaaag gaagagtatg agtattcaac atttccgtgt cgcccttatt    3360
cccttttttg cggcattttg ccttcctgtt tttgctcacc cagaaacgct ggtgaaagta    3420
aaagatgctg aagatcagtt gggtgcacga gtgggttaca tcgaactgga tctcaacagc    3480
ggtaagatcc ttgagagttt tcgccccgaa gaacgttctc caatgatgag cacttttaaa    3540
gttctgctat gtggcgcggt attatcccgt gttgacgccg ggcaagagca actcggtcgc    3600
cgcatacact attctcagaa tgacttggtt gagtactcac cagtcacaga aaagcatctt    3660
acggatggca tgacagtaag agaattatgc agtgctgcca taaccatgag tgataacact    3720
gcggccaact tacttctgac aacgatcgga ggaccgaagg agctaaccgc ttttttgcac    3780
aacatggggg atcatgtaac tcgccttgat cgttgggaac cggagctgaa tgaagccata    3840
ccaaacgacg agcgtgacac cacgatgcct gtagcaatgg caacaacgtt gcgcaaacta    3900
ttaactggcg aactacttac tctagcttcc cggcaacaat aatagactg gatggaggcg    3960 gataaagttg caggaccact tctgcgctcg gcccttccgg ctggctggtt tattgctgat    4020
aaatctggag ccggtgagcg tgggtctcgc ggtatcattg cagcactggg gccagatggt    4080
aagccctccc gtatcgtagt tatctacacg acggggagtc aggcaactat ggatgaacga    4140
aatagacaga tcgctgagat aggtgcctca ctgattaagc attggtaact gtcagaccaa    4200
gtttactcat atatacttta gattgattta ccccggttga taatcagaaa agccccaaaa    4260
acaggaagat tgtataagca aatatttaaa ttgtaaacgt taatattttg ttaaaattcg    4320
cgttaaattt ttgttaaatc agctcatttt ttaaccaata ggccgaaatc ggcaaaatcc    4380
cttataaatc aaaagaatag accgagatag ggttgagtgt tgttccagtt tggaacaaga    4440
gtccactatt aaagaacgtg gactccaacg tcaaagggcg aaaaaccgtc tatcagggcg    4500
atggcccact acgtgaacca tcacccaaat caagtttttt ggggtcgagg tgccgtaaag    4560
cactaaatcg gaaccctaaa gggagccccc gatttagagc ttgacgggga aagccggcga    4620
acgtggcgag aaaggaaggg aagaaagcga aaggagcggg cgctagggcg ctggcaagtg    4680
tagcggtcac gctgcgcgta accaccacac ccgccgcgct taatgcgccg ctacagggcg    4740
cgtaaaagga tctaggtgaa gatcctttt gataatctca tgaccaaaat cccttaacgt    4800
gagttttcgt tccactgagc gtcagacccc gtagaaaaga tcaaaggatc ttcttgagat    4860 ccttttttc tgcgcgtaat ctgctgcttg caaacaaaaa aaccaccgct accagcggtg    4920
gtttgtttgc cggatcaaga gctaccaact cttttccga aggtaactgg cttcagcaga    4980
gcgcagatac caaatactgt ccttctagtg tagccgtagt taggccacca cttcaagaac    5040
tctgtagcac cgcctacata cctcgctctg ctaatcctgt taccagtggc tgctgccagt    5100
ggcgataagt cgtgtcttac cgggttggac tcaagacgat agttaccgga taaggcgcag    5160
cggtcgggct gaacggggggg ttcgtgcaca cagcccagct tggagcgaac gacctacacc    5220
gaactgagat acctacagcg tgagctatga gaaagcgcca cgcttcccga agggagaaag    5280
gcggacaggt atccggtaag cggcagggtc ggaacaggag agcgcacgag ggagcttcca    5340
```

-continued

```
gggggaaacg cctggtatct ttatagtcct gtcgggtttc gccacctctg acttgagcgt      5400
cgatttttgt gatgctcgtc agggggggcgg agcctatgga aaaacgccag caacgcggcc      5460
tttttacggt tcctggcctt ttgctggcct tttgctcaca tgttctttcc tgcgttatcc      5520
cctgattctg tggataaccg tattaccgcc tttgagtgag ctgataccgc tcgccgcagc      5580
cgaacgaccg agcgcagcga gtcagtgagc gaggaagcgg aagagcgcct gatgcggtat      5640
tttctcctta cgcatctgtg cggtatttca caccgcatat atggtgcact ctcagtacaa      5700
tctgctctga tgccgcatag ttaagccagt atacactccg ctatcgctac gtgactgggt      5760
catggctgcg ccccgacacc cgccaacacc cgctgacgcg ccctgacggg cttgtctgct      5820
cccggcatcc gcttacagac aagctgtgac cgtctccggg agctgcatgt gtcagaggtt      5880
ttcaccgtca tcaccgaaac gcgcgaggca gctgcggtaa agctcatcag cgtggtcgtg      5940
cagcgattca cagatgtctg cctgttcatc cgcgtccagc tcgttgagtt tctccagaag      6000
cgttaatgtc tggcttctga taaagcgggc catgttaagg gcggtttttt cctgtttggt      6060
cactgatgcc tccgtgtaag ggggatttct gttcatgggg gtaatgatac cgatgaaacg      6120
agagaggatg ctcacgatac gggttactga tgatgaacat gcccggttac tggaacgttg      6180
tgagggtaaa caactggcgg tatggatgcg gcgggaccag agaaaaatca ctcagggtca      6240
atgccagcgc ttcgttaata cagatgtagg tgttccacag ggtagccagc agcatcctgc      6300
gatgcagatc cggaacataa tggtgcaggg cgctgacttc cgcgtttcca gactttacga      6360
aacacgaaaa ccgaagacca ttcatgttgt tgctcaggtc gcagacgttt tgcagcagca      6420
gtcgcttcac gttcgctcgc gtatcggtga ttcattctgc taaccagtaa ggcaaccccg      6480
ccagcctagc cgggtcctca acgacaggag cacgatcatg cgcacccgtg gccaggaccc      6540
aacgctgccc gaaatt                                                      6556
```

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
tccagaagac gcggccgc                                                    18

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
ctcgagctcg gatccaagct tg                                               22

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
gccgcgtctt ctggaggcgt tcggtatgaa gaaatc                                36

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30
ggatccgagc tcgagttaat tatgctttgc gcgaccg                               37

<210> SEQ ID NO 31
<211> LENGTH: 1551
<212> TYPE: DNA
<213> ORGANISM: Danio rerio

<400> SEQUENCE: 31
ggcgttcggt atgaagaaat cgactgcttg attaacgacg atgcaaccat caaagggcgc      60
cgcgaaggct ctgaggtgta catgccgttt agctggatgg aaaagtattt cgaagtgtac     120
ggcaaagttg tgcaatacga tggctatgat cgctttgaat tctctcattc atacagcaaa     180
gtgtatgcgc agcgcgagca gtatcatccg aatggtgtct ttatgagctt tgaggggtat     240
aacgtagaag tgcgcgatcg tgtcaaatgt atctccggtg ttgaaggtgt tccgcttagc     300
acccagtggg gtccacaggg ctacttttat gcgattcaga ttgcccagta cggtctgtcg     360
cactattcga agaacttaac cgaacgtccg ccgcatgtgg aggtgtatga tacggcggaa     420
gaacgcgaca gtcgtagttc tgcctggacc gttccaaaag gatgctcact gacccgcgtt     480
tacgacaaaa cccgcgcgac aagcgtccgc gaatttagcg ctccggaaaa tagcgaagga     540
gttagcttac cacttggtaa caccaaagat ttcattatct cctttgacct gaaattcaca     600
agtaatgggt cagtctctgt gattttggag actactgaaa agggaccgcc gtttgtgatc     660
cactatgtca ccacgacgca gttgatcctt ctgaaagatc gtgacattac ctacgggatt     720
ggtccacgca cgacctggac aactgtaacc cgggatctgc tgacggactt acgcaaaggt     780
atcggcctta gcaacacgaa ggcagtaaaa gcaaccaaaa ccatgccgcg ccgtgtggta     840 aaaactggtcg tacatggcac gggtaccatt gacaacatca ccattagcac cacgtcccat     900
atggccgcct tttatgccgc gtctgattgg ttggtgcgca atcaggatga acgtggtggc     960
tggccgatta tggtcacccg caaattaggc gagggcttcc gtgccttgga accgggctgg    1020
tattccgcga tggcgcaggg ccaagcgatg tccactctgg tgcgtgccta tctcatgacg    1080
aaagacgatc gttatctgaa agcggcgctg cgtgcaactg gccctttttaa gctgccgtca    1140 gaacagcacg gagtgaaagc ggtgtttatg aacaaatacg attggtacga agagtatccg    1200
acaatcccta gttcctttgt cctgaacggt ttcatctatt cacttattgg cctgtttgat    1260
ctggcacaga ctgctggcga gaaactgggc cgtgatgcgg gtcagctcta cagcaagggg    1320
atggagtctc tgaaagttat gttaccgctc tacgatacag ggtcggggac catctatgat    1380
ctccgccact tcattctggg aacagctccc aatctggcac gttgggatta ccacaccacg    1440
catattaatc agctgcaact gctgggtact atcgataata gtccgatttt ccgcgactcg    1500
gtcaaacgct ggaaatcgta cctgaaaggc ggtcgcgcaa agcataatta a             1551

<210> SEQ ID NO 32
<211> LENGTH: 4
<212> TYPE: PRT
<213> ORGANISM: Danio rerio
<220> FEATURE:
<221> NAME/KEY: misc_feature

```
<222> LOCATION: (1)..(4)
<223> OTHER INFORMATION: Xaa can be any naturally occurring amino acid

<400> SEQUENCE: 32

Xaa Xaa Xaa Xaa
1

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
taactcgagc tcggatccaa g                                              21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
cgctgctgca ttagtctgcg                                                20

<210> SEQ ID NO 35
<211> LENGTH: 48
<212> TYPE: DNA
<213> ORGANISM: Artificial Sequence
<220> FEATURE:
<223> OTHER INFORMATION: primer

<400> SEQUENCE: 35
actaatgcag cagcggatga agaagaagat atcgtcatta tctataac                 48

<210> SEQ ID NO 36
<211> LENGTH: 43
<212> TYPE: DNA
<213> ORGANISM: Artificial Sequence
<220> FEATURE:
<223> OTHER INFORMATION: primer

<400> SEQUENCE: 36
tccgagctcg agttaattgc ttttcggata gattttttcg tag                      43

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
gttttatgaa tttgccaaag aacagtttca g                                   31

<210> SEQ ID NO 38
<211> LENGTH: 31
<212> TYPE: DNA
<213> ORGANISM: Artificial Sequence
<220> FEATURE:
<223> OTHER INFORMATION: primer

<400> SEQUENCE: 38
ctgaaactgt tctttggcaa attcataaaa c                                   31
```

<210> SEQ ID NO 39
<211> LENGTH: 31
<212> TYPE: DNA
<213> ORGANISM: Artificial Sequence
<220> FEATURE:
<223> OTHER INFORMATION: primer

<400> SEQUENCE: 39
gttttatgaa tttgcccgtg aacagtttca g                          31

<210> SEQ ID NO 40
<211> LENGTH: 31
<212> TYPE: DNA
<213> ORGANISM: Artificial Sequence
<220> FEATURE:
<223> OTHER INFORMATION: primer

<400> SEQUENCE: 40
ctgaaactgt tcacgggcaa attcataaaa c                          31

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
gatggtgatc tgtatgaact ggcccagaac ttc                        33

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
gaagttctgg gccagttcat acagatcacc atc                        33

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43
gatggtgatc tgtatgatct ggcccagaac ttc                        33

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
gaagttctgg gccagatcat acagatcacc atc                        33

<210> SEQ ID NO 45
<211> LENGTH: 29
<212> TYPE: DNA
<213> ORGANISM: Artificial Sequence
<220> FEATURE:

<223> OTHER INFORMATION: primer

<400> SEQUENCE: 45
cgtgcacatg caaaacgtga aaaagatgg                                29

<210> SEQ ID NO 46
<211> LENGTH: 29
<212> TYPE: DNA
<213> ORGANISM: Artificial Sequence
<220> FEATURE:
<223> OTHER INFORMATION: primer

<400> SEQUENCE: 46 ccatctttt cacgttttgc atgtgcacg                                 29

<210> SEQ ID NO 47
<211> LENGTH: 32
<212> TYPE: DNA
<213> ORGANISM: Artificial Sequence
<220> FEATURE:
<223> OTHER INFORMATION: primer

<400> SEQUENCE: 47
cgaccaaaca gaccgaagca aaactgcagc ag                            32

<210> SEQ ID NO 48
<211> LENGTH: 32
<212> TYPE: DNA
<213> ORGANISM: Artificial Sequence
<220> FEATURE:
<223> OTHER INFORMATION: primer

<400> SEQUENCE: 48
ctgctgcagt tttgcttcgg tctgtttggt cg                            32

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
cagcagagcg atattgcgaa aatggaaaac gag                           33

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
ctcgttttcc attttcgcaa tatcgctctg ctg                           33

<210> SEQ ID NO 51
<211> LENGTH: 33
<212> TYPE: DNA
<213> ORGANISM: Artificial Sequence
<220> FEATURE:
<223> OTHER INFORMATION: primer

<400> SEQUENCE: 51
cagcagagcg atattaacaa aatggaaaac gag                           33

<210> SEQ ID NO 52
<211> LENGTH: 33
<212> TYPE: DNA
<213> ORGANISM: Artificial Sequence
<220> FEATURE:
<223> OTHER INFORMATION: primer

<400> SEQUENCE: 52
ctcgttttcc attttgttaa tatcgctctg ctg                                33

<210> SEQ ID NO 53
<211> LENGTH: 29
<212> TYPE: DNA
<213> ORGANISM: Artificial Sequence
<220> FEATURE:
<223> OTHER INFORMATION: primer

<400> SEQUENCE: 53
aatggaaaac gagtttgctg aatttgccc                                    29

<210> SEQ ID NO 54
<211> LENGTH: 29
<212> TYPE: DNA
<213> ORGANISM: Artificial Sequence
<220> FEATURE:
<223> OTHER INFORMATION: primer

<400> SEQUENCE: 54
gggcaaattc agcaaactcg ttttccatt                                    29

<210> SEQ ID NO 55
<211> LENGTH: 33
<212> TYPE: DNA
<213> ORGANISM: Artificial Sequence
<220> FEATURE:
<223> OTHER INFORMATION: primer

<400> SEQUENCE: 55
ccgaaggtgg tagcgaatgt gcaccggaaa aac                                33

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56 gttttttccgg tgcacattcg ctaccacctt cgg                               33

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57
ctggtgggtg tgctggaaga actggaag                                     28

<210> SEQ ID NO 58
<211> LENGTH: 28
<212> TYPE: DNA
<213> ORGANISM: Artificial Sequence
<220> FEATURE:
<223> OTHER INFORMATION: primer

<400> SEQUENCE: 58
cttccagttc ttccagcaca cccaccag                                28

<210> SEQ ID NO 59
<211> LENGTH: 37
<212> TYPE: DNA
<213> ORGANISM: Artificial Sequence
<220> FEATURE:
<223> OTHER INFORMATION: primer

<400> SEQUENCE: 59
gatatttgga aaatggaata cgagttttat gaatttg                      37

<210> SEQ ID NO 60
<211> LENGTH: 37
<212> TYPE: DNA
<213> ORGANISM: Artificial Sequence
<220> FEATURE:
<223> OTHER INFORMATION: primer

<400> SEQUENCE: 60
caaattcata aaactcgtat tccatttcc aaatatc                       37

<210> SEQ ID NO 61
<211> LENGTH: 37
<212> TYPE: DNA
<213> ORGANISM: Artificial Sequence
<220> FEATURE:
<223> OTHER INFORMATION: primer

<400> SEQUENCE: 61
gatatttgga aaatggaacg cgagttttat gaatttg                      37

<210> SEQ ID NO 62
<211> LENGTH: 37
<212> TYPE: DNA
<213> ORGANISM: Artificial Sequence
<220> FEATURE:
<223> OTHER INFORMATION: primer

<400> SEQUENCE: 62
caaattcata aaactcgcgt tccatttcc aaatatc                       37

<210> SEQ ID NO 63
<211> LENGTH: 37
<212> TYPE: DNA
<213> ORGANISM: Artificial Sequence
<220> FEATURE:
<223> OTHER INFORMATION: primer

<400> SEQUENCE: 63
gatatttgga aaatggaaaa agagttttat gaatttg                      37

<210> SEQ ID NO 64
<211> LENGTH: 37
<212> TYPE: DNA
<213> ORGANISM: Artificial Sequence
<220> FEATURE:
<223> OTHER INFORMATION: primer

<400> SEQUENCE: 64
caaattcata aaactctttt tccatttcc aaatatc                       37

<210> SEQ ID NO 65
<211> LENGTH: 31

```
<212> TYPE: DNA
<213> ORGANISM: Artificial Sequence
<220> FEATURE:
<223> OTHER INFORMATION: primer

<400> SEQUENCE: 65
cggtgttcgt aaacatggca cccgtgcact g                                     31

<210> SEQ ID NO 66
<211> LENGTH: 31
<212> TYPE: DNA
<213> ORGANISM: Artificial Sequence
<220> FEATURE:
<223> OTHER INFORMATION: primer

<400> SEQUENCE: 66
cagtgcacgg gtgccatgtt tacgaacacc g                                     31

<210> SEQ ID NO 67
<211> LENGTH: 31
<212> TYPE: DNA
<213> ORGANISM: Artificial Sequence
<220> FEATURE:
<223> OTHER INFORMATION: primer

<400> SEQUENCE: 67
gtgcactgct ggaaaaactg agcctgcatc c                                     31

<210> SEQ ID NO 68
<211> LENGTH: 31
<212> TYPE: DNA
<213> ORGANISM: Artificial Sequence
<220> FEATURE:
<223> OTHER INFORMATION: primer

<400> SEQUENCE: 68
ggatgcaggc tcagttttc cagcagtgca c                                      31

<210> SEQ ID NO 69
<211> LENGTH: 31
<212> TYPE: DNA
<213> ORGANISM: Artificial Sequence
<220> FEATURE:
<223> OTHER INFORMATION: primer

<400> SEQUENCE: 69
gtgcactgct ggaatacctg agcctgcatc c                                     31

<210> SEQ ID NO 70
<211> LENGTH: 31
<212> TYPE: DNA
<213> ORGANISM: Artificial Sequence
<220> FEATURE:
<223> OTHER INFORMATION: primer

<400> SEQUENCE: 70
ggatgcaggc tcaggtattc cagcagtgca c                                     31

<210> SEQ ID NO 71
<211> LENGTH: 32
<212> TYPE: DNA
<213> ORGANISM: Artificial Sequence
<220> FEATURE:
<223> OTHER INFORMATION: primer

<400> SEQUENCE: 71
```
ctgaccgttg aaaaacgtcc ggcatatttc ac                                    32

<210> SEQ ID NO 72
<211> LENGTH: 32
<212> TYPE: DNA
<213> ORGANISM: Artificial Sequence
<220> FEATURE:
<223> OTHER INFORMATION: primer

<400> SEQUENCE: 72
gtgaaatatg ccggacgttt ttcaacggtc ag                                    32

<210> SEQ ID NO 73
<211> LENGTH: 32
<212> TYPE: DNA
<213> ORGANISM: Artificial Sequence
<220> FEATURE:
<223> OTHER INFORMATION: primer

<400> SEQUENCE: 73
ctgaccgttg aaaacaccc ggcatatttc ac                                     32

<210> SEQ ID NO 74
<211> LENGTH: 32
<212> TYPE: DNA
<213> ORGANISM: Artificial Sequence
<220> FEATURE:
<223> OTHER INFORMATION: primer

<400> SEQUENCE: 74
gtgaaatatg ccgggtgttt ttcaacggtc ag                                    32

<210> SEQ ID NO 75
<211> LENGTH: 32
<212> TYPE: DNA
<213> ORGANISM: Artificial Sequence
<220> FEATURE:
<223> OTHER INFORMATION: primer

<400> SEQUENCE: 75
ctgaccgttg aaaaaaaacc ggcatatttc ac                                    32

<210> SEQ ID NO 76
<211> LENGTH: 32
<212> TYPE: DNA
<213> ORGANISM: Artificial Sequence
<220> FEATURE:
<223> OTHER INFORMATION: primer

<400> SEQUENCE: 76
gtgaaatatg ccggtttttt ttcaacggtc ag                                    32

<210> SEQ ID NO 77
<211> LENGTH: 32
<212> TYPE: DNA
<213> ORGANISM: Artificial Sequence
<220> FEATURE:
<223> OTHER INFORMATION: primer

<400> SEQUENCE: 77
gcgattatac ccagcgtctg tataatcatc tg                                    32

<210> SEQ ID NO 78
<211> LENGTH: 32
<212> TYPE: DNA
<213> ORGANISM: Artificial Sequence

```
<220> FEATURE:
<223> OTHER INFORMATION: primer

<400> SEQUENCE: 78
cagatgatta tacagacgct gggtataatc gc                              32

<210> SEQ ID NO 79
<211> LENGTH: 30
<212> TYPE: DNA
<213> ORGANISM: Artificial Sequence
<220> FEATURE:
<223> OTHER INFORMATION: primer

<400> SEQUENCE: 79
cccaggttct gtatcatcat ctgcagaaac                                 30

<210> SEQ ID NO 80
<211> LENGTH: 30
<212> TYPE: DNA
<213> ORGANISM: Artificial Sequence
<220> FEATURE:
<223> OTHER INFORMATION: primer

<400> SEQUENCE: 80
gtttctgcag atgatgatac agaacctggg                                 30

<210> SEQ ID NO 81
<211> LENGTH: 31
<212> TYPE: DNA
<213> ORGANISM: Artificial Sequence
<220> FEATURE:
<223> OTHER INFORMATION: primer

<400> SEQUENCE: 81
ccgttgaaaa aacagcggca tatttcacca g                               31

<210> SEQ ID NO 82
<211> LENGTH: 31
<212> TYPE: DNA
<213> ORGANISM: Artificial Sequence
<220> FEATURE:
<223> OTHER INFORMATION: primer

<400> SEQUENCE: 82
ctggtgaaat atgccgctgt tttttcaacg g                               31

<210> SEQ ID NO 83
<211> LENGTH: 30
<212> TYPE: DNA
<213> ORGANISM: Artificial Sequence
<220> FEATURE:
<223> OTHER INFORMATION: primer

<400> SEQUENCE: 83
cccaggttct gtataaacat ctgcagaaac                                 30

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
gtttctgcag atgtttatac agaacctggg                                 30
```

```
<210> SEQ ID NO 85
<211> LENGTH: 30
<212> TYPE: DNA
<213> ORGANISM: Artificial Sequence
<220> FEATURE:
<223> OTHER INFORMATION: primer

<400> SEQUENCE: 85
cccgtgcact gctgcagatg ctgagcctgc                                    30

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
gcaggctcag catctgcagc agtgcacggg                                    30

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
cccgtgcact gctgaacatg ctgagcctgc                                    30

<210> SEQ ID NO 88
<211> LENGTH: 30
<212> TYPE: DNA
<213> ORGANISM: Artificial Sequence
<220> FEATURE:
<223> OTHER INFORMATION: primer

<400> SEQUENCE: 88
gcaggctcag catgttcagc agtgcacggg                                    30

<210> SEQ ID NO 89
<211> LENGTH: 34
<212> TYPE: DNA
<213> ORGANISM: Artificial Sequence
<220> FEATURE:
<223> OTHER INFORMATION: primer

<400> SEQUENCE: 89
gttgcagcag cagaacatga agtgcatttt tttg                               34

<210> SEQ ID NO 90
<211> LENGTH: 34
<212> TYPE: DNA
<213> ORGANISM: Artificial Sequence
<220> FEATURE:
<223> OTHER INFORMATION: primer

<400> SEQUENCE: 90
caaaaaaatg cacttcatgt tctgctgctg caac                               34

<210> SEQ ID NO 91
<211> LENGTH: 32
<212> TYPE: DNA
<213> ORGANISM: Artificial Sequence
<220> FEATURE:
<223> OTHER INFORMATION: primer
```

```
<400> SEQUENCE: 91
gtgcattttt ttgatttcga ggaacattat ag                                    32

<210> SEQ ID NO 92
<211> LENGTH: 32
<212> TYPE: DNA
<213> ORGANISM: Artificial Sequence
<220> FEATURE:
<223> OTHER INFORMATION: primer

<400> SEQUENCE: 92
ctataatgtt cctcgaaatc aaaaaaatgc ac                                    32

<210> SEQ ID NO 93
<211> LENGTH: 33
<212> TYPE: DNA
<213> ORGANISM: Artificial Sequence
<220> FEATURE:
<223> OTHER INFORMATION: primer

<400> SEQUENCE: 93
gtataatcat ctgcagcagc ataaaccgta tcc                                   33

<210> SEQ ID NO 94
<211> LENGTH: 33
<212> TYPE: DNA
<213> ORGANISM: Artificial Sequence
<220> FEATURE:
<223> OTHER INFORMATION: primer

<400> SEQUENCE: 94
ggatacggtt tatgctgctg cagatgatta tac                                   33

<210> SEQ ID NO 95
<211> LENGTH: 33
<212> TYPE: DNA
<213> ORGANISM: Artificial Sequence
<220> FEATURE:
<223> OTHER INFORMATION: primer

<400> SEQUENCE: 95
gtataatcat ctgcagaacc ataaaccgta tcc                                   33

<210> SEQ ID NO 96
<211> LENGTH: 33
<212> TYPE: DNA
<213> ORGANISM: Artificial Sequence
<220> FEATURE:
<223> OTHER INFORMATION: primer

<400> SEQUENCE: 96
ggatacggtt tatggttctg cagatgatta tac                                   33

<210> SEQ ID NO 97
<211> LENGTH: 33
<212> TYPE: DNA
<213> ORGANISM: Artificial Sequence
<220> FEATURE:
<223> OTHER INFORMATION: primer

<400> SEQUENCE: 97
caaaaccaaa ggcttctttt gcctgcgtga tag                                   33

<210> SEQ ID NO 98
```

```
<211> LENGTH: 33
<212> TYPE: DNA
<213> ORGANISM: Artificial Sequence
<220> FEATURE:
<223> OTHER INFORMATION: primer

<400> SEQUENCE: 98
ctatcacgca ggcaaaagaa gcctttggtt ttg                                   33

<210> SEQ ID NO 99
<211> LENGTH: 32
<212> TYPE: DNA
<213> ORGANISM: Artificial Sequence
<220> FEATURE:
<223> OTHER INFORMATION: primer

<400> SEQUENCE: 99
gcgattatac ccagattctg tataatcatc tg                                    32

<210> SEQ ID NO 100
<211> LENGTH: 32
<212> TYPE: DNA
<213> ORGANISM: Artificial Sequence
<220> FEATURE:
<223> OTHER INFORMATION: primer

<400> SEQUENCE: 100
cagatgatta tacagaatct gggtataatc gc                                    32

<210> SEQ ID NO 101
<211> LENGTH: 32
<212> TYPE: DNA
<213> ORGANISM: Artificial Sequence
<220> FEATURE:
<223> OTHER INFORMATION: primer

<400> SEQUENCE: 101
gatggtgatc gtctggttcg tgatccgttt cc                                    32

<210> SEQ ID NO 102
<211> LENGTH: 32
<212> TYPE: DNA
<213> ORGANISM: Artificial Sequence
<220> FEATURE:
<223> OTHER INFORMATION: primer

<400> SEQUENCE: 102
ggaaacggat cacgaaccag acgatcacca tc                                    32

<210> SEQ ID NO 103
<211> LENGTH: 31
<212> TYPE: DNA
<213> ORGANISM: Artificial Sequence
<220> FEATURE:
<223> OTHER INFORMATION: primer

<400> SEQUENCE: 103
gtctgaatct ggattttaaa gcactgaatc g                                     31

<210> SEQ ID NO 104
<211> LENGTH: 31
<212> TYPE: DNA
<213> ORGANISM: Artificial Sequence
<220> FEATURE:
<223> OTHER INFORMATION: primer

<400> SEQUENCE: 104
```
cgattcagtg ctttaaaatc cagattcaga c                                31

<210> SEQ ID NO 105
<211> LENGTH: 31
<212> TYPE: DNA
<213> ORGANISM: Artificial Sequence
<220> FEATURE:
<223> OTHER INFORMATION: primer

<400> SEQUENCE: 105
ccattattat cggtattcgt aaaggtggca c                                31

<210> SEQ ID NO 106
<211> LENGTH: 31
<212> TYPE: DNA
<213> ORGANISM: Artificial Sequence
<220> FEATURE:
<223> OTHER INFORMATION: primer

<400> SEQUENCE: 106
gtgccacctt tacgaatacc gataataatg g                                31

<210> SEQ ID NO 107
<211> LENGTH: 33
<212> TYPE: DNA
<213> ORGANISM: Artificial Sequence
<220> FEATURE:
<223> OTHER INFORMATION: primer

<400> SEQUENCE: 107
cattcgcctg ctgctggttc tgcgtgatcc gag                              33

<210> SEQ ID NO 108
<211> LENGTH: 33
<212> TYPE: DNA
<213> ORGANISM: Artificial Sequence
<220> FEATURE:
<223> OTHER INFORMATION: primer

<400> SEQUENCE: 108
ctcggatcac gcagaaccag cagcaggcga atg                              33

<210> SEQ ID NO 109
<211> LENGTH: 31
<212> TYPE: DNA
<213> ORGANISM: Artificial Sequence
<220> FEATURE:
<223> OTHER INFORMATION: primer

<400> SEQUENCE: 109
cagaaacata aaccgtttcc gcctattgaa g                                31

<210> SEQ ID NO 110
<211> LENGTH: 31
<212> TYPE: DNA
<213> ORGANISM: Artificial Sequence
<220> FEATURE:
<223> OTHER INFORMATION: primer

<400> SEQUENCE: 110
cttcaatagg cggaaacggt ttatgtttct g                                31

<210> SEQ ID NO 111
<211> LENGTH: 37
<212> TYPE: DNA

```
<213> ORGANISM: Artificial Sequence
<220> FEATURE:
<223> OTHER INFORMATION: primer

<400> SEQUENCE: 111
gattataccc aggttctgtt taatcatctg cagaaac                              37

<210> SEQ ID NO 112
<211> LENGTH: 37
<212> TYPE: DNA
<213> ORGANISM: Artificial Sequence
<220> FEATURE:
<223> OTHER INFORMATION: primer

<400> SEQUENCE: 112
gtttctgcag atgattaaac agaacctggg tataatc                              37

<210> SEQ ID NO 113
<211> LENGTH: 34
<212> TYPE: DNA
<213> ORGANISM: Artificial Sequence
<220> FEATURE:
<223> OTHER INFORMATION: primer

<400> SEQUENCE: 113
gaaaaaacac cggcattttt caccagcccg aaag                                 34

<210> SEQ ID NO 114
<211> LENGTH: 34
<212> TYPE: DNA
<213> ORGANISM: Artificial Sequence
<220> FEATURE:
<223> OTHER INFORMATION: primer

<400> SEQUENCE: 114
ctttcgggct ggtgaaaaat gccggtgttt tttc                                 34

<210> SEQ ID NO 115
<211> LENGTH: 29
<212> TYPE: DNA
<213> ORGANISM: Artificial Sequence
<220> FEATURE:
<223> OTHER INFORMATION: primer

<400> SEQUENCE: 115
gtgttctgag cgattttacc caggttctg                                       29

<210> SEQ ID NO 116
<211> LENGTH: 29
<212> TYPE: DNA
<213> ORGANISM: Artificial Sequence
<220> FEATURE:
<223> OTHER INFORMATION: primer

<400> SEQUENCE: 116
cagaacctgg gtaaaatcgc tcagaacac                                       29

<210> SEQ ID NO 117
<211> LENGTH: 33
<212> TYPE: DNA
<213> ORGANISM: Artificial Sequence
<220> FEATURE:
<223> OTHER INFORMATION: primer

<400> SEQUENCE: 117
gattaatgcc agcaactact attttaacaa aac                                  33
```

<210> SEQ ID NO 118
<211> LENGTH: 33
<212> TYPE: DNA
<213> ORGANISM: Artificial Sequence
<220> FEATURE:
<223> OTHER INFORMATION: primer

<400> SEQUENCE: 118
gttttgttaa aatagtagtt gctggcatta atc                                    33

<210> SEQ ID NO 119
<211> LENGTH: 31
<212> TYPE: DNA
<213> ORGANISM: Artificial Sequence
<220> FEATURE:
<223> OTHER INFORMATION: primer

<400> SEQUENCE: 119
gtgcactgct ggaactgctg agcctgcatc c                                      31

<210> SEQ ID NO 120
<211> LENGTH: 31
<212> TYPE: DNA
<213> ORGANISM: Artificial Sequence
<220> FEATURE:
<223> OTHER INFORMATION: primer

<400> SEQUENCE: 120
ggatgcaggc tcagcagttc cagcagtgca c                                      31

<210> SEQ ID NO 121
<211> LENGTH: 34
<212> TYPE: DNA
<213> ORGANISM: Artificial Sequence
<220> FEATURE:
<223> OTHER INFORMATION: primer

<400> SEQUENCE: 121
ctattttaac aaaacccgtg gcttctattg cctg                                   34

<210> SEQ ID NO 122
<211> LENGTH: 34
<212> TYPE: DNA
<213> ORGANISM: Artificial Sequence
<220> FEATURE:
<223> OTHER INFORMATION: primer

<400> SEQUENCE: 122
caggcaatag aagccacggg ttttgttaaa atag                                   34

<210> SEQ ID NO 123
<211> LENGTH: 32
<212> TYPE: DNA
<213> ORGANISM: Artificial Sequence
<220> FEATURE:
<223> OTHER INFORMATION: primer

<400> SEQUENCE: 123
gatggtgatc gtctgctgcg tgatccgttt cc                                     32

<210> SEQ ID NO 124
<211> LENGTH: 32
<212> TYPE: DNA
<213> ORGANISM: Artificial Sequence
<220> FEATURE:

<223> OTHER INFORMATION: primer

<400> SEQUENCE: 124
ggaaacggat cacgcagcag acgatcacca tc                                32

<210> SEQ ID NO 125
<211> LENGTH: 32
<212> TYPE: DNA
<213> ORGANISM: Artificial Sequence
<220> FEATURE:
<223> OTHER INFORMATION: primer

<400> SEQUENCE: 125
ctgaatctgg attatcgtgc actgaatcgt ag                                32

<210> SEQ ID NO 126
<211> LENGTH: 32
<212> TYPE: DNA
<213> ORGANISM: Artificial Sequence
<220> FEATURE:
<223> OTHER INFORMATION: primer

<400> SEQUENCE: 126
ctacgattca gtgcacgata atccagattc ag                                32

<210> SEQ ID NO 127
<211> LENGTH: 33
<212> TYPE: DNA
<213> ORGANISM: Artificial Sequence
<220> FEATURE:
<223> OTHER INFORMATION: primer

<400> SEQUENCE: 127
cattcgcctg ctgctgctgc tgcgtgatcc gag                               33

<210> SEQ ID NO 128
<211> LENGTH: 33
<212> TYPE: DNA
<213> ORGANISM: Artificial Sequence
<220> FEATURE:
<223> OTHER INFORMATION: primer

<400> SEQUENCE: 128
ctcggatcac gcagcagcag cagcaggcga atg                               33

<210> SEQ ID NO 129
<211> LENGTH: 33
<212> TYPE: DNA
<213> ORGANISM: Artificial Sequence
<220> FEATURE:
<223> OTHER INFORMATION: primer

<400> SEQUENCE: 129
gaacgtgttc tgagcgaata cccaggtt ctg                                 33

<210> SEQ ID NO 130
<211> LENGTH: 33
<212> TYPE: DNA
<213> ORGANISM: Artificial Sequence
<220> FEATURE:
<223> OTHER INFORMATION: primer

<400> SEQUENCE: 130
cagaacctgg gtatattcgc tcagaacacg ttc                               33

```
<210> SEQ ID NO 131
<211> LENGTH: 36
<212> TYPE: DNA
<213> ORGANISM: Artificial Sequence
<220> FEATURE:
<223> OTHER INFORMATION: primer

<400> SEQUENCE: 131
gatgttgcag cagcagacaa tgaagtgcat tttttt                              36

<210> SEQ ID NO 132
<211> LENGTH: 36
<212> TYPE: DNA
<213> ORGANISM: Artificial Sequence
<220> FEATURE:
<223> OTHER INFORMATION: primer

<400> SEQUENCE: 132
aaaaaaatgc acttcattgt ctgctgctgc aacatc                              36

<210> SEQ ID NO 133
<211> LENGTH: 31
<212> TYPE: DNA
<213> ORGANISM: Artificial Sequence
<220> FEATURE:
<223> OTHER INFORMATION: primer

<400> SEQUENCE: 133
ctgcgtgatc cgagcgaccg tgttctgagc g                                   31

<210> SEQ ID NO 134
<211> LENGTH: 31
<212> TYPE: DNA
<213> ORGANISM: Artificial Sequence
<220> FEATURE:
<223> OTHER INFORMATION: primer

<400> SEQUENCE: 134
cgctcagaac acggtcgctc ggatcacgca g                                   31

<210> SEQ ID NO 135
<211> LENGTH: 32
<212> TYPE: DNA
<213> ORGANISM: Artificial Sequence
<220> FEATURE:
<223> OTHER INFORMATION: primer

<400> SEQUENCE: 135
gatcgttgtc tgcatgacag caaaggtcgt gc                                  32

<210> SEQ ID NO 136
<211> LENGTH: 32
<212> TYPE: DNA
<213> ORGANISM: Artificial Sequence
<220> FEATURE:
<223> OTHER INFORMATION: primer

<400> SEQUENCE: 136
gcacgacctt tgctgtcatg cagacaacga tc                                  32

<210> SEQ ID NO 137
<211> LENGTH: 30
<212> TYPE: DNA
<213> ORGANISM: Artificial Sequence
<220> FEATURE:
<223> OTHER INFORMATION: primer
```

```
<400> SEQUENCE: 137
cccgtgcact gctggacatg ctgagcctgc                                    30

<210> SEQ ID NO 138
<211> LENGTH: 30
<212> TYPE: DNA
<213> ORGANISM: Artificial Sequence
<220> FEATURE:
<223> OTHER INFORMATION: primer

<400> SEQUENCE: 138
gcaggctcag catgtccagc agtgcacggg                                    30
```

US 11,851,688 B2

2-O-SULFATION ENZYME MUTANT AND 3-O-SULFATION ENZYME MUTANT, AND METHOD FOR USING SAME

This application is a continuation of, and claims priority under 35 U.S.C. § 120 to, International Application No. PCT/JP2018/033897, filed Sep. 5, 2018, and claims priority therethrough under 35 U.S.C. § 119 to Japanese Patent Application No. 2017-170637, filed Sep. 5, 2017, the entireties of which are incorporated by reference herein. Also, the Sequence Listing filed electronically herewith is hereby incorporated by reference (File name: 2020-02-20T_US-605_Seq_List; File size: 72 KB; Date recorded: Feb. 19, 2020).

BACKGROUND

Technical Field

The present invention relates to a 2-O-sulfation enzyme mutant and a 3-O-sulfation enzyme mutant, and a method for using the same.

Background Art

Heparin is a kind of heparan sulfate and is a compound having an anticoagulant activity. Quality control is a problem in the manufacturing of animal-derived heparin, and therefore the development of manufacturing quality-controlled non-animal-derived heparin has been investigated. Examples of methods of producing non-animal-derived heparin include, for example, a method of producing heparin by subjecting heparosan produced using a microorganism to a reaction, such as sulfation and isomerization, etc. (see Patent Literatures 1 and 2, and Non-Patent Literatures 1 to 3).

Heparosan is known as a preferred raw material for manufacturing heparin. Heparosan is a polysaccharide made up of a repeating disaccharide unit composed of a β-D-glucuronic acid (GlcA) residue and an N-acetyl-α-D-glucosamine (GlcNAc) residue [→4)-β-D-GlcA-(1→4)-α-D-GlcNAc-(1→].

The method of producing heparin from heparosan is known to require a series of mutually interchangeable reactions including (1) N-deacetylation of α-D-glucosamine residue, (2) depolymerization, (3) N-sulfation of α-D-glucosamine residue, (4) C5-epimerization of hexuronic acid residue (namely, isomerization of a β-D-glucuronic acid residue into an α-L-iduronic acid residue), (5) 2-O-sulfation of hexuronic acid residue (preferably an α-L-iduronic acid residue), (6) 6-O-sulfation of α-D-glucosamine residue, and (7) 3-O-sulfation of α-D-glucosamine residue (see Patent Literatures 1 and 3 to 5).

Among these reactions, with respect to an enzyme (2-OST) catalyzing the reaction of 2-O-sulfation, a few findings have been reported. For example, in the analysis using chicken-derived 2-OST, it is reported that the trimer is an active form; that the polymer (non-trimer) aggregated in the purified enzyme is existent; and that the mutation of valine at the 332 position reduces the trimer ratio (activator rate) (Non-Patent Literature 4). But, with respect to 2-OST, neither an improvement of the trimer ratio nor a mutant whose activity has been improved thereby is reported.

In addition, with respect to an enzyme (3-OST) catalyzing the reaction of 3-O-sulfation, a few findings have also been reported. For example, with respect to 3-OST-1 as an isoform of mouse-derived 3-OST, there are reported a crystal structure (Non-Patent Literature 5), E90Q mutant and R276A mutant (Non-Patent Literature 6), and various mutants, such as E76A mutant, E76Q mutant, K123A mutant, Q163A mutant, H271 mutant, etc. (Non-Patent Literature 7). However, with respect to 3-OST, mutants having improved activities have not been substantially reported. For example, in Non-Patent Literature 7, it is only described that only the H271A mutant has a slightly high specific activity with 109% as compared with wild-type enzymes.

REFERENCES

Patent Literatures

Patent Literature 1: U.S. Pat. No. 8,227,449
Patent Literature 2: U.S. Patent Application Publication No. 2012/0322114
Patent Literature 3: WO 2017/115674
Patent Literature 4: WO 2017/115675
Patent Literature 5: U.S. Patent Application Publication No. 2012/0322114

Non-Patent Literatures

Non-Patent Literature 1: Lindahl U, et al., (2005) *J Med Chem*, 48(2): 349-352
Non-Patent Literature 2: Zhang Z., et al., (2008) *Journal of the American Chemical Society*, 130(39): 12998-13007
Non-Patent Literature 3: Chen J, et al., (2005) *J Biol Chem.*, 280(52): 42817-25
Non-Patent Literature 4: Bethea H N, et al., (2008) *Proc Natl Acad Sci USA*, 105(48): 18724-9
Non-Patent Literature 5: Moon, et al., (2012) *Proc Natl Acad Sci USA*, 109(14): 5265-70
Non-Patent Literature 6: Munoz, et al., (2006) *Biochemistry*, 45: 5122-28
Non-Patent Literature 7: Edavettal, et al., (2004) *J BIOL CHEM.*, 279(24): 25789-97

SUMMARY

A first aspect of the present invention is to provide a 2-OST mutant exhibiting a high activity, and a method of 2-O-sulfation using the 2-OST mutant.

A second aspect of the present invention is to provide a 3-OST mutant exhibiting a high activity, and a method of 3-O-sulfation using the 3-OST mutant.

A third aspect of the present invention is to provide a method of producing a heparan sulfate such as heparin utilizing the above-described sulfation method.

A 2-OST mutant having a substitution of a leucine residue at position 321 with a basic amino acid residue has been found that exhibits a high activity due to an improvement of the trimer ratio. A 3-OST-1 mutant having a substitution of an amino acid residue at position 77, position 125, or position 164 with a specific amino acid residue has been found to exhibit a high activity. Therefore, efficient methods of 2-O- and 3-O-sulfations and a method of producing a heparan sulfate utilizing such methods of sulfations are described herein.

It is an aspect of the present invention to provide a 2-O-sulfation enzyme mutant comprising I) an amino acid sequence selected from the group consisting of: (a) the amino acid sequence of SEQ ID NO: 2; (b) an amino acid sequence comprising one or several amino acid substitutions, deletions, insertions, or additions in the amino acid sequence of SEQ ID NO: 2; (c) an amino acid sequence having 90% or more identity to the amino acid sequence of SEQ ID NO: 2; (d) the amino acid sequence consisting of amino acid residues at positions 69 to 356 in the amino acid sequence of SEQ ID NO: 2; (e) an amino acid sequence comprising one or several amino acid substitutions, deletions, insertions, or additions in the amino acid sequence consisting of amino acid residues at positions 69 to 356 in the amino acid sequence of SEQ ID NO: 2; and (f) an amino acid sequence having 90% or more identity to the amino acid sequence consisting of amino acid residues at positions 69 to 356 in the amino acid sequence of SEQ ID NO: 2; II) a substitution of a leucine residue at position 321, relative to the amino acid sequence of SEQ ID NO: 2, with a basic amino acid residue; and III) a 2-O-sulfate transfer activity.

It is another aspect of the present invention to provide the 2-O-sulfation enzyme mutant as described above, wherein the basic amino acid residue is an arginine residue or a lysine residue.

It is another aspect of the present invention to provide a method of producing a modified heparosan compound in which a hydroxyl group at 2-position of a hexuronic acid residue is sulfated, comprising converting a heparosan compound into a modified heparosan compound comprising a hydroxyl group at 2-position of a hexuronic acid residue that has been sulfated in the presence of a 2-O-sulfation enzyme mutant, wherein the 2-O-sulfation enzyme mutant comprises: I) an amino acid sequence selected from the group consisting of of: (a) the amino acid sequence of SEQ ID NO: 2; (b) an amino acid sequence comprising one or several amino acid substitutions, deletions, insertions, or additions in the amino acid sequence of SEQ ID NO: 2; (c) an amino acid sequence having 90% or more identity to the amino acid sequence of SEQ ID NO: 2; (d) the amino acid sequence consisting of amino acid residues at positions 69 to 356 in the amino acid sequence of SEQ ID NO: 2; (e) an amino acid sequence comprising one or several amino acid substitutions, deletions, insertions, or additions in the amino acid sequence consisting of amino acid residues at positions 69 to 356 in the amino acid sequence of SEQ ID NO: 2; and (f) an amino acid sequence having 90% or more identity to the amino acid sequence consisting of amino acid residues at positions 69 to 356 in the amino acid sequence of SEQ ID NO: 2; II) a substitution of a leucine residue at position 321, relative to the amino acid sequence of SEQ ID NO: 2, with a basic amino acid residue; and III) a 2-O-sulfate transfer activity.

It is a further aspect of the present invention to provide the method as described above, wherein the heparosan compound is selected from the group consisting of: N-sulfated heparosan, N-sulfated epimerized heparosan, N-sulfated depolymerized heparosan, and N-sulfated epimerized depolymerized heparosan.

It is a further aspect of the present invention to provide the method as described above, wherein the 2-O-sulfation enzyme mutant is produced by a transformed microorganism or an extract thereof.

It is a further aspect of the present invention to provide the method as described above, wherein the transformed microorganism is a bacterium belonging to the genus *Escherichia*.

It is a further aspect of the present invention to provide the method as described above, wherein the bacterium belonging to the genus *Escherichia* is *Escherichia coli*.

It is a further aspect of the present invention to provide a 3-O-sulfation enzyme mutant comprising an amino acid sequence selected from the group consisting of: (a') the amino acid sequence of SEQ ID NO: 8; (b') an amino acid sequence comprising one or several amino acid substitutions, deletions, insertions, or additions in the amino acid sequence of SEQ ID NO: 8; (c') an amino acid sequence having 90% or more identity to the amino acid sequence of SEQ ID NO: 8; (d') the amino acid sequence consisting of amino acid residues at positions 48 to 311 in the amino acid sequence of SEQ ID NO: 8; (e') an amino acid sequence comprising one or several amino acid substitutions, deletions, insertions, or additions in the amino acid sequence consisting of amino acid residues at positions 48 to 311 in the amino acid sequence of SEQ ID NO: 8; and (f) an amino acid sequence having 90% or more identity to the amino acid sequence consisting of amino acid residues at positions 48 to 311 in the amino acid sequence of SEQ ID NO: 8; and wherein the 3-O-sulfation enzyme mutant has a substitution, relative to the amino acid sequence of SEQ ID NO: 8, selected from the group consisting of: (i) a methionine residue at position 77 is substituted with a lysine residue; (ii) a tryptophan residue at position 96 is substituted with a phenylalanine residue; (iii) a proline residue at position 125 is substituted with an alanine residue; (iv) a valine residue at position 164 is substituted with an isoleucine residue; (v) an asparagine residue at position 167 is substituted with a histidine residue; (vi) a lysine residue at position 171 is substituted with a glutamine residues; and (vii) a tyrosine residue at position 259 is substituted with a phenylalanine residue; wherein the 3-O-sulfation enzyme mutant has a 3-O-sulfate transfer activity.

It is a further aspect of the present invention to provide a method of producing a modified heparosan compound in which a hydroxyl group at 3-position of an α-D-glucosamine residue is sulfated, comprising converting a heparosan compound into a modified heparosan compound comprising a hydroxyl group at 3-position of an α-D-glucosamine residue that has been sulfated in the presence of a 3-O-sulfation enzyme mutant, wherein the 3-O-sulfation enzyme mutant an amino acid sequence selected from the group consisting of: (a') the amino acid sequence of SEQ ID NO: 8; (b') an amino acid sequence comprising one or several amino acid substitutions, deletions, insertions, or additions in the amino acid sequence of SEQ ID NO: 8; (c') an amino acid sequence having 90% or more identity to the amino acid sequence of SEQ ID NO: 8; (d') the amino acid sequence consisting of amino acid residues at positions 48 to 311 in the amino acid sequence of SEQ ID NO: 8; (e') an amino acid sequence comprising one or several amino acid substitutions, deletions, insertions, or additions in the amino acid sequence consisting of amino acid residues at positions 48 to 311 in the amino acid sequence of SEQ ID NO: 8; and (f) an amino acid sequence having 90% or more identity to the amino acid sequence consisting of amino acid residues at positions 48 to 311 in the amino acid sequence of SEQ ID NO: 8; and wherein the 3-O-sulfation enzyme mutant has a substitution, relative to the amino acid sequence of SEQ ID NO: 8, selected from the group consisting of: (i) a methionine residue at position 77 is substituted with a lysine residue; (ii) a tryptophan residue at position 96 is substituted with a phenylalanine residue; (iii) a proline residue at position 125 is substituted with an alanine residue; (iv) a valine residue at position 164 is substituted with an isoleucine residue; (v) an asparagine residue at position 167 is substituted with a histidine residue; (vi) a lysine residue at position 171 is substituted with a glutamine residues; and (vii) a tyrosine residue at position 259 is substituted with a phenylalanine residue; and wherein the 3-O-sulfation enzyme mutant has a 3-O-sulfate transfer activity.

It is a further aspect of the present invention to provide the method as described above, wherein the heparosan compound is selected from the group consisting of: N-sulfated 6-O-sulfated heparosan, N-sulfated 6-O-sulfated epimerized heparosan, N-sulfated 2-O-sulfated 6-O-sulfated heparosan, N-sulfated 2-O-sulfated 6-O-sulfated epimerized depolymerized heparosan, N-sulfated 6-O-sulfated depolymerized heparosan, N-sulfated 6-O-sulfated epimerized depolymerized heparosan, N-sulfated 2-O-sulfated 6-O-sulfated depolymerized heparosan, and N-sulfated 2-O-sulfated 6-O-sulfated epimerized depolymerized heparosan.

It is a further aspect of the present invention to provide the method as described above, wherein the 3-O-sulfation enzyme mutant is produced by a transformed microorganism or an extract thereof.

It is a further aspect of the present invention to provide the method as described above, wherein the transformed microorganism is a bacterium belonging to the genus *Escherichia*.

It is a further aspect of the present invention to provide the method as described above, wherein the bacterium belonging to the genus *Escherichia* is *Escherichia* col.

It is a further aspect of the present invention to provide a method of producing a heparan sulfate, comprising subjecting heparosan to a treatment comprising (1) N-deacetylation of α-D-glucosamine residue, (2) depolymerization, (3) N-sulfation of α-D-glucosamine residue, (4) C5-epimerization of hexuronic acid residue, (5) 2-O-sulfation of hexuronic acid residue, (6) 6-O-sulfation of α-D-glucosamine residue, and (7) 3-O-sulfation of α-D-glucosamine residue to produce a heparan sulfate, wherein: (I) the 2-O-sulfation of the hexuronic acid residue is performed in the presence of a 2-O-sulfation enzyme mutant comprising an amino acid sequence selected from the group consisting of: (a) the amino acid sequence of SEQ ID NO: 2; (b) an amino acid sequence comprising one or several amino acid substitutions, deletions, insertions, or additions in the amino acid sequence of SEQ ID NO: 2; (c) an amino acid sequence having 90% or more identity to the amino acid sequence of SEQ ID NO: 2; (d) the amino acid sequence consisting of amino acid residues at positions 69 to 356 in the amino acid sequence of SEQ ID NO: 2; (e) an amino acid sequence comprising one or several amino acid substitutions, deletions, insertions, or additions in the amino acid sequence consisting of amino acid residues at positions 69 to 356 in the amino acid sequence of SEQ ID NO: 2; and (f) an amino acid sequence having 90% or more identity to the amino acid sequence consisting of amino acid residues at positions 69 to 356 in the amino acid sequence of SEQ ID NO: 2; and wherein said 2-O-sulfation enzyme mutant comprises a substitution of a leucine residue at position 321, relative to the amino acid sequence in SEQ ID NO: 2, with a basic amino acid residue, and has a 2-O-sulfate transfer activity; or (II) the 3-O-sulfation of the α-D-glucosamine residue is performed in the presence of a 3-O-sulfation enzyme mutant comprising an amino acid sequence selected from the group consisting of: (a') the amino acid sequence of SEQ ID NO: 8; (b') an amino acid sequence comprising one or several amino acid substitutions, deletions, insertions, or additions in the amino acid sequence of SEQ ID NO: 8; (c') an amino acid sequence having 90% or more identity to the amino acid sequence of SEQ ID NO: 8; (d') the amino acid sequence consisting of amino acid residues at positions 48 to 311 in the amino acid sequence of SEQ ID NO: 8; (e') an amino acid sequence comprising one or several amino acid substitutions, deletions, insertions, or additions in the amino acid sequence consisting of amino acid residues at positions 48 to 311 in the amino acid sequence of SEQ ID NO: 8; and (f) an amino acid sequence having 90% or more identity to the amino acid sequence consisting of amino acid residues at positions 48 to 311 in the amino acid sequence of SEQ ID NO: 8; wherein the 3-O-sulfation enzyme mutant has a substitution, relative to the amino acid sequence of SEQ ID NO: 8, selected from the group consisting of: (i) a methionine residue at position 77 is substituted with a lysine residue; (ii) a tryptophan residue at position 96 is substituted with a phenylalanine residue; (iii) a proline residue at position 125 is substituted with an alanine residue; (iv) a valine residue at position 164 is substituted with an isoleucine residue; (v) an asparagine residue at position 167 is substituted with a histidine residue; (vi) a lysine residue at position 171 is substituted with a glutamine residues; and (vii) a tyrosine residue at position 259 is substituted with a phenylalanine residue; wherein the 3-O-sulfation enzyme mutant has a 3-O-sulfate transfer activity.

In view of the fact that the 2-O-sulfation enzyme mutant and the 3-O-sulfation enzyme mutant as described herein exhibit a high activity, they can be suitably employed in methods for producing objective substances.

According to the method as described herein using the mutant as described herein, the objective substances can be efficiently produced.

BRIEF DESCRIPTION OF THE DRAWING

FIG. 1 shows an example of a method of producing heparin from heparosan (e.g., WO/2017/115674A, WO/2017/115675A).

DETAILED DESCRIPTION

1. Mutant
2-O-Sulfation Enzyme Mutant:

A 2-O-sulfation enzyme mutant is described herein, wherein the mutant has a substitution of a leucine residue at position 321 with a basic amino acid residue. The 2-O-sulfation mutant can have an amino acid sequence selected from any of the following (a) to (f): (a) the amino acid sequence of SEQ ID NO: 2; (b) an amino acid sequence including one or several amino acid substitutions, deletions, insertions, or additions in the amino acid sequence of SEQ ID NO: 2; (c) an amino acid sequence having 90% or more identity to the amino acid sequence of SEQ ID NO: 2; (d) the amino acid sequence consisting of amino acid residues at positions 69 to 356 in the amino acid sequence of SEQ ID NO: 2; (e) an amino acid sequence including one or several amino acid substitutions, deletions, insertions, or additions in the amino acid sequence consisting of amino acid residues at positions 69 to 356 in the amino acid sequence of SEQ ID NO: 2; or (f) an amino acid sequence having 90% or more identity to the amino acid sequence consisting of amino acid residues at positions 69 to 356 in the amino acid sequence of SEQ ID NO: 2; and wherein the mutant has a 2-O-sulfate transfer activity.

The amino acid sequence as set forth above in (a) to (c) are specified by SEQ ID NO: 2, which corresponds to the full-length amino acid sequence of the Chinese hamster-derived 2-O-sulfation enzyme (2-OST). The amino acid sequences set forth above in (d) to (f) are specified by the catalytic sites of the Chinese hamster-derived 2-OST (Asp69-Asn356 in SEQ ID NO: 2).

The basic amino acid residue substituted at residue 321 in place of the leucine residue is an arginine residue, a lysine residue, or a histidine residue. An arginine residue or a lysine residue are particular examples. An arginine residue is another particular example.

The amino acid sequence set forth in above in (b), (c), (e), and (f) may have a further desired mutation at a predetermined site. For example, it has been reported that with respect to 2-OST, when the tyrosine residue at position 94 in the amino acid sequence of SEQ ID NO: 2 is substituted with an alanine residue, an isoleucine residue, a glycine residue, a phenylalanine residue, or a glutamic acid residue, the hydroxyl group at the 2-position of the α-L-iduronic acid residue (hexuronic acid residue) can be sulfated more preferentially, namely a change of substrate specificity, than the β-D-glucuronic acid residue (hexuronic acid residue) (Li K., et al., (2010) *J Biol Chem,* 285(15): 11106-11113). The substitution of the leucine residue at position 321 with a basic amino acid residue is one which improves the activity due to an improvement of the trimer ratio and is a mutation which does not affect the substrate specificity. As a consequence, the 2-O-sulfation enzyme mutant as described herein can further have such a mutation in addition to the substitution of the leucine residue at position 321 with the basic amino acid residue. The term "2-O-sulfate transfer activity" refers to an activity of transferring a sulfate group from a sulfate group donor (e.g., 3'-phosphoadenosine-5'-phosphosulfate (PAPS)) toward a hydroxyl group at the 2-position of the hexuronic acid residue, thereby producing a structure of "—O-sulfate group" at the 2-position of the hexuronic acid residue. Examples of the hexuronic acid residue include an α-L-iduronic acid residue and a β-D-iduronic acid residue. An α-L-iduronic acid residue is a particular example.

The evaluation of the 2-O-sulfate transfer activity can be suitably performed. For example, as described in the Examples, the 2-O-sulfate transfer activity may be evaluated by measuring the 2-O-sulfate transfer activity and subsequently determining a 2-O-sulfation rate through disaccharide composition analysis. More specifically, the 2-O-sulfate transfer activity can be measured by adding 1.9% of a mutant-containing liquid to a reaction liquid (2 mg/mL of a heparosan compound (substrate), 0.6 mM of PAPS (sulfate group donor), and 50 mM of MES (pH: 7.0)), allowing a reaction to proceed at 37° C. for 30 minutes, mixing with 2 times the amount of 2.0 M citric acid aqueous solution, and then heat treating the mixture at 95° C. for 15 minutes, thereby stopping the reaction. As the mutant-containing liquid, for example, a purified enzyme liquid or a cell-free extract can be utilized. As the heparosan compound (substrate), those described herein can be used. N-sulfated heparosan, epimerized heparosan, or N-sulfated epimerized heparosan are particular examples. The heparosan may be depolymerized. The heparosan compound (substrate) may also be N-sulfated epimerized depolymerized heparosan.

(1-2) 3-O-Sulfation Enzyme Mutant:

A 3-O-sulfation enzyme mutant is described herein, having a substitution as follows: (i) a methionine residue at position 77 is substituted with a lysine residue; (ii) a tryptophan residue at position 96 is substituted with a phenylalanine residue; (iii) a proline residue at position 125 is substituted with an alanine residue; (iv) a valine residue at position 164 is substituted with an isoleucine residue; (v) an asparagine residue at position 167 is substituted with a histidine residue; (vi) a lysine residue at position 171 is substituted with a glutamine residues; (vii) a tyrosine residue at position 259 is substituted with a phenylalanine residue. The 3-O-sulfation enzyme mutant has a 3-O-sulfate transfer activity, and has an amino acid sequence of one of the following: (a') the amino acid sequence of SEQ ID NO: 8; (b') an amino acid sequence including one or several amino acid substitutions, deletions, insertions, or additions in the amino acid sequence of SEQ ID NO: 8; (c') an amino acid sequence having 90% or more identity to the amino acid sequence of SEQ ID NO: 8; (d') the amino acid sequence consisting of amino acid residues at positions 48 to 311 in the amino acid sequence of SEQ ID NO: 8; (e') an amino acid sequence including one or several amino acid substitutions, deletions, insertions, or additions in the amino acid sequence consisting of amino acid residues at positions 48 to 311 in the amino acid sequence of SEQ ID NO: 8; (f') an amino acid sequence having 90% or more identity to the amino acid sequence consisting of amino acid residues at positions 48 to 311 in the amino acid sequence of SEQ ID NO: 8.

The amino acid sequences shown in (a') to (c') are specified by SEQ ID NO: 8 corresponding to the full-length amino acid sequence of an isoform of mouse-derived 3-OST (3-OST-1). The amino acid sequences shown in (d') to (f') are specified by the catalytic sites of mouse-derived 3-OST-1 (Gly48-His311 in SEQ ID NO: 8).

The term "3-O-sulfate transfer activity" refers to an activity of transferring a sulfate group from a sulfate group donor (e.g., PAPS) toward a hydroxyl group at the 3-position of the α-D-glucosamine residue, thereby producing a structure of "—O-sulfate group" at the 3-position of the α-D-glucosamine residue.

The evaluation of the 3-O-sulfate transfer activity can be suitably performed. For example, as described in the Examples, the 3-O-sulfate transfer activity may be evaluated by measuring the 3-O-sulfate transfer activity and subsequently determining a 3-O-sulfation rate through disaccharide composition analysis. More specifically, the 3-O-sulfate transfer activity may be measured by adding 20 µL of a mutant-containing liquid to 80 µL of a mixed liquid (kept warm at 37° C. in a water bath in advance) of a 1 g/L of a heparosan compound (substrate), 1.25 mM of PAPS (sulfate group donor), and 50 mM of HEPES (pH: 7.5) to start an enzymatic reaction at 37° C. and after elapsing one hour, heating the reaction mixture at 100° C. for 3 minutes, thereby inactivating the enzyme. As the mutant-containing liquid, for example, a purified enzyme liquid or a cell-free extract can be utilized. As the heparosan compound (substrate), those described later can be used. N-sulfated heparosan, 6-O-sulfated heparosan, or N-sulfated 6-O-sulfated heparosan are particular examples. Such heparosan may be depolymerized. The heparosan compound (substrate) may also be N-sulfated 6-O-sulfated depolymerized heparosan.

(1-3) Generation Explanation Regarding Mutant:

In the amino acid sequences shown in the above (b), (e), (b'), or (e'), one or several amino acid residues may be modified by 1, 2, 3, or 4 mutations such as a deletion, substitution, insertion, and addition of the amino acid residue. The mutation of the amino acid residue may be introduced into one region in the amino acid sequence or may be introduced into several different regions. The term "one or several" refers to the number of regions where the proteinaceous activity is not largely impaired. The number referred to by the term "one or several" is, for example 1 to 100, 1 to 80, 1 to 50, 1 to 40, 1 to 30, 1 to 20, 1 to 10, or 1 to 5 (e.g., 1, 2, 3, 4, or 5).

The percent identity to the amino acid sequence shown in the above (c), (f), (c'), or (f') is 90% or more. The identity may be 91% or more, 92% or more, 93% or more, 94% or more, 95% or more, 96% or more, 97% or more, 98% or more, or 99% or more. The calculation of a percent identity of a polypeptide (protein) can be carried out by the algorithm blastp. More specifically, the calculation of a percent identity of a polypeptide can be carried out by the algorithm blastp in the default settings of Scoring Parameters (Matrix: BLOSUM62; Gap Costs: Existence=11 Extension=1; Compositional Adjustments: Conditional compositional score matrix adjustment) which is provided by National Center for Biotechnology Information (NCBI). The calculation of a percent identity of a polynucleotide (gene) can be carried out by the algorithm blastn. More specifically, the calculation of a percent identity of a polynucleotide can be carried out by the algorithm blastn in the default settings of Scoring Parameters (Match/Mismatch Scores=1,−2; Gap Costs=Linear) which is provided by NCBI.

The mutant as shown in the amino acid sequences of (b), (c), (e), (f), (b'), (c'), (e'), or (f') has a characteristic such that it is excellent in production of an objective substance. For example, in the case of measuring the activity under a specified measuring condition, the mutants as shown in the above (b) and (c) can have an activity of 70% or more, 75% or more, 80% or more, 85% or more, 90% or more, 94% or more, 96% or more, 98% or more, or equal to or more than the activity of the mutant as shown in the above (a) as a basis. When measuring the activity under a specified measuring condition, the mutants as shown in the above (e) and (f) can have an activity of 70% or more, 75% or more, 80% or more, 85% or more, 90% or more, 94% or more, 96% or more, 98% or more, or equal to or more than the activity of the mutant as shown in the above (d) as a basis. When measuring the activity under a specified measuring condition, the mutants as shown in the above (b') and (c') can have an activity of 70% or more, 75% or more, 80% or more, 85% or more, 90% or more, 94% or more, 96% or more, 98% or more, or equal to or more than the activity of the mutant as shown in the above (a') as a basis. When measuring the activity under a specified measuring condition, the mutants shown in the above (e') and (f') can have an activity of 70% or more, 75% or more, 80% or more, 85% or more, 90% or more, 94% or more, 96% or more, 98% or more, or equal to or more than the activity of the mutant shown in the above (d') as a basis. As such a specified measuring method, the above-described condition can be utilized.

In the amino acid sequences of the above (b), (c), (e), (f), (b'), (c'), (e'), or (f'), a mutation may be introduced into a site in the catalytic domain and a site other than the catalytic domain so long as the objective characteristic is maintained. The position of the amino acid residue at which the objective characteristic may be maintained, and into which a mutation may be introduced, is apparent to those of ordinary skill in the art. Specifically, it is possible for those of ordinary skill in the art to (1) compare plural amino acid sequences of proteins having the same kind of characteristic, (2) clarify a relatively conserved region and a relatively non-conserved region, and subsequently, (3) estimate a region where an important role may be attained for the function and a region where an important role may not be attained for the function from the relatively conserved region and the relatively non-conserved region, respectively, and therefore, any correlation between the structure and the function can be recognized. As a consequence, those of ordinary skill in the art are able to specify the position of the amino acid residue into which a mutation may be introduced in the amino acid sequence.

When the amino acid residue is mutated by substitution, the substitution of the amino acid residue may be a conservative substitution. The term "conservative substitution" refers to when an existing or native amino acid residue is substituted with an amino acid residue having an analogous side chain. Families of the amino acid residue having an analogous side chain are well-known in the art. Examples of such a family may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a nonpolar side chain (e.g., glycine, alanine, valine, leucine, isoleucine, proline, phenylalanine, methionine, tryptophan), amino acids having a branched side chain at the β-position (e.g., threonine, valine, isoleucine), amino acids having an aromatic side chain (e.g., tyrosine, phenylalanine, tryptophan, histidine), amino acids having a hydroxyl group (e.g., alcoholic, phenolic)-containing side chain (e.g., serine, threonine, tyrosine), and amino acids having a sulfur-containing side chain (e.g., cysteine, methionine). The conservative substitution of the amino acid may be a substitution between aspartic acid and glutamic acid, a substitution among arginine, lysine, and histidine, a substitution between tryptophan and phenylalanine, a substitution between phenylalanine and valine, a substitution among leucine, isoleucine, and alanine, or a substitution between glycine and alanine.

The mutant as described herein may also be a fusion protein ligated with a heterogeneous portion via a peptide bond. Examples of such a heterogeneous portion include peptide components capable of facilitating purification of an objective protein (mutant) (e.g., tag portions, such as histidine tag, Strep-tag II, etc.; and proteins to be utilized for purification of an objective protein, such as glutathione-S-transferase, maltose-binding protein, and mutant types thereof, etc.), peptide components capable of improving solubility of an objective protein (e.g., Nus-tag), peptide components working as a chaperon (e.g., a trigger factor), peptide components having other function (e.g., a full-length protein or a part thereof), and linkers.

Examples of the amino acid sequences as shown in the above (a) to (f) and (a') to (f') include amino acid sequences of natural proteins and their naturally occurring homologues, and artificially produced mutant proteins. The mutant proteins can be, for example, obtained by introducing a mutation into DNA capable of encoding an objective protein and producing a mutant protein by using the obtained mutant protein. Examples of the mutagenesis method include site-specific mutagenesis and random mutagenesis treatments (e.g., a treatment with a mutagen and ultraviolet ray irradiation).

2. Manufacturing Method of an Objective Substance Using a Mutant (2-1) Heparosan Compound:

In accordance with the manufacturing method as described herein, a predetermined objective substance can be produced by using a heparosan compound as a starting material.

The term "heparosan compound" means heparosan or a heparosan derivative.

Heparosan is a polysaccharide made up of a repeating disaccharide unit having a β-D-glucuronic acid (GlcA) residue and an N-acetyl-α-D-glucosamine (GlcNAc) residue [→4)-β-D-GlcA-(1→4)-α-D-GlcNAc-(1→]. The heparosan can be, for example, prepared by the fermentation method utilizing a microorganism having a heparosan-producing ability (e.g., WO/2015/050184A).

The term "heparosan derivative" refers to heparosan having at least one of the following modifications (1) to (7) (e.g., 1, 2, 3, 4, 5, 6, or 7): (1) N-deacetylation of α-D- glucosamine residue; (2) depolymerization; (3) N-sulfation of α-D-glucosamine residue; (4) C5-epimerization of hexuronic acid residue; (5) 2-O-sulfation of hexuronic acid residue; (6) 6-O-sulfation of α-D-glucosamine residue; and/or (7) 3-O-sulfation of α-D-glucosamine residue.

The details of these modifications are as described in the FIG. 1. Heparosan is a polysaccharide constituted of a repeating disaccharide unit consisting of a D-glucuronic acid (GlcA) residue and an N-acetyl-D-glucosamine (GlcNAc) residue and an N-acetyl-D-glucosamine (GlcNAc) residue [→4)-β-D-GlcA-(1→4)-α-D-GlcNAc-(1→]. Specifically, referring to FIG. 1, these modifications are (1) The N-deacetylation of the α-D-glucosamine residue is a reaction of subjecting the N-acetyl group of the α-D-glucosamine residue in heparosan to N-deacetylation (e.g., partial N-deacetylation) to produce an amino group. (2) The depolymerization is a reaction of decomposing heparosan to produce heparosan having a lower molecular weight. (3) The N-sulfation of the α-D-glucosamine residue is a reaction of sulfating the amino group of the α-D-glucosamine residue in heparosan. (4) The C5-epimerization of a hexuronic acid residue is a reaction of isomerizing a β-D-glucuronic acid residue in heparosan into an α-L-iduronic acid (IdoA) residue as an epimer. (5) The 2-O-sulfation of the hexuronic acid residue is a reaction of sulfating the hydroxyl group at the 2-position of the hexuronic acid residue (preferably an α-L-iduronic acid residue) in heparosan. (6) The 6-O-sulfation of the α-D-glucosamine residue is a reaction of sulfating the hydroxyl group at the 6-position of the α-D-glucosamine residue in heparosan. (7) The 3-O-sulfation of the α-D-glucosamine residue is a reaction of sulfating the hydroxyl group at the 3-position of the α-D-glucosamine residue in heparosan. Such a heparosan derivative can be prepared by a treatment as described herein.

The term "hexuronic acid" (HexA) means β-D-glucuronic acid (GlcA) or α-L-iduronic acid (IdoA). The "hexuronic acid residue" in the "C5-epimerization of hexuronic acid residue" of (4) can be β-D-glucuronic acid. As a consequence, in the C5-epimerization of (4), α-L-iduronic acid can be produced through isomerization of β-D-glucuronic acid. In addition, the "hexuronic acid residue" in the "2-O-sulfation of hexuronic acid residue" of (5) can be α-L-iduronic acid. As a consequence, in the 2-O-sulfation of (5), the hydroxyl group at the 2-position of α-L-iduronic acid as the hexuronic acid residue can be sulfated.

(2-2) Method of Producing a Modified Heparosan Compound in which a Hydroxyl Group at the 2-Position of a Hexuronic Acid Residue is Sulfated:

A method of producing a modified heparosan compound in which a hydroxyl group at the 2-position of a hexuronic acid residue is sulfated is described herein. The method as described herein includes the steps of converting a heparosan compound into a modified heparosan compound in which a hydroxyl group at the 2-position of a hexuronic acid residue is sulfated in the presence of the above-described 2-O-sulfation enzyme mutant.

In one embodiment, the heparosan compound as a starting material may also be an N-sulfated heparosan compound. The term "N-sulfated" means that the amino group of the N-acetyl-D-glucosamine residue is sulfated. The N-sulfated heparosan compound can be obtained by subjecting the heparosan to both treatments as described in the above (1) and (3). The N-sulfated heparosan compound may further have at least one of the above modifications (2), (4), (6), and (7) (e.g., 1, 2, 3, or 4).

In another embodiment, the heparosan compound as a starting material may also be an epimerized heparosan compound. The term "epimerized" means that with respect to the hexuronic acid residue, the β-D-glucuronic acid residue is converted into the α-L-iduronic acid residue. The epimerized heparosan compound can be obtained by subjecting the heparosan to the treatment of the above (4). The epimerized heparosan compound may further have at least one of the above modifications (1) to (3), (6), and (7) (e.g., 1, 2, 3, 4, or 5).

In a still another embodiment, the heparosan compound as a starting material may also be a depolymerized heparosan compound. The term "depolymerized" means that the heparosan compound is treated such that its molecular weight is reduced. For example, the "depolymerized" heparosan compound has a number average molecular weight (Mn) of 1,000 to 150,000, or 8,000 to 60,000, and a weight average molecular weight (Mw) of 2,000 to 300,000, or 10,000 to 100,000 in terms of a value measured by GPC on the basis of pullulan. The depolymerized heparosan compound can be obtained by subjecting the heparosan to the above treatment (2). The depolymerized heparosan compound may further have at least one of the following modifications (1), (3), (4), (6), and (7) (e.g., 1, 2, 3, 4, or 5).

In a specified embodiment, the heparosan compound as a starting material may also be an N-sulfated, epimerized, and depolymerized heparosan compound. The "N-sulfated", "epimerized" and "depolymerized" in the N-sulfated, epimerized and depolymerized heparosan compound are those as described above. The N-sulfated, epimerized and depolymerized heparosan compound can be obtained by subjecting the heparosan to the above treatments (1) to (4). The N-sulfated epimerized depolymerized heparosan compound may further have at least one of the following above modifications (6) and (7) (e.g., 1 or 2).

In another embodiment, the heparosan compound as a starting material may also be N-sulfated epimerized depolymerized heparosan (see Example 5(1)). The "N-sulfated", "epimerized" and "depolymerized" in the N-sulfated epimerized depolymerized heparosan are those as described above. The N-sulfated epimerized depolymerized heparosan can be obtained by subjecting heparosan to the above treatments (1) to (4). The N-sulfated epimerized depolymerized heparosan does not have at least one of the following above modifications (6) and (7) (e.g., 1 or 2).

(2-3) Method of Producing a Modified Heparosan Compound in which a Hydroxyl Group at the 3-Position of an α-D-Glucosamine Residue is Sulfated:

A method of producing a modified heparosan compound in which a hydroxyl group at the 3-position of an α-D-glucosamine residue is sulfated is described herein. The present method includes the steps of converting a heparosan compound into a modified heparosan compound in which a hydroxyl group at the 3-position of an α-D-glucosamine residue is sulfated in the presence of the above-described 3-O-sulfation enzyme mutant.

In one embodiment, the heparosan compound as a starting material may be the above-described N-sulfated heparosan compound. The N-sulfated heparosan compound may further have at least one of the above modifications (2) and (4) to (6) (e.g., 1, 2, 3, or 4).

In another embodiment, the heparosan compound as a starting material may also be the above-described epimerized heparosan compound. The epimerized heparosan compound may further have at least one of the above modifications (1) to (3), (5), and (6) (e.g., 1, 2, 3, 4, or 5).

In a still another embodiment, the heparosan compound as a starting material may also be the above-described depolymerized heparosan compound. The depolymerized heparosan compound may further have at least one of the above modifications (1), (3), and (4) to (6) (e.g., 1, 2, 3, 4, or 5).

In a still another embodiment, the heparosan compound as a starting material may also be a 2-O-sulfated heparosan compound. The term "2-O-sulfated" means that a hydroxyl group at the 2-position of a hexuronic acid residue, such as an α-L-iduronic acid residue, is sulfated. The 2-O-sulfated heparosan compound can be obtained by subjecting the heparosan to the above treatment (5). The 2-O-sulfated heparosan compound may further have at least one of the above modifications (1) to (4) and (6) (e.g., 1, 2, 3, 4, or 5).

In a still another embodiment, the heparosan compound as a starting material may also be a 6-O-sulfated heparosan compound. The term "6-O-sulfated" means that a hydroxyl group at the 6-position of an N-acetyl-D-glucosamine residue is sulfated. The 6-O-sulfated heparosan compound can be obtained by subjecting the heparosan to the above treatment (6). The 6-O-sulfated heparosan compound may further have at least one of the above modifications (1) to (5) (e.g., 1, 2, 3, 4, or 5).

In a specified embodiment, the heparosan compound as a starting material may also be an N-sulfated, 6-O-sulfated, and depolymerized heparosan compound. The "N-sulfated", "6-O-sulfated" and "depolymerized" in the N-sulfated, 6-O-sulfated and depolymerized heparosan compound are those as described above. The N-sulfated, 6-O-sulfated, and depolymerized heparosan compound can be obtained by subjecting the heparosan to the above treatments (1) to (3) and (6). The N-sulfated, 6-O-sulfated, and depolymerized heparosan compound may further have at least one of the following above modifications (4) and (5) (e.g., 1 or 2).

In another embodiment, the heparosan compound as a starting material may also be N-sulfated, 6-O-sulfated, and depolymerized heparosan (see Example 9(1)). The "N-sulfated", "6-O-sulfated", and "depolymerized" in the N-sulfated, 6-O-sulfated, and depolymerized heparosan are those as described above. The N-sulfated, 6-O-sulfated and depolymerized heparosan can be obtained by subjecting heparosan to the above treatments (1) to (3) and (6). The N-sulfated, 6-O-sulfated, and depolymerized heparosan does not have at least one of the above modifications (4) and (5) (e.g., 1 or 2).

In another embodiment, the heparosan compound as a starting material may also be N-sulfated 2-O-sulfated 6-O-sulfated epimerized depolymerized heparosan. The "N-sulfated", "2-O-sulfated", "6-O-sulfated", "epimerized" and "depolymerized" in the N-sulfated 2-O-sulfated 6-O-sulfated epimerized depolymerized heparosan are those as described above. The N-sulfated 2-O-sulfated 6-O-sulfated epimerized depolymerized heparosan can be obtained by subjecting the heparosan to the above treatments (1) to (6). It is well-known that in the 3-O-sulfation enzyme, the N-sulfated 2-O-sulfated 6-O-sulfated epimerized depolymerized heparosan can be utilized as a substrate (e.g., WO/2017/115674A, WO/2017/115675A). As a consequence, in the 3-O-sulfation enzyme mutant, the N-sulfated 2-O-sulfated 6-O-sulfated epimerized depolymerized heparosan can be utilized as a substrate.

(2-4) Method of Producing Heparan Sulfate:

A method of producing a heparan sulfate, such as heparin is described herein. The present method includes the steps of subjecting heparosan to a treatment including (1) N-deacetylation of α-D-glucosamine residue, (2) depolymerization, (3) N-sulfation of α-D-glucosamine residue, (4) C5-epimerization of hexuronic acid residue, (5) 2-O-sulfation of hexuronic acid residue, (6) 6-O-sulfation of α-D-glucosamine residue, and (7) 3-O-sulfation of α-D-glucosamine residue, thereby producing a heparan sulfate, wherein (I) the 2-O-sulfation of the hexuronic acid residue is performed in the presence of the above-described 2-O-sulfation enzyme mutant, or (II) the 3-O-sulfation of the α-D-glucosamine residue is performed in the presence of the above-described 3-O-sulfation enzyme mutant.

In the method of producing a heparan sulfate, the treatments of heparosan according to the above (1) to (7) can be performed by the above-described methods which are well-known in the art (e.g., WO 2017/115674 A; WO 2017/115675 A; U.S. Pat. No. 8,227,449; U.S. Patent Application Publication No. 2012/0322114; Lindahl U, et al., (2005) *J Med Chem*, 48(2): 349-352; Zhang Z., et al., (2008) *Journal of the American Chemical Society*, 130(39): 12998-13007; and Chen J, et al., *J Biol Chem.*, 2005 Dec. 30, 280(52): 42817-25).

(1) The N-deacetylation of the α-D-glucosamine residue can be, for example, chemically carried out utilizing a deacetylating agent. Examples of the deacetylating agent include basic substances, such as alkali metal salts, alkaline earth metal salts, hydrazines, etc. Examples of the alkali metal salt include sodium hydroxide, potassium hydroxide, lithium hydroxide, rubidium hydroxide, and cesium hydroxide. Examples of the alkaline earth metal salt include beryllium hydroxide, magnesium hydroxide, calcium hydroxide, strontium hydroxide, and barium hydroxide.

The N-deacetylation can be partial N-deacetylation. The N-deacetylation can be, for example, carried out such that a residual rate of N-acetyl group is a value as described below. That is, for example, the residual rate of N-acetyl group may be 1% or more, 1.5% or more, 3% or more, 5% or more, 7% or more, 9% or more, or 11% or more, and it may be 50% or less, 45% or less, 40% or less, 35% or less, 33% or less, 30% or less, 25% or less, 20% or less, or 17% or less, or it may also be a combination thereof. Specifically, for example, the residual rate of N-acetyl group may be 1% to 33%, 7% to 33%, 7% to 30%, or 11% to 17%. For example, the residual rate of N-acetyl group of 7% to 30% is generally corresponding to the N-acetyl group present in a ratio of one per 6 to 28 sugar residues (one in 3 to 14 units in terms of a disaccharide unit). In addition, for example, the residual rate of N-acetyl group of 11% to 17% is generally corresponding to the N-acetyl group present in a ratio of one per 12 to 18 sugar residues (one in 6 to 9 units in terms of a disaccharide unit). The degree of N-deacetylation (namely, residual rate of N-acetyl group) can be, for example, confirmed through disaccharide analysis. That is, the residual rate of N-acetyl group can be calculated in terms of a ratio (molar ratio) of the amount of the disaccharide unit having an N-acetyl group to the whole amount of the disaccharide units on subjecting the polysaccharide to disaccharide analysis.

As for a condition of the partial N-deacetylation utilizing sodium hydroxide, for example, previously reported conditions (Kuberan B., et al., (2003) *J Biol Chem.*, 278(52): 52613-52621; and U.S. Patent Application Publication No. 2011/0281820) can be made by reference. As for a condition of the partial N-deacetylation utilizing a hydrazine, for example, previously reported conditions (*Glycobiology*, 10 (2000) 159-171; *Carbohydrate Research*, 290 (1996) 87-96; and *Biochem. J.*, 217 (1984) 187-197) can be made by reference.

(2) The depolymerization can be enzymatically carried out utilizing a heparinase. Examples of the heparinase include heparinase I, heparinase II, and heparinase III. Heparinase III is a particular example. The depolymerization is not particularly limited so long as the heparosan is treated such that the molecular weight of the heparosan after depolymerization is lower than that of the heparosan before depolymerization. The depolymerization can be carried such that the heparosan after depolymerization has a number average molecular weight (Mn) of 1,000 to 150,000, or 8,000 to 60,000 and a weight average molecular weight (Mw) of 2,000 to 300,000, or 10,000 to 100,000 in terms of a value measured by GPC on the basis of pullulan.

The depolymerization is performed utilizing heparinase III. The "heparinase III" refers to an enzyme cleaving the site of the N-sulfated or N-acetylated glucosamine residue in a glycosaminoglycan, such as heparosan, etc. (typically EC4.2.2.8). The heparinase III which is used in the method as described herein is not particularly limited so long as it is able to preferentially cleave the site of the glucosamine residue having an N-acetyl group of N-deacetylated heparosan.

(3) The N-sulfation of the α-D-glucosamine residue is a process of sulfating the amino group of the α-D-glucosamine residue in heparosan. The N-sulfation can be, for example, chemically carried out utilizing a sulfating reagent. Examples of the sulfating reagent include sulfur trioxide complexes, such as a sulfur trioxide pyridine complex ($PySO_3$), a sulfur trioxide trimethylamine complex ($TMASO_3$), etc.

(4) The C5-epimerization of the hexuronic acid residue is a process of producing the α-L-iduronic acid residue through isomerization of the β-D-glucuronic acid residue in heparosan. The C5-epimerization can be performed using a C5-epimerase. As the C5-epimerase, various Mammalia- or bacterium-derived C5-epimerases can be used (U.S. Pat. No. 8,227,449; U.S. Patent Application Publication No. 2012/0322114; WO 02/046379 A; Lindahl U, et al., (2005) *J Med Chem*, 48(2): 349-352; Zhang Z., et al., (2008) *Journal of the American Chemical Society*, 130(39): 12998-13007; Chen J, et al., *J Biol Chem.*, 2005 Dec. 30; 280(52): 42817-25; and John R., et al., *J. Biol Chem*, 2013, Aug. 23; 288(34): 24332-9).

(5) The 2-O-sulfation of the hexuronic acid residue is a process of sulfating the hydroxyl group at the 2-position of the hexuronic acid residue, such as an α-L-iduronic acid residue, in heparosan. The 2-O-sulfation can be, for example, enzymatically carried out utilizing various 2-O-sulfation enzymes (2-OST) (e.g., see the literatures listed in the Background Art).

(6) The 6-O-sulfation of the α-D-glucosamine residue is a process of sulfating the hydroxyl group at the 6-position of the α-D-glucosamine residue in heparosan. The 6-O-sulfation can be, for example, enzymatically carried out utilizing a 6-O-sulfation enzyme (6-OST). Examples of the 6-OST include 6-OST-1, 6-OST-2, and 6-OST-3. The 6-O-sulfation can also be, for example, chemically carried out utilizing a sulfating reagent. Examples of the sulfating reagent include sulfur trioxide complexes, such as a sulfur trioxide pyridine complex ($PySO_3$), a sulfur trioxide trimethylamine complex ($TMASO_3$), etc.

(7) The 3-O-sulfation of the α-D-glucosamine residue is a process of sulfating the hydroxyl group at the 3-position of the α-D-glucosamine residue in heparosan. The 3-O-sulfation can be, for example, enzymatically carried out utilizing a 3-O-sulfation enzyme (3-OST). Examples of the 3-OST include 3-OST-1, 3-OST-2, 3-OST-3, 3-OST-4, and 3-OST-5 (e.g., see the literatures listed in the Background Art).

The above-described treatments can be performed in any arbitrary order. For example, the depolymerization (2) can be performed before or after or on the way of the above (1) and (3) to (7). It may be performed after the above (1) and before the above (3). In addition, the treatments of the above (5) to (7) may be performed in any order. Typically, the treatments can be performed in the order of 2-O-sulfation, 3-O-sulfation, and 6-O-sulfation, or in the order of 2-O-sulfation, 6-O-sulfation, and 3-O-sulfation. The above-described treatments may also be performed in the numeric order (FIG. 1). Two or more of the above-described treatments may be carried out simultaneously or separately.

The product by each process may be subjected to a next process while present in the reaction liquid, or may be subjected to the next process after recovering the product from the reaction liquid. The means for recovering each product from the reaction liquid is not particularly limited. Examples of the means for recovering each product include known methods which are adopted for separation and purification of compounds, such as a membrane treatment method, a precipitation method, etc. The product by each process may be suitably subjected to a treatment, such as purification, dilution, concentration, drying, dissolution, inactivation of enzyme, etc., and then subjected to the next process. The purification may be carried out in a desired extent. These treatments may be carried out alone or properly in combination.

(2-5) Implementation Manners of the Methods of the Above (2-2) to (2-4):

Each of the reactions in the methods of the above (2-2) to (2-4) can be suitably performed in an appropriate system (e.g., buffer system, fermentation system). As a condition of such a reaction, previously reported conditions (e.g., see the above-described literatures) or the conditions described in the Examples can be adopted. For example, the methods of (2-2) and (2-3) can be performed through a reaction in a buffer (e.g., IVIES, HEPES) containing 0.1 to 50 g/L of a heparosan compound and 0.05 to 10 mM of PAPS and having an appropriate pH (e.g., 5.0 to 9.0) at an appropriate temperature (e.g., 25 to 42° C.) for a desired time (e.g., 10 minutes to 48 hours).

In one embodiment, the method as described herein can be performed using the mutant as described herein (hereinafter referred to as "protein" or the like, as required) itself. For example, when using a recombinant protein as the mutant as described herein, the recombinant protein can be obtained from a transformed microorganism capable of producing the mutant by using a cell-free system vector. The mutant can be utilized as an unpurified, crude, or purified protein. Such a protein may also be utilized as an immobilized protein, which means the protein is immobilized in a solid phase, in the reaction.

A medium for culturing a transformed microorganism is known, and for example, media obtained by adding a carbon source, a nitrogen source, a vitamin source, and the like to a nutrient medium, such as an LB medium, etc., or a minimal medium, such as an M9 medium, etc., can be used. The transformed microorganism is typically cultured at 16 to 42° C., 25 to 37° C. for 5 to 168 hours, or 8 to 72 hours, according to the chosen host. It is possible to perform either a shaking culture and/or a static culture, depending upon the chosen host. Stirring may be performed, or aeration may be performed, as required. When choosing an actinomycete as an expression host, a condition which may be used for the purpose of producing a protein can be suitably used. In addition, when using an inducible promoter for the purpose of expression of a protein, the culture can also be performed by adding a promoter inducing agent to the medium.

It is possible to purify and isolate the produced protein by a known precipitation method, such as salting-out, isoelectric precipitation, solvent precipitation, etc., from an extract of transformed microorganism; a method utilizing a difference in molecular weight, such as dialysis, ultrafiltration, gel filtration, etc.; a method utilizing specific affinity, such as ion exchange chromatography, etc.; a method utilizing a difference in hydrophobicity, such as hydrophobic chromatography, reverse-phase chromatography, etc.; other affinity chromatography, SDS polyacrylamide electrophoresis, isoelectric electrophoresis, or the like, or a combination thereof. When an objective protein is secretorily expressed, a culture supernatant containing the protein can be obtained by removing a bacterial cell by centrifugation or the like from a culture broth obtained by culturing a transformed microorganism. The protein can be also purified and isolated from this culture supernatant.

In another embodiment, the method as described herein can be performed in the presence of a transformed microorganism capable of producing the mutant as described herein or an extract thereof.

As the extract of the microorganism capable of producing the mutant, an objective protein-containing treated liquid which was treated by an arbitrary method can be used. As such a treatment, the method as mentioned above for isolation and purification and a microbiocidal treatment method of making it possible to kill the microorganism can be adopted. As a microbiocidal treatment method, an arbitrary method of making it possible to kill the microorganism can be used. Examples thereof include a heat treatment, an acidic treatment, an alkaline treatment, a surfactant treatment, and an organic solvent treatment.

In an embodiment, the transformed microorganism is a polynucleotide containing a nucleotide sequence encoding the mutant and a host cell containing an expression unit containing a promotor operably ligated therewith.

The term "expression unit" refers to a minimum unit containing a predetermined polynucleotide to be expressed as a protein and a promoter operably ligated therewith, which makes it possible to achieve the transfer of the polynucleotide, and in turn, the production of a protein encoded by the polynucleotide. The expression unit may further contain an element, such as a terminator, a ribosome binding site, a drug-resistant gene, etc. The expression unit may be DNA or RNA and can be DNA.

The expression unit may be either homologous (namely, inherent) or heterologous (namely, non-inherent) to the post cell. It can be a heterologous expression unit. The term "heterologous expression unit" means that the expression unit is heterologous to the host cell. As a consequence, at least one element in the expression unit is heterologous to the host cell. Examples of the element in the expression unit, which is heterologous to the host cell, include the above-described elements. Either one or both of the polynucleotide encoding the objective protein and the promotor in the heterologous expression unit are heterologous to the host cell. As a consequence, either one or both of the polynucleotide encoding the objective protein and the promotor are derived from an organism other than the host cell (e.g., a prokaryote and a eukaryote, or a microorganism, an insect, a plant, and an animal, such as a Mammalia, etc.) or a virus, or an artificially synthesized material. Alternatively, the polynucleotide encoding the objective protein may be heterologous to the host cell. The objective protein can be heterologous to the host cell.

The promoter in the heterologous expression unit is not particularly limited so long as it is able to express the protein to be encoded with the polynucleotide ligated with the downstream thereof, with the host cell. For example, the promoter may be either homologous or heterologous to the host cell. For example, constitutions or inducible promoters which are generally used for the production of a recombinant protein can be used. Examples of such a promoter include a PhoA promoter, a PhoC promoter, a T7 promoter, a T5 promoter, a T3 promoter, a lac promoter, a trp promoter, a trc promoter, a tac promoter, a PR promoter, a PL promoter, a SP6 promoter, an arabinose-inducible promoter, a cold shock promoter, and a tetracycline-inducible promoter. A promoter having a strong transfer activity in the host cell can be used. Examples of the promoter having a strong transfer activity in the host cell include a promoter of a gene which is highly expressed in the host cell and a virus-derived promoter.

Examples of the host cell which can be used as the transformed microorganism include various microorganisms such as a bacterium belonging to the genus *Escherichia* (e.g., *Escherichia coli*), an actinomycete, and a coryneform bacterium. *Escherichia coli* strains that can be used as a host cell include those that are frequently utilized for general cloning or expression of heterologous proteins, for example, HB101, MC1061, JM109, CJ236, and MV1184. Actinomycete strains that can be used as the host cell include those strains which are in general frequently utilized for expression of proteins of heterologous proteins, for example, *S. lividans* TK24, and *S. coelicolor* A3(2. A bacterium of the genus *Corynebacterium* that can be used as the host cell include an aerobic gram-positive *bacillus* that has previously been classified into the genus *Brevibacterium*; however, at present, it includes bacteria unified into the genus *Corynebacterium* (*Int. J. Syst. Bacteria*, 41, 255 (1981)) and bacteria belonging to the genus *Brevibacterium*, which is very closely-related to the genus *Corynebacterium*. Advantages of using coryneform bacteria include that they inherently secrete an extremely small amount of proteins to the outside of bacterial cells as compared with fungi, yeasts, *Bacillus* bacteria, etc., which are conventionally used for secretory production of proteins. Therefore, when producing the objective protein via secretion, the purification process can be simplified or eliminated, such as when performing an enzymatic reaction with enzyme that is secreted, a culture supernatant can be used as the enzyme source, and therefore, impurities or side reactions due to bacterial cell components, contaminating enzymes, etc. can be reduced. As a result the coryneform bacteria can grow well in a simple medium containing a saccharide, ammonia, an inorganic salt, etc., and therefore, they are excellent in view of cost of medium, culture method, and culture productivity. In addition, by utilizing the Tat system secretory pathway, it is also possible to efficiently secrete proteins that are industrially useful; and the secretory production of which is difficult in the conventionally known Sec system secretory pathway, such as isomaltodextranase, protein glutaminase, etc. (WO 2005/103278 A). *Corynebacterium glutamicum* as disclosed in WO 01/023491 A, WO 02/081694 A, WO 01/023491 A, etc. can also be used.

The transformed microorganism can be a bacterium belonging to the genus *Escherichia*. The bacterium belonging to the genus *Escherichia* can be *Escherichia coli*.

The transformed microorganism can be prepared by an arbitrary method which is known in the art. For example, the expression unit can be present in the host cell so that it is incorporated into genome DNA of the host cell, or so that it is not incorporated into genome DNA of the host cell, e.g., as a part of an expression vecto). The host cell containing an expression unit can be obtained by transforming the host cell with an expression vector by an arbitrary method which is known in the art, such as, e.g., a competent cell method, an electroporation method. When the expression vector is an integrative vector which generates homologous recombination with the genome DNA of the host cell, the expression unit can be incorporated into the genome DNA of the host cell through transformation. When the expression vector is a non-integrative vector which does not generate homologous recombination with the genome DNA of the host cell, the expression unit is not incorporated into the genome DNA of the host cell through transformation but can be present in the host cell as part of an expression vector that is independent of the genome DNA. Alternatively, it is possible to incorporate the expression unit into the genome DNA of the host cell by the genome editing technology (e.g., CRISPR/Cas system, Transcription Activator-Like Effector Nucleases (TALEN)).

The expression vector may further contain, in addition to the above-described minimum unit as the expression unit, an element functioning in the host cell, such as a terminator, a ribosome binding site, a drug-resistant gene, etc. Examples of the drug-resistant gene include drug-resistant genes to drugs, such as tetracycline, ampicillin, kanamycin, hygromycin, phosphinothricin, etc.

The expression vector may further contain a region that enables the homologous recombination with the genome DNA of the host cell. For example, the expression vector may be designed such that the expression unit contained therein is positioned between a pair of homologous regions (e.g., a homology arm homologous to a specified sequence in the genome of the host cell, loxP, FRT). The genome region of the host cell, that is, the target of the homologous region, into which the expression unit is to be introduced is not particularly limited but may also be a locus of gene in which the expression amount is large in the host cell.

The expression vector may be a plasmid, a virus vector, a phage, or an artificial chromosome. The expression vector may also be either an integrative vector or a non-integrative vector. The integrative vector may be a vector of a type in which the whole is incorporated into the genome of the host cell. Alternatively, the integrative vector may also be a vector in which only a part thereof (e.g., an expression unit) is incorporated into the genome of the host cell. The expression vector may further be a DNA vector or an RNA vector (e.g., a retrovirus). As the expression vector, generally-used expression vectors may be used. Examples of such an expression vector include pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30), and derivatives thereof. In addition, in the case of choosing, as the host cell, the coryneform bacterium, such as *Corynebacterium glutamicum*, pPK4 that is a high copy vector, etc. can be suitably utilized.

EXAMPLES

The present invention is described in more detail by reference to Examples, but the present invention is not limited to the following Examples.

Example 1: Preparation of N-Sulfated Epimerized Depolymerized Heparosan (1) Heparosan Fermentation A culture broth containing heparosan was obtained according to the heparosan-producing bacterium (*Escherichia coli* BL21(DE3)/pVK9-kfiABCD strain) and the culturing conditions as described in Example 1 of WO 2015/050184 A.

(2) Purification of Heparosan

A culture supernatant was recovered from the culture broth by means of centrifugation. In order to remove the medium components, 1 mL of the culture supernatant was washed with milliQ water by using a UF membrane and concentrated to 250 μL. To 250 μL of the UF membrane-concentrated liquid, 500 μL of 100% ethanol was added, and heparosan was precipitated by means of centrifugation. The obtained precipitate was air-dried to obtain heparosan. Heparosan was purified from the remaining culture supernatant by the same procedures, thereby obtaining 10 g of heparosan in total.

(3) N-Deacetylation of Heparosan

First, to 1.22 g of heparosan, 61 mL of hydrazine·$H_2O$ and 4.7 mL of 1N sulfuric acid were added, and after purging the gas phase with nitrogen, the contents were heated to 100° C. and allowed to react with each other for 4.75 hours.

Subsequently, the reaction was stopped by means of ice cooling, 61 mL of a 16% NaCl aqueous solution and 610 mL of MeOH were then added, and the contents were centrifuged to remove a supernatant. The obtained precipitate was dissolved in 50 mL of $H_2O$ and then desalted and concentrated using an Amicon UF membrane (3 kDa).

Subsequently, to the obtained concentrate, 2 times the amount of $H_2O$ and an equal amount of 1M $NaHCO_3$ were added, and a 0.2M $I_2$/0.4M KI solution was dripped until the mixture was colored yellow. Thereafter, hydrazine·$H_2O$ was dripped; the excessive iodine was reduced into an iodine ion; the resultant was again desalted and concentrated using an Amicon UF membrane (3 kDa); and the concentrate was subjected to evaporation to dryness under reduced pressure, thereby obtaining N-deacetylated heparosan. A residual rate of N-acetyl group in the obtained N-deacetylated heparosan was 14.9% (as described later).

(4) Depolymerization of N-Deacetylated Heparosan (4-1) Preparation of Heparinase III <Construction of Expression Plasmid for hepC Genes Derived from *Flavobacterium heparinum*>

From the *Flavobacterium heparinum* (ATCC13125), the hepC gene encoding heparinase III was cloned into the pMIV-Pn1p0 vector (U.S. Patent Application Publication No. 2005/0196846) to construct a hepC gene expression plasmid, pMIV-Pn1p0-hepC. Strong nlp0 promoter (Pn1p0) and rrnB terminator are incorporated into pMIV-Pn1p0-ter, and the promoter and the terminator can function as an expression unit of a target gene when the target gene is inserted therebetween. "Pn1p0" indicates the wild-type promoter of the nlpD gene derived from the *Escherichia coli* K-12 strain.

The details of the construction of the expression plasmid are shown below. By PCR using the chromosomal DNA of *Escherichia coli* MG1655 as the template, as well as the primer P1 (SEQ ID NO: 11) and primer P2 (SEQ ID NO: 12), a DNA fragment was obtained containing the promoter region (PnlpO) of the nlpD gene of about 300 bp. The sites for the restriction enzymes SalI and PaeI were designed in the 5' end regions of the respective primers. The PCR cycles consisted of 95° C. for 3 minutes, following 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and 72° C. for 5 minutes as the final cycle. The obtained fragment was treated with SalI and PaeI, and inserted into pMIV-5JS (Japanese Patent Laid-open (Kokai) No. 2008-99668) at the SalI-PaeI site to obtain plasmid pMIV-Pn1p0. The nucleotide sequence of the PaeI-SalI fragment of the Pn1p0 promoter inserted into this pMIV-Pn1p0 plasmid is as shown as SEQ ID NO: 13.

Subsequently, by PCR using the chromosomal DNA of MG1655 as the template, as well as the primer P3 (SEQ ID NO: 14) and primer P4 (SEQ ID NO: 15), a DNA fragment (SEQ ID NO: 16) containing about 300 bp of the terminator region of the rrnB gene was obtained. The sites for the restriction enzymes XbaI and BamHI were designed in the 5' end regions of the respective primers. The PCR cycles consisted of 95° C. for 3 minutes, following 2 cycles of 95° C. for 60 seconds, 50° C. for 30 seconds, and 72° C. for 40 seconds, 25 cycles of 94° C. for 20 seconds, 59° C. for 20 seconds, and 72° C. for 15 seconds, and 72° C. for 5 minutes as the final cycle. The obtained fragment was treated with XbaI and BamHI, and inserted into pMIV-Pn1p0 at the XbaI-BamHI site to obtain plasmid pMIV-Pn1p0-ter.

Subsequently, a DNA strand containing ORF of hepC genes derived from *Flavobacterium heparinum* (ATCC13125) (Su H., et al., *Appl. Environ. Microbiol.*, 1996, 62:2723-2734) was artificially synthesized. By PCR using this DNA strand as the template, as well as the primer P5 (SEQ ID NO: 17) and primer P6 (SEQ ID NO: 18) as the primers, a DNA fragment for hepC gene was amplified. PrimeStar Polymerase (TaKaRa) was used for PCR, and PCR was performed in the reaction composition described in the attached protocol. The PCR cycles consisted of 94° C. for 5 minutes, following 30 cycles of 98° C. for 5 seconds, 55° C. for 10 seconds, and 72° C. for 8 minutes, and final maintenance at 4° C. Further, by PCR using pMIV-Pn1p0 as the template DNA and the oligonucleotides of the primer P7 (SEQ ID NO: 19) and primer P8 (SEQ ID NO: 20) as the primers, a DNA fragment of pMIV-Pn1p0 was obtained. PimeStar Polymerase was used for PCR, and PCR was performed in the reaction composition described in the attached protocol. The PCR cycles consisted of 94° C. for 5 minutes, following 30 cycles of 98° C. for 5 seconds, 55° C. for 10 seconds, and 72° C. for 6 minutes, and final maintenance at 4° C. Both the obtained DNA fragments were ligated with each other by using In-Fusion (registered trademark) HD Cloning Kit (manufactured by Clontech) to construct a hepC gene expression plasmid, pMIV-Pn1p0-hepC. A nucleotide sequence containing the cloned hepC genes is shown as SEQ ID NO: 21, and an amino acid sequence of heparinase III (HepC) encoded thereby is shown as SEQ ID NO: 22.

<Construction of hepC Gene-Expressing Strain of *Escherichia coli* BL21 (DE3) Strain and Preparation of Heparinase III Enzyme Liquid>

The hepC gene expression plasmid, pMIV-Pn1p0-hepC, was introduced into the *Escherichia coli* BL21(DE3) strain (Life Technologies) by electroporation (cell: 80 µL, 200 Ω, 25 µF, 1.8 kV, cuvette: 0.1 mL) to obtain *Escherichia coli* BL21(DE3)/pMIV-Pn1p0-hepC strain as a heparinase III production strain. This strain was spread on the LB medium having 25 µg/mL of chloramphenicol added thereto and pre-cultured overnight at 37° C. Thereafter, the culture broth was inoculated in 300 mL of an LB medium contained in a Sakaguchi flask such that the final concentration was 2% v/v. Shaking culture was performed at 37° C. for 4 hours, and the culture was then finished. After centrifugation, the bacterial cell was washed twice with 0.85% NaCl and suspended in 30 mL of a 50 mM HEPES buffer (pH: 7.0). The suspension was subjected to ultrasonication to disrupt the bacterial cell. The cell-disrupted liquid was centrifuged to prepare the heparinase III enzyme liquid as a supernatant (cell-free extract).

(4-2) Depolymerization by Heparinase III Reaction 1 g of the N-deacetylated heparosan having a residual rate of N-acetyl group of 14.9% as obtained in the above (3) and 2 mL of the heparinase III solution of 31.3 mIU/µL were dissolved in 100 mL of a Tris buffer (pH: 8.0) containing 100 mM of NaCl and 1.5 mM of $CaCl_2$), and the contents were allowed to react with each other at 37° C. for 5.3 hours. The reaction liquid was added and mixed with 100 mL of a 16% NaCl aqueous solution and 900 mL of EtOH, and the mixture was centrifuged to remove a supernatant, thereby obtaining a depolymerized, N-sulfated and deacetylated heparosan. The molecular weight after depolymerization with heparinase III was measured by GPC on the basis of pullulan. As a result, the number average molecular weight (Mn) was 9,860, and the weight average molecular weight (Mw) was 15,430.

(5) N-Sulfation of Depolymerized and N-Deacetylated Heparosan

First, 1 g of the depolymerized, N-deacetylated heparosan obtained in the above (4) was dissolved in 50 mL of milliQ water, to which was then added 50 mL of an aqueous solution of 20 mg/mL of $NaHCO_3$ and 20 mg/mL of trimethylamine·$SO_3$, and the contents were allowed to react with each other overnight at 55° C.

Subsequently, 1 L of EtOH was added and mixed, and the mixture was centrifuged to remove a supernatant, thereby obtaining an N-sulfated and depolymerized heparosan.

Subsequently, the obtained N-sulfated and depolymerized heparosan was dissolved in milliQ water to make 500 µL, and the solution was subjected to disaccharide analysis to determine a yield relative to the N-deacetylated heparosan. The procedures are shown below.

<Disaccharide Analysis>

The disaccharide analysis of the N-sulfated and depolymerized heparosan was carried out according to previously reported conditions (T. Imanari, et al., "High-performance liquid chromatographic analysis of glycosaminoglycan-derived oligosaccharides", *J. O. Chromato. A*, 720, 275-293 (1996)). That is, the N-sulfated depolymerized heparosan was decomposed into an unsaturated disaccharide by using heparinase II and heparinase III, and the decomposition product was analyzed by HPLC, thereby quantifying the amounts of the respective constituent disaccharides.

Similarly, the disaccharide analysis of the N-deacetylated heparosan was carried out. The disaccharide analysis of the N-deacetylated heparosan was carried out after N-sulfating the N-deacetylated heparosan. That is, the amounts of the respective constituent disaccharides were quantified by N-sulfating the N-deacetylated heparosan, decomposing the resultant into an unsaturated disaccharide by using heparinase II and heparinase III, and analyzing the decomposition product by HPLC. The N-sulfation of the N-deacetylated heparosan was carried out in the same manner as in the N-sulfation of the depolymerized N-deacetylated heparosan.

The disaccharide analysis was specifically carried out in the following procedures.

(a) 0.2 U of heparinase II (Sigma), 0.02 to 0.03 mIU of heparinase III, 5 μg of a polysaccharide sample, and 10 μL of a buffer for enzyme digestion (100 mM of $CH_3COONa$ and 10 mM of $(CH_3COO)_2Ca$, pH: 7.0) were mixed and diluted with milliQ water to make 100 μL, thereby preparing a reaction solution.

(b) The reaction solution was allowed to react at 37° C. for 16 hours or more and then boiled at 100° C. for 2 minutes, thereby stopping the reaction.

(c) The solution from which an insoluble matter was removed with a 0.45 μm-filter was designated as a sample for disaccharide analysis.

(d) The analysis was performed in the following manner. Column: Inertsil ODS-3 150 mm×2.1 mm, particle diameter: 5 μm, temperature: 50° C., flow rate: 0.25 mL/min, detection wavelength: 230 nm, eluting solution (solution A): 4% acetonitrile and 1.2 mM of tributylamine, eluting solution (solution B): 4% acetonitrile and 0.1 M CsCl, gradient condition: 1 to 90% of solution B.

The yield was calculated from a sum total of the amounts of the constituent saccharides produced by the respective polysaccharide samples. That is, the yield was calculated as a ratio (molar ratio) of the whole amount of the disaccharides produced from the N-sulfated and depolymerized heparosan relative to the whole amount of the disaccharides produced from the N-deacetylated heparosan. In addition, at that time, in the obtained N-sulfated and depolymerized heparosan, it was confirmed that 99% or more of the amino group generated by the N-deacetylation was N-sulfated.

In addition, a residual rate of N-acetyl group in the N-deacetylated heparosan was calculated on the basis of the amounts of the respective constituent saccharides produced from the N-deacetylated heparosan. That is, the residual rate of acetyl group was calculated as a ratio (molar ratio) of the amount of the disaccharide having an N-acetyl group relative to the total amount of the disaccharides. The residual rate of acetyl group was 14.9%.

(6) Preparation of N-Sulfated, Epimerized and Depolymerized Heparosan (6-1) Preparation of Purified D-Glucuronyl C5-Epimerase (Dlce)

<Construction of Zebrafish-Derived Dlce Expression Strain>

By a PCR reaction using pMAL-c2× (SEQ ID NO: 23, New England BioLabs) as the template DNA, as well as SEQ ID NOS: 24 and 25 as the primers, there was obtained a C-terminal region DNA fragment of a mutant type maltose binding protein (MBP*). In the above-described PCR reaction, a recognition site for a restriction enzyme BglII was added to the 5'-terminal, and recognition sites for restriction enzymes HindIII, BamHI, SacI, XhoI, and NotI were added to the 3'-terminal. The pMAL-c2× plasmid DNA and the C-terminal region DNA fragment of MBP* were cleaved with BglII and HindIII, followed by performing the ligation reaction to obtain a pMAL-MBP* plasmid. The nucleotide sequence of the pMAL-MBP* plasmid is shown as SEQ ID NO: 26.

By using pMAL-MBP* as the template DNA and PrimeStar Polymerase (TaKaRa) as a polymerase, PCR was performed according to the protocol of the manufacturer, thereby obtaining a DNA fragment of pMAL-MBP*. A combination of SEQ ID NOS: 27 and 28 was used as the primer.

cDNA of zebrafish-derived Dlce was prepared through artificial gene synthesis (Thermo Fisher Scientific K.K.). By a PCR reaction using the cDNA as the template, as well as SEQ ID NOS: 29 and 30 as the primers, a DNA fragment was obtained containing a nucleotide sequence encoding a catalytic site of the zebrafish-derived Dlce (G70-Asn585). The obtained DNA fragment and the DNA fragment of pMAL-MBP* were ligated with each other by using In-Fusion (registered trademark) HD Cloning Kit (manufactured by Clontech). An *Escherichia coli* JM109 strain was transformed with the reaction liquid, thereby obtaining pMAL-MBP*-dreDlce (G70). *Escherichia coli* Origami B (DE3) was transformed with the obtained plasmid and named as *Escherichia coli* Origami B (DE3)/pMAL-MBP*-dreDlce (G70). A nucleotide sequence of the inserted fragment and an amino acid sequence to be encoded thereby are shown as SEQ ID NOS: 31 and 32, respectively.

<Preparation of D-glucuronyl C5-epimerase (Dlce)>

The *Escherichia coli* Origami B (DE3)/pMAL-MBP*-dreDlce (G70) was inoculated in an LB medium having 100 μg/mL of ampicillin added thereto and pre-cured overnight at 37° C. Thereafter, the culture broth was inoculated in 100 mL of an (LB+Glycerol) medium having 100 μg/mL ampicillin added thereto (95% (v/v) of LB medium, 1.0% (v/v) of glycerol, 5 mM of MOPS-KOH (pH: 7.0)) contained in a 500 mL-volume Sakaguchi flask such that the final concentration was 1%. Shaking culture was performed at 37° C. until the OD660 became 0.5 to 0.7. Thereafter, isopropyl-β-D-thiogalactopyranoside (IPTG) (Nacalai Tesque, Inc.) was added such that the final concentration was 0.5 mM, and the resultant was further cultured overnight at 22° C.

After centrifuging the culture both, the bacterial cell was recovered, once washed with a buffer-1 (20 mM of Tris-HCl (pH: 7.5) and 200 mM of NaCl), and then suspended. The suspension was subjected to ultrasonication with an ultrasonicator 201M (Kubota Corporation), and after centrifugation at 14,000 rpm for 20 minutes, a supernatant was obtained as a cell-free extract. Subsequently, the cell-free extract was supplied to MBPTrap HP 5 ml (GE Healthcare) equilibrated with 20 mM of Tris (pH: 7.5) and 200 mM of NaCl. The non-adsorbed protein was washed with the buffer-1 and then eluted with the buffer-1 having 10 mM maltose added thereto, thereby obtaining a purified MBP*-dreDlce (G70).

(6-2) C5-Epimerization with Dlce

A C5-epimerization reaction of the N-sulfated depolymerized heparosan obtained in the above (4) was carried out. 8 mU/mL of the purified MBP*-dreDlce (G70) was added to 4 g/L of the N-sulfated depolymerized heparosan, 50 mM of MES (pH: 7.0), and 1 mM of calcium chloride, and the contents were allowed to react with each other overnight at 37° C. The reaction was stopped through a heat treatment at 95° C. for 15 minutes, and the reaction stop liquid was subjected to liquid substitution with ultra-pure water by using Amicon Ultra-15 3 K (Merck Millipore).

(6-3) Quantification of C5-Epimerization Rate

The quantification of a C5-epimerization rate was carried out by disaccharide composition analysis by nitrous acid degradation. As a result, the C5-epimerization rate was 26.7%.

<Reagent>

$NaNO_2$ (CAS No.: 7632-00-0, MW: 69.01)

Citric acid (CAS No.: 77-92-9, MW: 192.1)

2,4-Dinitrophenyl hydrazine (CAS No.: 119-26-6, MW: 198.1), containing 50% of water (abbreviation: DNPH)

<Testing Liquids>

$NaNO_2$ aqueous solution: Solution of 49.5 mg of the reagent dissolved in 1 mL of $H_2O$ Citric acid aqueous solution: Solution of 384.2 mg of the reagent dissolved in 1 mL of $H_2O$ DNPH aqueous solution: Solution of 20.4 mg of the reagent (containing 50% of water) dissolved in 1 mL of acetonitrile <Analysis Procedures>

In a 1.5 mL-microtube (Eppendorf), 10 μL of the reaction liquid, 20 μL of the citric acid buffer, and 10 μL of the NaNO$_2$ aqueous solution were successively added, and the mixed solution was stirred (at 1,000 rpm) at 65° C. for 2 hours, thereby obtaining a nitrous acid degraded liquid. To 40 μL of the obtained nitrous acid degraded liquid, 20 μL of the DNPH solution were added, and the contents were stirred (at 1,000 rpm) at 45° C. for 2 hours, thereby obtaining a derivatized liquid. A composition of the obtained derivatized liquid was analyzed by HPLC under the following condition.

<HPLC Analysis Condition>

Column: ODS Z-CLUE 3 μm (manufactured by Sumika Chemical Analysis Service, Ltd.) 2.0 mm×250 mm
Column case temperature: 50° C.
Flow rate of eluting solution: 0.3 mL/min
Detection: UV 365 nm
Injection amount: 5 μL
Composition of eluting solution:
Solution A: 50 mM-HCOONH$_4$ (pH: 4.5)
Solution B: MeCN

TABLE 1

Gradient conditions of HPLC

| Time (min) | Solution A (%) | Solution B (%) |
|---|---|---|
| 0.0 | 90 | 10 |
| 13.0 | 80 | 20 |
| 27.0 | 20 | 80 |
| 27.1 | 90 | 10 |
| 40.0 | 90 | 10 |

TABLE 2

| Disaccharide derivative (showing the structure before nitrous acid degradation) | Relative retention time (min) |
|---|---|
| GlcA(2S)-GlcN(NS) | 1.41 |
| IdoA(2S)-GlcN(NS) | 1.50 |
| GlcA-GlcN(NS) | 1.73 |
| IdoA-GlcN(NS) | 1.89 |

Example 2: Construction of 2-O-Sulfation Enzyme (2-OST) Expression Strain (1) Construction of pC2-1

As a 2-O-sulfation enzyme (2-OST), a fusion protein (MBP**-2-OST) of catalytic sites (Asp69-Asn356) of a mutant resulting from conversion of a tyrosine residue at the 94th of the Chinese hamster-derived 2-OST into alanine and a maltose-binding protein MBP was utilized.

The details of the construction of the expression plasmid are shown below. By using pMAL-c2× plasmid as the template DNA and PrimeStar Polymerase (TaKaRa) as the polymerase, PCR was performed according to the protocol of the manufacturer, thereby obtaining a DNA fragment of pMAL-MBP**. A combination of SEQ ID NOS: 33 and 34 was used as the primer.

cDNA (optimized in conformity with the codon usage of *Escherichia coli*) of a mutant resulting from conversion of a tyrosine residue 94 of the Chinese hamster-derived 2-OST into isoleucine was prepared through artificial gene synthesis (Thermo Fisher Scientific K.K.) by reference to the report of Kobayashi, et al. (Kobayashi M., et al., *Jour. Biol. Chem.*, 1997, 272:13980-13985) (see SEQ ID NOS: 5 and 6 regarding the nucleotide sequence and the amino acid sequence). A DNA fragment 2-OST (Y64A) containing the nucleotide sequence encoding the catalytic sites of Chinese hamster-derived 2-OST (Asp69-Asn356) was obtained through a PCR reaction using the foregoing cDNA as the template and the oilgonucleotides of SEQ ID NOS: 35 and 36 as the primers. The obtained DNA fragment and the DNA fragment of pMAL-MBP** were ligated with each other by using In-Fusion (registered trademark) HD Cloning Kit (manufactured by Clontech). An *Escherichia coli* JM109 strain was transformed with the reaction liquid and applied in an LB agar medium containing 100 μg/mL of ampicillin, followed by culturing overnight at 37° C. The plasmid was extracted from a colony of the grown transformed microorganisms according to a known method. The nucleotide sequence was confirmed with 3100 Genetic Analyzer (manufactured by Applied Biosystems), and the plasmid having an objective structure was called as "pC2-1".

(2) Construction of Mutant Type 2-OST Expression Plasmid

In order to construct a mutant type 2-OST expression plasmid, by using primers (SEQ ID NOS: 37 to 64) corresponding to various mutant types, PCR was carried out using pMAL-MBP**-2-OST (Y94A) as the template. The relation between each mutation and primer is shown in Table 3. After digesting the obtained PCR product with DpnI, the *Escherichia coli* JM109 strain was transformed with the reaction liquid and applied to an LB agar medium containing 100 μg/mL of ampicillin, followed by culturing overnight at 37° C. The plasmid was extracted from a colony of the grown transformed microorganisms according to a known method. The nucleotide sequence was confirmed with 3100 Genetic Analyzer (manufactured by Applied Biosystems), thereby obtaining plasmids pC2-2, 3, 4, 5, 6, 7, 8, 10, 11, and 12, each having an objective structure. PCR was carried out with pC2-3 as the template in the same manner, thereby constructing pC2-22, 25, 26, 27, and 28. The relations among each mutation, primer, and plasmid are shown in Table 3.

TABLE 3

| SEQ ID NO | Sequence (5'→3') | Mutation | Plasmid | Strain |
|---|---|---|---|---|
| 37 | gttttatgaatttgccaaagaacagttt cag | Y94A L321K | pC2-2 | C2-2 |
| 38 | ctgaaactgttctttggcaaattcataa aac | | | |
| 39 | gttttatgaatttgcccgtgaacagttt cag | Y94A L321R | pC2-3 | C2-3 |
| 40 | ctgaaactgttcacgggcaaattcataa aac | | | |

TABLE 3-continued

| SEQ ID NO | Sequence (5'→3') | Mutation | Plasmid | Strain |
|---|---|---|---|---|
| 41 | gatggtgatctgtatgaactggcccaga acttc | Y94A I341E | pC2-4 | C2-4 |
| 42 | gaagttctgggccagttcatacagatca ccatc | | | |
| 43 | gatggtgatctgtatgatctggcccaga acttc | Y94A I341D | pC2-5 | C2-5 |
| 44 | gaagttctgggccagatcatacagatca ccatc | | | |
| 45 | cgtgcacatgcaaaacgtgaaaaagatg g | Y94A V332K | pC2-7 | C2-7 |
| 46 | ccatcttttcacgttttgcatgtgcac g | | | |
| 47 | cgaccaaacagaccgaagcaaaactgca gcag | Y94A I301E | pC2-8 | C2-8 |
| 48 | ctgctgcagttttgcttcggtctgtttg gtcg | | | |
| 49 | cagcagagcgatattgcgaaaatggaaa acgag | Y94A W310A | pC2-10 | C2-10 |
| 50 | ctcgttttccattttcgcaatatcgctc tgctg | | | |
| 51 | cagcagagcgatattaacaaaatggaaa acgag | Y94A W310N | pC2-11 | C2-11 |
| 52 | ctcgttttccattttgttaatatcgctc tgctg | | | |
| 53 | aatggaaaacgagtttgctgaatttgcc c | Y94A Y317A | pC2-12 | C2-12 |
| 54 | gggcaaattcagcaaactcgttttccat t | | | |
| 55 | ccgaaggtggtagcgaatgtgcaccgga aaaac | Y94A L321R D208E | pC2-22 | C2-22 |
| 56 | gttttccggtgcacattcgctaccacc ttcgg | | | |
| 57 | ctggtgggtgtgctggaagaactggaag | Y94A L321R T254L | pC2-25 | C2-25 |
| 58 | cttccagttcttccagcacacccaccag | | | |
| 59 | gatatttggaaaatggaatacagtttt atgaatttg | Y94A L321R N314Y | pC2-26 | C2-26 |
| 60 | caaattcataaaactcgtattccatttt ccaaatatc | | | |
| 61 | gatatttggaaaatggaacgcgagtttt atgaatttg | Y94A L321R N314R | pC2-27 | C2-27 |
| 62 | caaattcataaaactcgcgttccatttt ccaaatatc | | | |
| 63 | gatatttggaaaatggaaaaagagtttt atgaatttg | Y94A L321R N314K | pC2-28 | C2-28 |
| 64 | caaattcataaaactcttttccatttt ccaaatatc | | | |

(3) Construction of Expression Strain

An *Escherichia coli* Origami B (DE3) stain (Novagen) was transformed with chaperonin expression plasmid pGro7 (TaKaRa), thereby constructing *Escherichia coli* Origami B (DE3)/pGro7. This was transformed with plasmids pC-1, 2, 3, 4, 5, 6, 7, 8, 10, 11, 20, 21, 22, 23, 24, 25, 26, 27, and 28 as construed in the above (1) and (2), respectively, thereby obtaining strains C2-1, 2, 3, 4, 5, 6, 7, 8, 10, 11, 20, 21, 22, 23, 24, 25, 26, 27, and 28.

Example 3: Expression of 2-OST and Preparation of Cell-Free Extract

The strain obtained in Example 2 was inoculated in an LB medium having 100 μg/mL of ampicillin and 25 μg/mL of chloramphenicol added thereto and pre-cured overnight at 37° C. Thereafter, the culture broth was inoculated in 100 mL of an (LB+Glycerol) medium having 100 μg/mL ampicillin and 25 μg/mL of chloramphenicol added thereto contained in a 500 mL-volume Sakaguchi flask such that the final concentration was 1%. Shaking culture was performed at 37° C. until the OD660 became 0.5 to 0.7. Thereafter, IPTG (Nacalai Tesque, Inc.) in a final concentration of 0.5 mM and L-arabinose (Wako Pure Chemical Industries, Ltd.) in a final concentration of 0.2% were added, and the resultant was further cultured overnight at 22° C.

After centrifuging the culture both, the bacterial cell was recovered, once washed with a buffer-2 (20 mM of Tris-HCl (pH: 7.5), 200 mM of NaCl, and 15% of glycerol), and then suspended in the buffer-2 in an amount of 1/10 of the culture broth. Subsequently, the bacterial cell was subjected to ultrasonication with Bioruptor (Sonic Bio Co., Ltd.), and after centrifugation at 14,000 rpm for 20 minutes, a supernatant was obtained as a cell-free extract.

Example 4: Higher-Order Structural Analysis and Measurement of Activator (Trimer) Ratio by Molecular Weight Fractionation 0.5 mL of the cell-free extract obtained in Example 3 was injected into Superose 6 increase 10/300 column (GE Healthcare) equilibrated with the buffer-2 in advance and was subjected to molecular weight fractionation at a flow rate of 0.25 mL/min. The permeated liquids after the 0.2-fold volume of the column volume were collected to a 98-well plate in 0.4 mL per well. As the molecular weight standards, a gel filtration standard (Bio-Rad, #151-1901) and a molecular weight marker (HPLC) (Oriental Yeast Co., Ltd., #46804000) were used.

To 10 μL of each fraction, 2 μL of a sample buffer (for SDS-PAGE, 6-fold-concentrated, containing a reducing agent) (Nacalai Tesque, Inc.) was added, and the contents were thermally denatured at 95° C. for 5 minutes. The whole amount was subjected to SDS-PAGE using 4 to 20% of a Criterion (registered trademark), TGX (registered trademark) precast gel, and the gel was dyed with Bullet CBB Stain One (Ready To Use) (Nacalai Tesque, Inc.). Originally, 2-OST forms a trimer as the activator, and the trimer is eluted in the vicinity at the 29th of the fraction (C3 fraction); however, it was estimated that a lot of 2-OST is also eluted in a fraction having a larger estimated molecular weight cut-off than the trimer, to form a polymer. Then, the dyed imager of the gel was captured on Amersham Imager 600 (GE Healthcare), and the band intensities of 2-OST in the 9th (A9) of the fraction at which 2-OST showing the molecular weight of the polymer was cut off and 2-OST in the 29th (C3) of the fraction at which 2-OST showing the molecular weight of the trimer was cut off were analyzed with Image QuantTL (GE Healthcare). From the analysis results of each band intensity, [(band intensity of C3 fraction)/(band intensity of A9 fraction)×100] was calculated and defined as an index expressing a portion at which the activator is contained.

The results of calculation of an activator rate of the cell-free extract prepared from the various mutant expression strains are shown in Table 4. As shown below, the index of activator rate is improved by mutation introduction of L321R

TABLE 4

Index of activator rate

| Strain | Mutation | Activator rate (C3/A9 fraction × 100) |
|---|---|---|
| C2-1 | Y94A | 32.3 |
| C2-2 | Y94A/L321K | 38.1 |
| C2-3 | Y94A/L321R | 66.4 |
| C2-4 | Y94A/I341E | 16.3 |
| C2-5 | Y94A/I341D | 25.4 |
| C2-7 | Y94A/V323K | 16.0 |
| C2-8 | Y94A/I301E | 13.2 |
| C2-10 | Y94A/W310A | 20.2 |
| C2-11 | Y94A/W310N | 4.5 |
| C2-12 | Y94A/Y317A | 7.1 |
| C2-22 | Y94A/L321R/D208E | 65.7 |
| C2-25 | Y94A/L321R/T254L | 67.0 |

Example 5: 2-O-Sulfation Reaction with Cell-Free Extract (1) 2-O-Sulfation Reaction The reaction was carried out using, as a substrate, the N-sulfated epimerized depolymerized heparosan prepared in Example 1. To the reaction liquid (2 mg/mL of N-sulfated epimerized depolymerized heparosan, 0.6 mM of 3'-Phosphoadenosine-5'-phosphosulfate and 50 mM of MES (pH 7.0)), 1.9% of each cell-free extract was added, a reaction was performed at 37° C. for 30 minutes, and the resultant was mixed with 2 times the amount of 2.0 M citric acid aqueous solution, followed by performing a heat treatment at 95° C. for 15 minutes, thereby stopping the reaction. As a negative control, an enzymatic reaction was carried out under a condition at which the buffer-2 was added to the reaction liquid in place of the cell-free extract.

A 2-O-sulfation rate was quantified through disaccharide composition analysis. The 2-O-sulfation rate was calculated from a ratio of IdoA-GlcN(NS) and IdoA2S-GlcN(NS) as determined by HPLC analysis, and a value obtained by subtracting a 2-O-sulfation rate of the negative control from the respective 2-O-sulfation rate was determined as a proportion converted in the 2-O-sulfation reaction. A converted amount of substance was calculated from the molecular weight, 415.8 of IdoA-GlcNS that is a disaccharide unit. An enzyme unit (U) was defined as an enzyme amount for producing 1 μmol of IdoA(2S)-Glc(NS) for one minute under the above described condition. In Example 4, while the ratio of the activator (trimer) in the cell-free extract was improved about two-fold due to L321R mutation introduction, and an improvement of activity was expected, as estimated from the activator rate, the 2-O-sulfation activity was largely improved from 135 U/mL to 330 U/mL due to the mutation introduction of L321R (Table 5).

TABLE 5

2-O-Sulfation activity of L321R mutant

| Strain | Mutation | Specific activity (U/mL) |
|---|---|---|
| C2-1 | Y94A | 135 |
| C2-3 | Y94A/L321R | 330 |

(2) Quantification of Conversion Rate (Disaccharide Composition Analysis)

The quantification of the conversion rate (2-O-sulfation rate and 3-O-sulfation rate) was carried out through disaccharide composition analysis by nitrous acid degradation.

<Reagents>
NaNO$_2$ (CAS No.: 7632-00-0, MW: 69.01)
Citric acid (CAS No.: 77-92-9, MW: 192.1)
2,4-Dinitrophenyl hydrazine (CAS No.: 119-26-6, MW: 198.1), containing 50% of water (abbreviation: DNPH)
Heparin (manufactured by Aldrich)
<Testing Liquids>
Heparin standard solution: 1 mg/mL
NaNO$_2$ aqueous solution: Solution of 49.5 mg of the reagent dissolved in 1 mL of H$_2$O
Citric acid aqueous solution: Solution of 384.2 mg of the reagent dissolved in 1 mL of H$_2$O
DNPH aqueous solution: Solution of 20.4 mg of the reagent (containing 50% of water) dissolved in 1 mL of acetonitrile
<LC-MS Analysis Condition>
<LC Conditions>

Column: ODS Z-CLUE 3 μm (manufactured by Sumika Chemical Analysis Service, Ltd.) 2.0 mm×250 mm
Column case temperature: 50° C.
Flow rate of eluting solution: 0.3 mL/min
Detection: UV 365 nm
Injection amount: 5 μL
Composition of eluting solution:
Solution A: 50 mM-HCOONH$_4$ (pH: 4.5)
Solution B: MeCN

TABLE 6

Gradient condition of LC

| Time (min) | Solution A (%) | Solution B (%) |
|---|---|---|
| 0.0 | 90 | 10 |
| 13.0 | 80 | 20 |
| 27.0 | 20 | 80 |
| 27.1 | 90 | 10 |
| 40.0 | 90 | 10 |

<Ms Conditions>
Ionization method: Electrospray ionization (ESI (+/−))
DL temperature: 250° C.
Heat block: 250° C.
Nebulizer gas flow rate: 1.5 L/min
Dry gas flow rate: 15 L/min

TABLE 7

Information regarding MS

| Disaccharide derivative (showing the structure before nitrous acid degradation) | m/z (−) | Relative retention time (min) |
|---|---|---|
| GlcA-GlcN(NS3S6S) | 677 | 0.83 |
| GlcA(2S)-GlcN(NS6S) |  | 0.97 |
| IdoA(2S)-GlcN(NS6S) |  | 1 |
| GlcA-GlcN(NS6S) | 597 | 1.35 |
| GlcA(2S)-GlcN(NS) |  | 1.41 |
| IdoA(2S)-GlcN(NS) |  | 1.50 |
| GlcA-GlcN(NS) | 517 | 1.73 |
| IdoA-GlcN(NS) |  | 1.89 |

<Analysis Procedures and Results>

In a 1.5 mL-microtube (Eppendorf), 10 μL of the heparin standard solution or test solution, 20 μL of the citric acid buffer aqueous solution, and 10 μL of the NaNO$_2$ aqueous solution were successively added, and the mixed solution was stirred (at 1,000 rpm) at 65° C. for 2 hours, thereby obtaining a nitrous acid degraded liquid. To 40 μL of the obtained nitrous acid degraded liquid, 20 μL of the DNPH solution was added, and the contents were stirred (at 1,000 rpm) at 45° C. for 2 hours, thereby obtaining a derivatized liquid. A composition of the obtained derivatized liquid was analyzed by LC-MS. From a peak of IdoA(2S)-GlcN(NS6S) obtained by analyzing the heparin standard solution, a conversion factor (area purity of (1 mg×IdoA(2S)-GlcN (NS6S))/(area value of IdoA(2S)-GlcN(NS6S)) was calculated, and a concentration of each disaccharide derivative in the test solution was determined from the area value thereof. A calculated disaccharide structure and its proportion are shown in Table 3. In the table, any data regarding unidentified peaks which are considered to contain a disaccharide derivative having the N-acetyl group, etc. are omitted, and the total amount of GlcA(2S)-GlcN(NS), IdoA(2S)-GlcN (NS), GlcA-GlcN(NS), and IdoA-GlcN(NS) was defined as 100%.

Example 6: Preparation of N-Sulfated, 6-O-Sulfated and Depolymerized Heparosan (1) 6-O-Sulfation of N-Sulfated and Depolymerized Heparosan
<Purification Before Reaction>

30 mL of the N-sulfated and depolymerized heparosan obtained in Example 1(5) was centrifuged (at 7000G for 30 minutes), and its supernatant was filtered with a 0.45 μm-filter. 27.3 g of the filtrate was charged in 15 g of a weak anion exchange resin (DIAION, WA-30, manufactured by Mitsubishi Chemical Corporation; previously adjusted to a pH 5.5 with 25.6 mM of NaH$_2$PO$_4$) which was filled in a Pharmacia's column (model number: XK26) to adsorb polysaccharide components, and 480 mL of a washing liquid (0.5 M of NaCl+25.6 mM of NaH$_2$PO$_4$ (pH 5.5)) was passed therethrough (flow rate: 6.4 mL/min). Subsequently, 230 mL of an eluting solution (2 M of NaCl+25.6 mM of NaH$_2$PO$_4$ (pH 5.5)) was passed through the resultant (flow rate: 6.4 mL/min), thereby obtaining an eluting solution containing polysaccharide components. The obtained eluting solution was charged in Amicon-3K (manufactured by Merck Millipore) and centrifuged (at 4,000 G). 100 mL of water was further added to the obtained concentrated liquid, and centrifugation was again performed. This washing operation was carried out three times, thereby obtaining 11 g of a washed concentrated liquid.

<Ion Exchange>

11 g of the washed concentrated liquid was passed through 3 mL of a strong cation exchange resin (DIAION, UBK550, manufactured by Mitsubishi Chemical Corporation; previously converted into an H type with 1M hydrochloric acid) (pH 2.25), and 1.8 mL of a mixed liquid of 2.36 mg of tributylamine and 10 μL of ethanol was then added to perform neutralization (pH 8.36). The obtained neutralized liquid was freeze-dried.

<6-O-Sulfation Reaction>

To the entire amount of the freeze-dried material, 1.92 mL of DMF and 76.4 mg (0.48 mmol) of a sulfur trioxide pyridine adduct were added under an argon gas stream, and the contents were stirred at −10° C. for 48 hours. To the reaction liquid, 2.8 mL of a 5M sodium acetate aqueous solution and 31 mL of water were added, and the contents were stirred at room temperature for one hour, thereby stopping the reaction. The reaction stop liquid was filtered with a 0.2 μm-filter, and the filtrate was charged in Amicon-3K (manufactured by Merck Millipore) and centrifuged (at 4,000 G). 20 mL of water was further added to the obtained concentrated liquid, and centrifugation was again performed. This washing operation was carried out two times, thereby obtaining 3.92 g of a washed concentrated liquid. The obtained washed concentrated liquid was sampled and subjected to disaccharide composition analysis through nitrous acid degradation in the same procedures as in Example 1. As a result, it was confirmed that 76.5 mg of the reaction product, N-sulfated, 6-O-sulfated and depolymerized heparosan in terms of an amount of the disaccharide unit was contained in 3.92 g of the washed concentrated liquid.

Example 7: Construction of 3-O-Sulfation Enzyme (3-OST-1) Expression Strain (1) Construction of pETDuet-3-OST-1

An amino acid sequence of mouse-derived 3-OST-1 (NCBI-Protein ID: NP 034604; SEQ ID NO: 8) was obtained from the data base of KEGG (Kyoto Encyclopedia of Genes and Genomes). A DNA fragment containing a base sequence (SEQ ID NO: 9) encoding a catalytic site of the 3-OST-1 (Gly48-His311; SEQ ID NO: 10) optimized in conformity with the codon usage of *Escherichia coli* was synthesized by reference to the previous report (Edavettal S. C., et al., *J Bio Chem.*, 2004; 279(24) 25789-97). The obtained DNA fragment was inserted into an EcoRI-SalI site of a pETDuet-1 vector (Novagen), thereby constructing a 3-OST-1 expression plasmid, pETDuet-3-OST-1. According to this expression plasmid, 3-OST-1 in which His-Tag is added to the N-terminal side is expressed, and therefore, it becomes possible to purify the 3-OST-1 by the His tag.

(2) Construction of Mutant Type 3-OST-1 Expression Plasmid

In order to construct a mutant type 3-OST-1 expression plasmid, by using primers (SEQ ID NOS: 65 to 138) corresponding to various mutant types, PCR was carried out using pETDuet-3-OST-1 as the template. A relation between each mutation and primer is shown in Table 6. After digesting the obtained PCR product with DpnI, an *Escherichia coli* JM109 strain was transformed with the reaction liquid and applied to an LB agar medium containing 100 μg/mL of ampicillin, followed by culturing overnight at 37° C. The plasmid was extracted from a colony of the grown transformed microorganisms according to a known method. The nucleotide sequence was confirmed with a 3100 Genetic Analyzer (manufactured by Applied Biosystems), thereby obtaining plasmids pET3OST #1, 3, 4, 5, 6, 7, 8, 9, 10, 11, 12, 13, 14, 16, 17, 18, 19, 20, 21, 23, 24, 25, 26, 27, 28, 29, 30, 31, 32, 33, 34, 35, 36, 37, 38, 39, and 40, each having an objective structure. The relations among each mutation, primer, and plasmid are shown in Tables 8-1 and 8-2.

TABLE 8-1

| SEQ ID NO | Sequence (5'→3') | Mutation | Plasmid | Strain |
|---|---|---|---|---|
| 65 | cggtgttcgtaaacatggcacccgtgcactg | G69H | pET3OST #1 | 3OS-1 |
| 66 | cagtgcacgggtgccatgtttacgaacaccg | | | |
| 67 | gtgcactgctggaaaaactgagcctgcatcc | M77K | pET3OST #3 | 3OS-3 |
| 68 | ggatgcaggctcagttttttccagcagtgcac | | | |
| 69 | gtgcactgctggaataccctgagcctgcatcc | M77Y | pET3OST #4 | 3OS-4 |
| 70 | ggatgcaggctcaggtattccagcagtgcac | | | |
| 71 | ctgaccgttgaaaaacgtccggcatatttcac | T124R | pET3OST #5 | 3OS-5 |
| 72 | gtgaaatatgccggacgttttttcaacggtcag | | | |
| 73 | ctgaccgttgaaaaacacccggcatatttcac | T124H | pET3OST #6 | 3OS-6 |
| 74 | gtgaaatatgccgggtgttttttcaacggtcag | | | |
| 75 | ctgaccgttgaaaaaaaaccggcatatttcac | T124K | pET3OST #7 | 3OS-7 |
| 76 | gtgaaatatgccggttttttttcaacggtcag | | | |
| 77 | gcgattatacccagcgtctgtataatcatctg | V164R | pET3OST #8 | 3OS-8 |
| 78 | cagatgattatacagacgctgggtataatcgc | | | |
| 79 | cccaggttctgtatcatcatctgcagaaac | N167H | pET3OST #9 | 3OS-9 |
| 80 | gtttctgcagatgatgatacagaacctggg | | | |
| 81 | ccgttgaaaaaacagcggcatatttcaccag | P125A | pET3OST #10 | 3OS-10 |
| 82 | ctggtgaaatatgccgctgttttttcaacgg | | | |
| 83 | cccaggttctgtataaacatctgcagaaac | N167K | pET3OST #11 | 3OS-11 |
| 84 | gtttctgcagatgtttatacagaacctggg | | | |
| 85 | cccgtgcactgctgcagatgctgagcctgc | E76Q | pET3OST #12 | 3OS-12 |
| 86 | gcaggctcagcatctgcagcagtgcacggg | | | |
| 87 | cccgtgcactgctgaacatgctgagcctgc | E76N | pET3OST #13 | 3OS-13 |
| 88 | gcaggctcagcatgttcagcagtgcacggg | | | |
| 89 | gttgcagcagcagaacatgaagtgcatttttttg | N89H | pET3OST #14 | 3OS-14 |
| 90 | caaaaaaatgcacttcatgttctgctgctgcaac | | | |
| 91 | gtgcattttttttgatttcgaggaacattatag | W96F | pET3OST #16 | 3OS-16 |
| 92 | ctataatgttcctcgaaatcaaaaaaatgcac | | | |
| 93 | gtataatcatctgcagcagcataaaccgtatcc | K171Q | pET3OST #17 | 3OS-17 |
| 94 | ggatacggtttatgctgctgcagatgattatac | | | |
| 95 | gtataatcatctgcagaaccataaaccgtatcc | K171N | pET3OST #18 | 3OS-18 |
| 96 | ggatacggtttatggttctgcagatgattatac | | | |
| 97 | caaaaccaaaggcttcttttgcctgcgtgatag | Y259F | pET3OST #19 | 3OS-19 |
| 98 | ctatcacgcaggcaaaagaagcctttggttttg | | | |
| 99 | gcgattatacccagattctgtataatcatctg | V164I | pET3OST #20 | 3OS-20 |
| 100 | cagatgattatacagaatctgggtataatcgc | | | |

TABLE 8-1-continued

| SEQ ID NO | Sequence (5'→3') | Mutation | Plasmid | Strain |
|---|---|---|---|---|
| 101 | gatggtgatcgtctggttcgtgatccgtttcc | I225V | pET3OST | 3OS-21 |
| 102 | ggaaacggatcacgaaccagacgatcaccatc | | #21 | |

TABLE 8-2

| SEQ ID NO | Sequence (5'→3') | Mutation | Plasmid | Strain |
|---|---|---|---|---|
| 103 | gtctgaatctggattttaaagcactgaatcg | Y192F | pET3OST | 3OS-23 |
| 104 | cgattcagtgctttaaaatccagattcagac | | #23 | |
| 105 | ccattattatcggtattcgtaaaggtggcac | V66I | pET3OST | 3OS-24 |
| 106 | gtgccacctttacgaataccgataataatgg | | #24 | |
| 107 | cattcgcctgctgctggttctgcgtgatccgag | I149V | pET3OST | 3OS-25 |
| 108 | ctcggatcacgcagaaccagcagcaggcgaatg | | #25 | |
| 109 | cagaaacataaaccgtttccgcctattgaag | Y175F | pET3OST | 3OS-26 |
| 110 | cttcaataggcggaaacggtttatgtttctg | | #26 | |
| 111 | gattatacccaggttctgtttaatcatctgcagaaac | Y166F | pET3OST | 3OS-27 |
| 112 | gtttctgcagatgattaaacagaacctgggtataatc | | #27 | |
| 113 | gaaaaacaccggcatttttcaccagcccgaaag | Y127F | pET3OST | 3OS-28 |
| 114 | ctttcgggctggtgaaaaatgccggtgttttttc | | #28 | |
| 115 | gtgttctgagcgattttacccaggttctg | Y161F | pET3OST | 3OS-29 |
| 116 | cagaacctgggtaaaatcgctcagaacac | | #29 | |
| 117 | gattaatgccagcaactactattttaacaaaac | F250Y | pET3OST | 3OS-30 |
| 118 | gttttgttaaaatagtagttgctggcattaatc | | #30 | |
| 119 | gtgcactgctggaactgctgagcctgcatcc | M77L | pET3OST | 3OS-31 |
| 120 | ggatgcaggctcagcagttccagcagtgcac | | #31 | |
| 121 | ctattttaacaaaaccgtggcttctattgcctg | K256R | pET3OST | 3OS-32 |
| 122 | caggcaatagaagccacgggttttgttaaaatag | | #32 | |
| 123 | gatggtgatcgtctgctgcgtgatccgtttcc | I225L | pET3OST | 3OS-33 |
| 124 | ggaaacggatcacgcagcagacgatcaccatc | | #33 | |
| 125 | ctgaatctggattatcgtgcactgaatcgtag | K193R | pET3OST | 3OS-34 |
| 126 | ctacgattcagtgcacgataatccagattcag | | #34 | |
| 127 | cattcgcctgctgctgctgctgcgtgatccgag | I149L | pET3OST | 3OS-35 |
| 128 | ctcggatcacgcagcagcagcagcaggcgaatg | | #35 | |
| 129 | gaacgtgttctgagcgaatatacccaggttctg | D160E | pET3OST | 3OS-36 |
| 130 | cagaacctgggtatattcgctcagaacacgttc | | #36 | |
| 131 | gatgttgcagcagcagacaatgaagtgcattttttt | E88D | pET3OST | 3OS-37 |
| 132 | aaaaaaatgcacttcattgtctgctgctgcaacatc | | #37 | |
| 133 | ctgcgtgatccgagcgaccgtgttctgagcg | E155D | pET3OST | 3OS-38 |
| 134 | cgctcagaacacggtcgctcggatcacgcag | | #38 | |
| 135 | gatcgttgtctgcatgacagcaaaggtcgtgc | E272D | pET3OST | 3OS-39 |
| 136 | gcacgacctttgctgtcatgcagacaacgatc | | #39 | |
| 137 | cccgtgcactgctggacatgctgagcctgc | E76D | pET3OST | 3OS-40 |
| 138 | gcaggctcagcatgtccagcagtgcacggg | | #40 | |

(3) Construction of 3-OST-1 Expression Strain

An expression plasmid, pETDuet-3-OST-1 possessing wild-type 3-OST-1 and 37 kinds of expression plasmid pET3OST possessing mutant type 3-OST-1 were introduced into *Escherichia coli* BL21(DE3) using the same method as in Example 1(5), thereby obtaining a wild-type 3-OST-1 expression strain pETDuet-3-OST-1/BL21(DE3) strain (3OS-WT) and 37 kinds of mutant type 3-OST-1 expression strains.

Example 8: Expression of 3-OST and Preparation of Cell-Free Extract

The strain obtained in Example 7 was inoculated in 3 mL of an LB medium containing 100 µg/ML of ampicillin (1.0% (w/v) of peptone, 0.5% (w/v) of a yeast extract, 1.0% (w/v) of NaCl, and 1.5% (w/v) of agar) and pre-cured overnight in a test tube at 37° C. Solution A consisting of 1.2% (w/v) of tryptone (manufactured by BD), 2.4% (w/v) of a yeast extract (manufactured by BD), 0.5% (w/v) of glycerin (manufactured by Junsei Chemical Co., Ltd.), and water was prepared by treating at 120° C. for 20 minutes in an autoclave. Solution B consisting of 2.3% (w/v) of potassium dihydrogenphosphate (manufactured by Junsei Chemical Co., Ltd.), 12.5% (w/v) of dipotassium hydrogenphosphate (manufactured by Junsei Chemical Co., Ltd.), and water was prepared through filtration with a 0.45 µm-filter (manufactured by Merck). The above-described solution A and solution B were mixed in an AB ratio of 9/1 in a sterile environment, thereby preparing a TB medium. The pre-cured culture broth was added to 3 mL of the TB medium (containing 100 µg/mL of ampicillin) contained in a test tube such that the final concentration was 1% and subjected to shaking culture at 37° C. and 120 reciprocations per minute until the OD660 reached 0.5 to 0.7. Then, IPTG (Nacalai Tesque, Inc.) was added such that the final concentration was 0.2 mM, and the contents were further subjected to shaking culture for 24 to 26 hours. 1 mL of the culture broth was harvested through centrifugation (at 4° C. and 15,000 rpm for 5 minutes). A bacterial cell obtained as a precipitate was suspended in 1 mL of an equilibrated buffer (50 mM of sodium phosphate and 300 mM of NaCl, pH: 7.0) and again centrifuged (at 4° C. and 8,000 rpm for 5 minutes), thereby washing the bacterial cell. After repeating the washing operation two times, a bacterial cell obtained as a precipitate was again suspended in 400 µL of an equilibrated buffer and subjected to ultrasonication with Bioruptor (Sonic Bio Co., Ltd.) while cooling at 4° C. with cold water. The disputed liquid was centrifuged (at 4° C. and 15,000 rpm for 20 minutes), and the obtained supernatant was defined as the cell-free extract.

Example 9: 3-O-Sulfation Reaction with Cell-Free Extract (1) 3-O-Sulfation Reaction of GlcN Residue The reaction was carried out using, as a substrate, the N-sulfated, 6-O-sulfated and depolymerized heparosan prepared in Example 6. 80 µL of a mixed liquid of 1 g/L of N-sulfated, 6-O-sulfated and depolymerized heparosan, 1.25 mM of PAPS, and 50 mM of HEPES (pH 7.5) was prepared as the reaction liquid. To the mixed liquid which was kept warm at 37° C. in a water bath in advance, 20 µL of the cell-free extract prepared in Example 8 was added to commence the enzymatic reaction. The reaction was allowed to proceed at 37° C., and after elapsing one hour, the reaction mixture was heated at 100° C. for 3 minutes, thereby inactivating the enzyme.

(2) Quantification of 3-O-Sulfation Rate of GlcN Residue

The disaccharide composition analysis of the reaction product was performed through nitrous acid degradation in the same procedures as in Example 5(2). The reaction stop liquid was subjected to disaccharide composition analysis through nitrous acid degradation, thereby calculating the 3-O-sulfation rate. A calculation method of the 3-O-sulfation rate is made according to the formula (I).

$$\text{3-O-Sulfation rate (\%)} = \frac{\text{GlcA-Glc(NS}_3\text{S}_6\text{S})}{\text{GlcA-Glc(NS}_3\text{S}_6\text{S}) + \text{GlcA-Glc(NS}_6\text{S})} \times 100 \quad (I)$$

(3) Activity Evaluation of Mutant Type 3-OST-1

The 3-OST activity was calculated on the basis of the 3-O-sulfation rate determined in Example 9(2). The amount of enzyme for producing 1 µmol of a 3-O-sulfated disaccharide unit GlcA-GlcNS3S6S (molecular weight 593) for one minute was defined as 1 U. When defining the enzymatic activity of wild-type 3-OST-1 as 1, the mutant type 3-OST relative activity is shown in Table 9. As a result of the activity evaluation, it has become clear that by mutation introduction of each of M77K, P125A, and V164I, the 3-OST activity is improved.

TABLE 9

| Strain | Mutation | Relative activity when defining the enzymatic activity of wild-type 3-OST-1 as 1 |
|---|---|---|
| 3-OS-WT | — | 1.00 |
| 3OS-1 | G69H | 0.38 |
| 3OS-3 | M77K | 1.82 |
| 3OS-4 | M77Y | 0.90 |
| 3OS-5 | T124R | 0.32 |
| 3OS-6 | T124H | 0.43 |
| 3OS-7 | T124K | 0.24 |
| 3OS-8 | V164R | 1.02 |
| 3OS-9 | N167H | 1.32 |
| 3OS-10 | P125A | 1.74 |
| 3OS-11 | N167K | 0.35 |
| 3OS-12 | E76Q | 0.58 |
| 3OS-13 | E76N | 0.36 |
| 3OS-14 | N89H | 0.79 |
| 3OS-16 | W96F | 1.20 |
| 3OS-17 | K171Q | 1.21 |
| 3OS-18 | K171N | 0.95 |
| 3OS-19 | Y259F | 1.15 |
| 3OS-20 | V164I | 1.97 |
| 3OS-21 | I225V | 0.73 |
| 3OS-23 | Y192F | 0.52 |
| 3OS-24 | V66I | 0.26 |
| 3OS-25 | I149V | 0.99 |
| 3OS-26 | Y175F | 0.59 |
| 3OS-27 | Y166F | 0.76 |
| 3OS-28 | Y127F | 0.28 |
| 3OS-29 | Y161F | 0.30 |
| 3OS-30 | F250Y | 0.45 |
| 3OS-31 | M77L | 0.30 |
| 3OS-32 | K256R | 0.65 |
| 3OS-33 | I225L | 0.45 |
| 3OS-34 | K193R | 0.71 |
| 3OS-35 | I149L | 0.26 |
| 3OS-36 | D160E | 0.26 |
| 3OS-37 | E88D | 0.79 |
| 3OS-38 | E155D | 0.88 |
| 3OS-39 | E272D | 0.18 |
| 3OS-40 | E76D | 0.24 |

Sequence Listing Free Text

SEQ ID No: 1 shows Full-length nucleotide sequence encoding Chinese hamster-derived 2-O-sulfation enzyme (2-OST).

SEQ ID No: 2 shows Full-length amino acid sequence of Chinese hamster-derived 2-O-sulfation enzyme (2-OST).

SEQ ID No: 3 shows Amino acid sequence of catalytic sites (Asp69-Asn356) of Chinese hamster-derived 2-O-sulfation enzyme (2-OST).

SEQ ID No: 4 shows Full-length amino acid sequence of Chinese hamster-derived 2-O-sulfation enzyme (2-OST) having Y94A mutation.

SEQ ID No: 5 shows Nucleotide sequence encoding catalytic sites (Asp69-Asn356) of Chinese hamster-derived 2-O-sulfation enzyme (2-OST) having Y94A mutation, as optimized in conformity with codon usage in *Escherichia coli*.

SEQ ID No: 6 shows Amino acid sequence of catalytic sites (Asp69-Asn356) of Chinese hamster-derived 2-O-sulfation enzyme (2-OST) having Y94A mutation.

SEQ ID No: 7 shows Full-length nucleotide sequence encoding mouse-derived 3-O-sulfation enzyme (3-OST-1).

SEQ ID No: 8 shows Full-length amino acid sequence of mouse-derived 3-O-sulfation enzyme (3-OST-1).

SEQ ID No: 9 shows Nucleotide sequence encoding catalytic sites (Gly48-His311) of mouse-derived 3-O-sulfation enzyme (3-OST-1), as optimized in conformity with codon usage in *Escherichia coli*.

SEQ ID No: 10 shows Amino acid sequence of catalytic sites (Gly48-His311) of mouse-derived 3-O-sulfation enzyme (3-OST-1).

SEQ ID No: 11 shows Nucleotide sequence of primer P1.
SEQ ID No: 12 shows Nucleotide sequence of primer P2.
SEQ ID No: 13 shows Nucleotide sequence of nucleotide sequence of PaeI-SalI fragment of PnlpO promoter.
SEQ ID No: 14 shows Nucleotide sequence of primer P3.
SEQ ID No: 15 shows Nucleotide sequence of primer P4.
SEQ ID No: 16 shows Nucleotide sequence of DNA fragment containing about 300 bp of terminator region of rrnB gene.
SEQ ID No: 17 shows Nucleotide sequence of primer P5.
SEQ ID No: 18 shows Nucleotide sequence of primer P6.
SEQ ID No: 19 shows Nucleotide sequence of primer P7.
SEQ ID No: 20 shows Nucleotide sequence of primer P8.
SEQ ID No: 21 shows Nucleotide sequence of hepC gene cloned in Example 1.
SEQ ID No: 22 shows Amino sequence of heparinase III (HepC) encoding nucleotide sequence of SEQ ID: NO 21.
SEQ ID No: 23 shows Nucleotide sequence of pMAL-c2× plasmid.
SEQ ID NOS: 24 and 25 show Nucleotide sequences of primers used for preparing MBP* in Example 1.
SEQ ID No: 26 shows Nucleotide sequence of pMAL-MBP* plasmid.
SEQ ID NOS: 27 and 28 show Nucleotide sequences of primers used for obtaining DNA fragment of pMAL-MBP* in Example 1.
SEQ ID NOS: 29 and 30 show Nucleotide sequences of primers used for obtaining fragment of zebrafish-derived D-glucuronyl C5-epimerase in Example 1.
SEQ ID NO: 31 shows Codon-optimized nucleotide sequence encoding partial amino acid sequences (Gly70-Asn585) of zebrafish-derived D-glucuronyl C5-epimerase.
SEQ ID NO: 32 shows Partial amino acid sequences (Gly70-Asn585) of zebrafish-derived D-glucuronyl C5-epimerase.
SEQ ID NOS: 33 to 138 show Nucleotide sequences of primers.

The invention claimed is:

1. A 2-O-sulfation enzyme mutant comprising:
I) an amino acid sequence selected from the group consisting of:
   (a) the amino acid sequence of SEQ ID NO: 2;
   (b) an amino acid sequence comprising one to thirty amino acid substitutions, deletions, insertions, or additions in the amino acid sequence of SEQ ID NO: 2;
   (c) an amino acid sequence having 90% or more identity to the amino acid sequence of SEQ ID NO: 2;
   (d) the amino acid sequence consisting of amino acid residues at positions 69 to 356 in the amino acid sequence of SEQ ID NO: 2;
   (e) an amino acid sequence comprising one to twenty amino acid substitutions, deletions, insertions, or additions in the amino acid sequence consisting of amino acid residues at positions 69 to 356 in the amino acid sequence of SEQ ID NO: 2; and
   (f) an amino acid sequence having 90% or more identity to the amino acid sequence consisting of amino acid residues at positions 69 to 356 in the amino acid sequence of SEQ ID NO: 2;
II) a substitution of a leucine residue at position 321, relative to the amino acid sequence of SEQ ID NO: 2, with a basic amino acid residue; and
III) a 2-O-sulfate transfer activity.

2. The 2-O-sulfation enzyme mutant according to claim 1, wherein the basic amino acid residue is an arginine residue or a lysine residue.

3. A method of producing a modified heparosan compound in which a hydroxyl group at 2-position of a hexuronic acid residue in a heparosan compound is sulfated, comprising contacting said heparosan compound with the 2-O-sulfation enzyme mutant of claim to produce the modified heparosan compound comprising a sulfated hydroxyl group at the 2-position of a hexuronic acid residue in said heparosan.

4. The method according to claim 3, wherein the modified heparosan compound is selected from the group consisting of: N-sulfated heparosan, N-sulfated epimerized heparosan, N-sulfated depolymerized heparosan, and N-sulfated epimerized depolymerized heparosan.

5. The method according to claim 3, wherein the 2-O-sulfation enzyme mutant is produced by a transformed microorganism or an extract thereof.

6. The method according to claim 5, wherein the transformed microorganism is a bacterium belonging to the genus *Escherichia*.

7. The method according to claim 6, wherein the bacterium belonging to the genus *Escherichia* is *Escherichia coli*.

8. A method of producing a heparan sulfate, comprising subjecting heparosan to a treatment comprising (1) N-deacetylation of a α-D-glucosamine residue, (2) depolymerization, (3) N-sulfation of the α-D-glucosamine residue, (4) C5-epimerization of a hexuronic acid residue, (5) 2-O-sulfation of the hexuronic acid residue by contacting said heporasan with the 2-O-sulfation enzyme mutant of claim 1, (6) 6-O-sulfation of the α-D-glucosamine residue, and (7) 3-O-sulfation of the α-D-glucosamine residue to produce said heparan sulfate.

9. The 2-O-sulfation enzyme mutant according to claim 1, wherein the amino acid sequence is selected from the group consisting of:
   (a) the amino acid sequence of SEQ ID NO: 2;
   (b) an amino acid sequence comprising one to ten amino acid substitutions, deletions, insertions, or additions in the amino acid sequence of SEQ ID NO: 2;
   (c) an amino acid sequence having 95% or more identity to the amino acid sequence of SEQ ID NO: 2;
   (d) the amino acid sequence consisting of amino acid residues at positions 69 to 356 in the amino acid sequence of SEQ ID NO: 2;
   (e) an amino acid sequence comprising one to ten amino acid substitutions, deletions, insertions, or additions in the amino acid sequence consisting of amino acid residues at positions 69 to 356 in the amino acid sequence of SEQ ID NO: 2; and
   (f) an amino acid sequence having 95% or more identity to the amino acid sequence consisting of amino acid residues at positions 69 to 356 in the amino acid sequence of SEQ ID NO: 2.

10. The 2-O-sulfation enzyme mutant according to claim 1, wherein the the amino acid sequence is selected from the group consisting of::
   (a) the amino acid sequence of SEQ ID NO: 2;
   (b) an amino acid sequence comprising one to five amino acid substitutions, deletions, insertions, or additions in the amino acid sequence of SEQ ID NO: 2;
   (c) an amino acid sequence having 98% or more identity to the amino acid sequence of SEQ ID NO: 2;
   (d) the amino acid sequence consisting of amino acid residues at positions 69 to 356 in the amino acid sequence of SEQ ID NO: 2;
   (e) an amino acid sequence comprising one to five amino acid substitutions, deletions, insertions, or additions in the amino acid sequence consisting of amino acid residues at positions 69 to 356 in the amino acid sequence of SEQ ID NO: 2; and (f) an amino acid sequence having 98% or more identity to the amino acid sequence consisting of amino acid residues at positions 69 to 356 in the amino acid sequence of SEQ ID NO: 2.

* * * * *